US012359214B2

(12) United States Patent
Paladini et al.

(10) Patent No.: US 12,359,214 B2
(45) Date of Patent: Jul. 15, 2025

(54) HIGH EXPRESSION OF ANIMAL HEME PROTEIN IN PLANTS

(71) Applicant: MOOLEC SCIENCE LIMITED, Warwick (GB)

(72) Inventors: Gaston Paladini, Rosario (AR); Martin Salinas, Funes (AR); Amit Dhingra, College Station, TX (US); Henk Hoogenkamp, Molenhoek (NL); Bruce Williamson Benavides, Moscow, ID (US); Maria Laura Malvino, Camarillo, CA (US); Balaji Vasudevan, Apex, NC (US)

(73) Assignee: Moolec Science Limited, Warwick (GB)

( * ) Notice: Subject to any disclaimer, the term of this patent is extended or adjusted under 35 U.S.C. 154(b) by 0 days.

(21) Appl. No.: 18/647,942

(22) Filed: Apr. 26, 2024

(65) Prior Publication Data

US 2024/0352475 A1 Oct. 24, 2024

Related U.S. Application Data

(63) Continuation of application No. PCT/IB2023/056287, filed on Jun. 16, 2023.

(60) Provisional application No. 63/367,299, filed on Jun. 29, 2022.

(51) Int. Cl.

| | |
|---|---|
| ***C12N 15/82*** | (2006.01) |
| ***A23J 3/04*** | (2006.01) |
| ***A23J 3/22*** | (2006.01) |
| ***C07K 14/805*** | (2006.01) |

(52) U.S. Cl.
CPC ............ *C12N 15/8257* (2013.01); *A23J 3/04* (2013.01); *A23J 3/227* (2013.01); *C07K 14/805* (2013.01); *C12N 15/8234* (2013.01)

(58) Field of Classification Search
None
See application file for complete search history.

(56) References Cited

U.S. PATENT DOCUMENTS

| | | | | |
|---|---|---|---|---|
| 9,808,029 | B2 | 11/2017 | Fraser et al. | |
| 9,826,772 | B2 | 11/2017 | Fraser et al. | |
| 10,039,306 | B2 | 8/2018 | Vrljic et al. | |
| 10,863,761 | B2 | 12/2020 | Brown et al. | |
| 10,947,552 | B1 * | 3/2021 | Lanquar | C07K 14/4732 |
| 11,013,250 | B2 | 5/2021 | Vrljic et al. | |
| 11,219,232 | B2 | 1/2022 | Fraser et al. | |
| 11,224,241 | B2 | 1/2022 | Fraser et al. | |
| 2012/0185965 | A1 * | 7/2012 | Senger | C12N 15/8234 435/189 |
| 2012/0185969 | A1 | 7/2012 | DeBrecht et al. | |
| 2019/0292217 | A1 | 9/2019 | Davis et al. | |
| 2019/0292555 | A1 | 9/2019 | Davis et al. | |
| 2021/0070842 | A1 | 3/2021 | Fraser et al. | |

FOREIGN PATENT DOCUMENTS

| | | | |
|---|---|---|---|
| CN | 109679984 | A | 4/2019 |
| CN | 113186147 | A | 7/2021 |
| CN | 114316031 | A * | 4/2022 |
| KR | 101611417 | B1 | 4/2016 |
| WO | WO-9902687 | A1 | 1/1999 |
| WO | WO-03104408 | A2 | 12/2003 |
| WO | WO-2004099405 | A1 | 11/2004 |
| WO | WO-2015038796 | A2 | 3/2015 |
| WO | WO-2021191913 | A1 | 9/2021 |
| WO | WO-2022072846 | A2 * | 4/2022 |
| WO | WO-2024003668 | A1 | 1/2024 |

OTHER PUBLICATIONS

Jaeger, G.D., Scheffer, S., Jacobs, A., Zambre, M., Zobell, O., Goossens, A., Depicker, A. and Angenon, G. (2002) Boosting heterologous protein production in transgenic dicotyledonous seeds using Phaseolus vulgaris regulatory sequences. Nature biotechnology, 20(12), pp. 1265-1268 (Year: 2002).*

Jurgens et al. (2000), Myoglobin: just an oxygen store or also an oxygen transporter?, Physiology, 15(5), 269-274. (Year: 2000).*

"Obesity and Overweight," World Health Organization, (2015), retrieved at https://www.who.int/news-room/fact-sheets/detail/obesity-and-overweight, retrieved on Apr. 12, 2024, 7 pages.

Alexandratos, N, and Bruinsma, J., "World Agriculture Towards 2030/2050: the 2012 Revision," Agricultural Development Economics Division, ESA Working Paper No. 12-03, 1-147, Eldis, United States (2012).

Arun, M., et al., "Transfer and Targeted Overexpression of T-tocopherol Methyltransferase (γ-tmt) Gene Using Seed-specific Promoter Improves Tocopherol Composition in Indian Soybean Cultivars," Applied biochemistry and biotechnology 172(4):1763-1776, Humana Press, United States (Feb. 2014).

Barker, R,F., et al., "Nucleotide Sequence of the T-dna Region From Thea Grobacterium Tumefaciens Octopine Ti Plasmid Pti15955," Plant Molecular Biology 2(6):335-350, Kluwer Academic, United Kingdom (Nov. 1983).

Bhunia, R,K., et al., "Seed-specific Increased Expression of 2s Albumin Promoter of Sesame Qualifies It as a Useful Genetic Tool for Fatty Acid Metabolic Engineering and Related Transgenic Intervention in Sesame and Other Oil Seed Crops," Plant Molecular Biology 86(4-5):351-365, Kluwer Academic, United Kingdom (Nov. 2014).

(Continued)

*Primary Examiner* — Charles Logsdon
*Assistant Examiner* — Jessica Nicole Stockdale
(74) *Attorney, Agent, or Firm* — Sterne, Kessler, Goldstein & Fox P.L.L.C.

(57) ABSTRACT

The present disclosure provides methods of producing heme proteins in transgenic plants, plant tissues, or plant cells, as well as describing the expression of these heme proteins in seeds. Also, the present disclosure provides transgenic plants expressing the heme proteins, myoglobin and hemoglobin, by introducing and integrating the recombinant DNA constructs into the host genetic material of the subject plants. The specific combination of regulatory elements disclosed herein allows for high heme protein expression level in seeds.

26 Claims, 15 Drawing Sheets

Specification includes a Sequence Listing.

(56) References Cited

OTHER PUBLICATIONS

Busconi, M., et al., "Non-food Interventions: Exploring Plant Biotechnology Applications to Therapeutic Protein Production," Applied Plant Genomics and Biotechnology 55-71, Elsevier, Netherlands (Feb. 2015).
Carlsson, M,L,R., et al., "Plant Based Production of Myoglobin—a Novel Source of the Muscle Heme-protein," Scientific Reports 10(1):920, Nature Publishing Group, United Kingdom (Jan. 2020).
Carrington, J.C. and Freed, D.D., "Cap-Independent Enhancement of Translation by a Plant Potyvirus 5' Nontranslated Region," Journal of Virology 64(4):1590-1597, American Society For Microbiology, United States (Apr. 1990).
Chandrasekharan, M,B., et al., "Module-specific Regulation of the Beta-phaseolin Promoter During Embryogenesis," The Plant Journal 33(5):853-866, United Kingdom (Mar. 2003).
Chen, M., et al., "Strong Seed-specific Protein Expression From the Vigna Radiata Storage Protein 8SGα Promoter in Transgenic Arabidopsis Seeds," Journal of Biotechnology 174:49-56, Elsevier, Netherlands (2014).
Chiong, K.T.L., "Tobacco Mosaic Virus As a Gene Editing Platform," Doctoral dissertation, pp. 1-63, Texas A&M University, United States (Aug. 2018).
Coruzzi, G., et al., "Tissue-specific and Light-regulated Expression of a Pea Nuclear Gene Encoding the Small Subunit of Ribulose-1, 5-Bisphosphate Carboxylase," European Molecular Biology Organization 3(8):1671-1679, PMC, United States National Library of Medicine National Institutes of Health, United States (Aug. 1984).
Cunha, N,B., et al., "Accumulation of Functional Recombinant Human Coagulation Factor Ix in Transgenic Soybean Seeds," Transgenic Research 20(4):841-855, Kluwer Academic Publishers, United Kingdom (Aug. 2011).
Cunha, N,B., et al., "Expression of Functional Recombinant Human Growth Hormone in Transgenic Soybean Seeds," Transgenic Research 20(4):811-826, Kluwer Academic Publishers, United Kingdom (Aug. 2011).
De Jaeger, G., et al., "Boosting Heterologous Protein Production in Transgenic Dicotyledonous Seeds Using Phaseolus Vulgaris Regulatory Sequences," Nature Biotechnology 20(12):1265-1268, Nature America Publishing, United States (Nov. 2002).
De Wilde, K., et al., "Recombinant Antibody Production in Arabidopsis Seeds Triggers an Unfolded Protein Response," Plant Physiology 161(2):1-14, Oxford University Press, United Kingdom (Nov. 2012).
Dhaese, P., et al., "Identification of Sequences Involved in the Polyadenylation of Higher Plant Nuclear Transcripts Using Agrobacterium T-DNA Genes as Models," The EMBO journal 2(3):419-426, Nature Publishing Group, United Kingdom (Jan. 1983).
Dhingra, A, and Daniell, H., "Chloroplast Genetic Engineering via Organogenesis or Somatic Embryogenesis," Arabidopsis Protocols pp. 245-262, Springer Science+Business Media, United States (2006).
Diamos, A.G, and Mason, H.S., "Chimeric 3' Flanking Regions Strongly Enhance Gene Expression in Plants," Plant Biotechnology Journal 16:1971-1982, Wiley-Blackwell, United States (Mar. 2018).
Dieryck, W., et al., "Human Haemoglobin From Ransgenic Tobacco," Scientific Correspondence 386:29-30, Springer, Germany (Mar. 1997).
Ding, S.H., et al., "High-level Expression of Basic Fibroblast Growth Factor in Transgenic Soybean Seeds and Characterization of Its Biological Activity," Biotechnology Letters 28(12):869-875, Kluwer Academic Publishers, United Kingdom (Jun. 2006).
Dong, J., "Purification of the Recombinant Green Fluorescent Protein From Tobacco Plants Using Alcohol/salt Aqueous Two-phase System and Hydrophobic Interaction Chromatography," BMC Biotechnology 19(1):1-9, BioMed Central, United Kingdom (Dec. 2019).
El-Mezawy, A., et al., "A Seed Coat-specific Promoter for Canola," Biotechnology Letters 31(12):1961-1965, Kluwer Academic Publishers, United Kingdom (Dec. 2009).
Fischer, R, and Emans, N., "Molecular Farming of Pharmaceutical Proteins," Transgenic Research 9:279-299, Kluwer Academic Publishers, Netherlands (2000).
Fu, Y., et al., "Cloning and identification of the seed specific promoter from soybean," J. Northwest A F Univ. 37(12):1-8, Northwest A&F University, China (Dec. 2009).
Genbank, Accession No. MT559575.1, "Synthetic Construct Left Border T-DNA Sequence," published Jun. 23, 2020, retrieved at https://www.ncbi.nlm.nih.gov/nuccore/MT559575.1/, retrieved on Apr. 12, 2024, 1 Page.
Gong, P., et al., "Molecular Cloning and Functional Characterization of a Seed-specific Vvβvpe Gene Promoter From Vitis Vinifera," Planta 250(2):657-665, Springer, Germany (Aug. 2019).
Goossens, A., et al., "The Arcelin-5 Gene of Phaseolus Vulgaris directs High Seed-specific Expression in Transgenicphaseolus Acutifolius and Arabidopsis Plants1," Plant Physiology 120(4):1095-1104, Oxford University Press, United Kingdom (Aug. 1999).
Halweg, C., et al., "The rb7 Matrix Attachment Region Increases the Likelihood and Magnitude of Transgene Expression in Tobacco Cells: A Flow Cytometric Study," The Plant Cell 17(2):418-429, Oxford University Press, United Kingdom (Feb. 2005).
Hayashi, M., et al., "Genetic Mapping of Cgdef Gene Controlling Accumulation of 7S Globulin (Beta-Conglycinin) Subunits in Soybean Seeds," The Journal of Heredity 100(6):802-806, The American Genetic Association, United States (Nov.-Dec. 2009).
International Search Report and Written Opinion for International Application No. PCT/IB2023/056287, mailed on Nov. 23, 2023, 18 pages.
Ishimoto, M., et al., "Heterologous Expression of Corn Cystatin in Soybean and Effect on Growth of the Stink Bug," Bioscience, Biotechnology, and Biochemistry 76(11):2142-2145, Japan Society for Bioscience, Biotechnology, and Agrochemistry, Japan (Nov. 2012).
Johansson, E., Pea protein-systems for plant based protein products Master's thesis, pp. 1-78, Chalmers University of Technology, Sweden (2019).
Kanagarajan,S., et al., "Production of Functional Human Fetal Hemoglobin in Nicotiana Benthamiana for Development of Hemoglobin-based Oxygen Carriers," International Journal of Biological Macromolecules 184:955-966, Elsevier, Netherlands (Aug. 2021).
Keddie, J.S., et al., "A Seed-specific Brassica Napus Oleosin Promoter Interacts With a G-box-specific Protein and May Be Bi-directional, " Plant Molecular Biology 24(2):327-340, Kluwer Academic, United Kingdom (Jan. 1994).
Keil, M., et al., "Primary Structure of a Proteinase Inhibitor II Gene from Potato (*Solanum tuberosum*)," Nucleic Acids Research 14(14):5641-5650, Oxford University Press, United Kingdom (Jul. 1986).
Lamacchia, C., et al., "Endosperm-specific Activity of a Storage Protein Gene Promoter in Transgenic Wheat Seed," Journal of Experimental Botany 52(355):243-250, Oxford University Press, United Kingdom (Feb. 2001).
Li, G., et al., "Architectural Specificity in Chromatin Structure at the Tata Box in Vivo: Nucleosome Displacement Upon Beta-phaseolin Gene Activation," Proceedings of the National Academy of Sciences of the United States of America 95(8):4772-4777, National Academy of Sciences, United States (Apr. 1998).
Ma, Q., et al., "Expression of Isopentenyl Transferase Gene Controlled by Seed-specific Lectin Promoter in Transgenic Tobacco Influences Seed Development," J Plant Growth Regul 27:68-76, Springer, Germany (2008).
Marzabal, P., et al., "The Bifactorial Endosperm Box of Gamma-zein Gene: Characterisation and Function of the Pb3 and GZM cis-acting Elements," The Plant Journal: for Cell and Molecular Biology 16(1):41-52, Blackwell Scientific Publishers and BIOS Scientific Publishers in association with the Society for Experimental Biology, United Kingdom (Oct. 1998).
Nopo, L., e al., "Super-promoter:TEV, a Powerful Gene Expression System for Tobacco Hairy Roots," Methods in Molecular Biology 824:501-526, Humana Press, United States (2012).
Onwezen, M.C., et al., "A Systematic Review on Consumer Acceptance of Alternative Proteins: Pulses, Algae, Insects, Plant-based

(56) References Cited

OTHER PUBLICATIONS

Meat Alternatives, and Cultured Meat," Appetite 1:159, pp. 1-57, Elsevier, Netherlands (Apr. 2021).
Queiroz, L., et al., "Evaluation of lettuce chloroplast and soybean cotyledon as platforms for production of functional bone morphogenetic protein 2," Trangenic Res 28:213-224, Springer, Germany (Mar. 2019).
Rosenthal, S.H., et al., "An Intronless form of the Tobacco Extensin Gene Terminator Strongly Enhances Transient Gene Expression in Plant Leaves," Plant Molecular Biology 96(4-5):429-443, Kluwer Academic, Netherlands (Mar. 2018).
Shanmugaraj, B., et al., "Plant Molecular Farming: a Viable Platform for Recombinant Biopharmaceutical Production," Plants 9(7):1-19, MDPI, Switzerland (Jul. 2020).
Sheludko, Y.V., "Agrobacterium-mediated Transient Expression as an Approach to Production of Recombinant Proteins in Plants," Recent Patents on Biotechnology 2(3):198-208, Bentham Science Publishers, United Arab Emirates (2008).
Shou, H., et al., "Assessment of Transgenic Maize Events Produced by Particle Bombardment or Agrobacterium-mediated Transformation," Molecular Breeding 13(2):201-208, Springer. Germany (Feb. 2024).
Stehfest, E., et al., "Climate Benefits of Changing Diet," Climatic Change 95:83-102, Springer Science+Business Media, United States (Feb. 2009).
Sunilkumar, G., et al., "Cotton Alpha-globulin Promoter: Isolation and Functional Characterization in Transgenic Cotton, *Arabidopsis*, and Tobacco," Transgenic Research 11(4):347-359, Kluwer Academic Publishers, Netherlands (Aug. 2002).
Sunkara, S., et al., "Isolation and Functional Characterization of a Novel Seed-specific Promoter Region from Peanut," Applied Biochemistry and Biotechnology 172(1):325-339, Humana Press, United States (Jan. 2014).
Tang, G., et al., "Cloning and Functional Characterization of Seed-specific LEC1A Promoter from Peanut (*Arachis hypogaea* L.)," Plos One 16(3):e0242949, pp. 1-17, Public Library of Science, United States (Mar. 2021).
Thanh, V.H., and Shibasaki, K., "Heterogeneity of Beta-conglycinin," Biochimica Et Biophysica Acta 439(2):326-338, Elsevier Publishing company, Netherlands (Aug. 1976).
Tilman, D., and Clark, M., "Global Diets Link Environmental Sustainability and Human Health," Nature 515(7528):518-522, Nature Publishing Group, United kingdom (Nov. 2014).
Tsubokura, Y., et al., "The β-conglycinin Deficiency in Wild Soybean is Associated With the Tail-to-tail Inverted Repeat of the a-subunit Genes," Plant Molecular Biology 78(3):301-309, Kluwer Academic, Netherlands (Feb. 2012).
Vain, P., et al., "Matrix Attachment Regions Increase Transgene Expression Levels and Stability in Transgenic Rice Plants and Their Progeny," The Plant Journal 18(3):233-242, Wiley-Blackwell, United States (1999).
Valin, H., et al., "The Future of Food Demand: Understanding Differences in Global Economic Models," Agricultural Economics 45:1-17, Wiley, United States (Jan. 2014).
Verma, S., and Bhatia, S., "Analysis of Genes Encoding Seed Storage Proteins (SSPs) in Chickpea (*Cicer arietinum* L.) Reveals Co-expressing Transcription Factors and a Seed-specific Promoter," Functional & Integrative Genomics 19(3):373-390, Springer, Germany (May 2019).
Vigeolas, H., et al., "Increasing Seed Oil Content in Oil-seed Rape (*Brassica napus* L.) by Over-expression of a Yeast Glycerol-3-phosphate Dehydrogenase Under the Control of a Seed-specific Promoter," Plant Biotechnology Journal 5(3):431-441, Association of Applied Biologists (May 2007).
Wadahama, H., et al., "Accumulation of β-Conglycinin in Soybean Cotyledon through the Formation of Disulfide Bonds between α'- and α-Subunits," Plant Physiology, 158(3):1395-1405, Oxford University Press, United Kingdom (Jan. 2012).
Yeom, W W., et al., "Increased Production of A-linolenic Acid in Soybean Seeds by Overexpression of Lesquerella FAD3-1," Frontiers in Plant Science 10:1812, 1-14, Frontiers Research Foundation, Switzerland (Jan. 2020).
Zakharov, A., et al., "Seed-specific Promoters Direct Gene Expression in Non-seed Tissue," Journal of Experimental Botany 55(402):1463-1471, Oxford University Press, United Kingdom (Jul. 2004).
Zhang, C., et al., "Production of Meat Alternatives Using Live Cells, Cultures and Plant Proteins," Current Opinion in Food Science 43:1-10, Elsevier, Netherlands (Feb. 2022).

* cited by examiner

5'
TGGCAGGATATATTGTGGTGTAAACAAATTGACGCTTAGACAACTTAATAACACATTGCGGACGTTTTTAATGTACTGAATTAACGCCGAATTGCTCT
AGCATTCGCCATTCAGGCTGCGCAACTGTTGGGAAGGGCGATCGGTGCGGGCCTCTTCGCTATTACGCCAGCTGGCGAAAGGGGGATGTGCTGCAAG
GCGATTAAGTTGGGTAACGCCAGGGTTTTCCCAGTCACGACGTTGTAAAACGACGGCCAGTGCCAAGCTAATTCGCTTCAAGACGTGCTCAAATCACTAT
TTCCACACCCCTATATTTCTATTGCACTCCCTTTTAACTGTTTTTTATTACAAAAATGCCCTGGAAAATGCACTCCCTTTTTGTGTTTGTTTTTTTGTGAAACGATGTT
GTCAGGTAATTTATTTGTCAGTCTACTATGGTGGCCCATTATATTAATAGCAACTGTCGGTCCAATAGACGACGTCGATTTTCTGCATTTGTTTAACCACGTGGATT
TTATGACATTTTATATTAGTTAATTTGTAAAACCTACCCAATTAAAGACCTCATATGTTCTAAAGACTAATACTTAATGATAACAATTTTCTTTTAGTGAA
GAAAGGGATAATTAGTAAATATGGAACAAGGGCAGAAGATTTATTAAAGCCGCGTAAGAGACAACAAGTAGGTACGTGGAGTGTCTTAGGTGACTTACCCACATA
ACATAAAGTGACATTAACAAACATAGCTAATGCTCCTATTTGAATAGTGCATATCAGCATACCTTATTACATATAGATAGGAGCAAACTCTAGCTAGATTGTTGAG
CAGATCTCGGTGACGGGCAGGACCGGACGGGGCGGTACCGGCAGGCTGAAGTCCAGCTGCCAGAAACCCACGTCATGCCAGTTCCCGTGCTTGAAGC
CGGCCGCCCGCAGCATGCCGCGGGGGGCATATCCGAGCGCCTCGTGCATGCGCACGCTCGGGTCGTTGGGCAGCCCGATGACAGCGACCACGCTCTT
GAAGCCCTGTGCCTCCAGGGACTTCAGCAGGTGGGTGTAGAGCGTGGAGCCCAGTCCCGTCCGCTGGTGGCGGGGGGAGACGTACACGGTCGACTCG
GCCGTCCAGTCGTAGGCGTTGCGTGCCTTCCAGGGGCCCGCGTAGGCGATGCCGGCGACCTCGCCGTCCACCTCGGCGACGAGCCAGGGATAGCGCT
CCCGCAGACGGACGAGGTCGTCCGTCCACTCCTGCGGTTCCTGCGGCTCGGTACGGAAGTTGACCGTGCTTGTCTCGATGTAGTGGTTGACGATGGTG
CAGACCGCCGGCATGTCCGCCTCGGTGGCACGGCGGATGTCGGCCGGGCGTCGTTCTGGGCTCATGGTAGATCCCCCGTTCGTAAATGGTGAAAATT
TTCAGAAAATTGCTTTTGCTTTAAAAGAAATGATTTAAATTGCTGCAATAGAAGTAGAATGCTTGATTGCTTGAGATTCGTTTGTTTTGTATAT
GTTGTGTTGAGAATTAATTCTCGAGGTCCTCTCCAAATGAAATGAACTTCCTTATATAGAGGAAGGGTCTTGCGAAGGATAGTGGGATTGTGCGTCAT
CCCTTACGTCAGTGGAGATATCACATCAATCCACTTGCTTTGAAGACGTGGTTGGAACGTCTTCTTTTTCCACGATGCTCCTCGTGGGTGGGGGTCCATCTTTGG
GACCACTGTCGGCAGAGGCATCTTCAACGATGGCCTTTCCTTTATCGCAATGATGGCATTTGTAGGAGCCACCTTCCTTTTCCACTATCTTCACAATAAAGTGACA
GATAGCTGGGCAATGGAATCCGAGGAGGTTTCCGGATATTACCCTTTGTTGAAAAGTCTCAATTGCCCTTTGGTCTTCTGAGACTGTATCTTTGATATTTTTGGAG
TAGACAAGTGTGTCGTGCTCCACCATGTTATCACATCAATCCACTTGCTTTGAAGACGTGGTTGGAACGTCTTCTTTTTCCACGATGCTCCTCGTGGGTGGGGGT
CCATCTTTGGGACCACTGTCGGCAGAGGCATCTTCAACGATGGCCTTTCCTTTATCGCAATGATGGCATTTGTAGGAGCCACCTTCCTTTTCCACTATCTTCACAA
TAAAGTGACAGATAGCTGGGCAATGGAATCCGAGGAGGTTTCCGGATATTACCCTTTGTTGAAAAGTCTCAATTGCCCTTTGGTCTTCTGAGACTGTATCTTTGAT
ATTTTTGGAGTAGACAAGTGTGTCGTGCTCCACCATGTTGACCTGCAGACTAGTCCGATCTAGTAACATAGATGACACCGCGCGCGATAATTTATCCTAGT
TTGCGCGCTATATTTTGTTTTCTATCGCGTATTAAATGTATAATTGCGGGACTCTAATCATAAAAACCCATCTCATAAATAACGTCATGCATTACATGTT
AATTATTACATGCTTAACGTAATTCAACAGAAATTATATGATAATCATCGCAAGACCGGCAACAGGATTCAATCTTAAGAAACTTTATTGCCAAATGT
TTGAACGATCGGGGAAATTGAGCTCGCCCGGGAAAGCTTCAATGATACTTGTGAGCAAGAGCATTTGCTACGCCGGCAACAACCTTCTGAAATG
CAGCCTGCACATTAGGGTTGAAATCATGACCAAGTCTACGGGCTAGGACTACAACAATGACGTTGCCGAGTAGGCGAAAATTTTCAGGGTCG
ACGTGAAGTTGATCACAATGCAACTCAGATAACTTCGCAAAAGTACCTTTCAGGTTGTCCAAATGCTTCAGCCCATCAGAGAATGATTGCAAT
ACTTTCTTTCCATGAGCTTTCACTTTTGGATTTCCCATAACAGCATCTGCATTGGACAAATCACCAAAGCTCTCAAAGAATCTTTGTGTCCAGG
GGTAAACCACAAGGAGCCTCCCAAGTGCCTCTCCACCAACTTCATCAACATTAACTTTTCCCCACAACCCTAACACTGCTTCCTTTTCCTCAG
CACTGAGGTGCACacttcctccacctccagatcctccacctcctgatcctccacctcctgatcctccacctccactCCTATATTTGCTGGTGAGTACAGTTGAGACGTTGGCGAGGAA
CTTGTCCAAACTGGCATGCACAGAAGGATTAAAATCATCTGGATGGTGGGCGGCTAAAGTGACTAACAAACAATGGACAGCAGCTTGAAAT
TTACCGGATCAACTCTCAATTTGTGTGCATGAAGATCAGATAATGCAGAAAGTGCGCCGGGAAGGTCATCCAAGTGCCCAACAGCTTTTGTC
AAAGCATCAGCCACCTTCTGCCCATGTGCCTTCACTTGATCACTTCCATGTGAGAGGTTGAAATGAGGAAAGTAAGTCTTTGTCGTTGGAAAG
CCAAGAAACATACGCTCAAGAGCTTCAGCACCGTGCGCTCCAGCTTGACCACCAACTTTTCCCCAAGCAGCCTTAACATTTGCTTTGTCTGCT
GCCGATAGAACCATGGATCCTCTAGTGGTAGATCCCCCGTTCGTAAATGGTGAAAATTTTCAGAAAATTGCTTTTGCTTTAAAAGAAATGATTTA
AATTGCTGCAATAGAAGTAGAATGCTTGATTGCTTGAGATTCGTTTGTTTTGTATATGTTGTGTTGAGAATTAATTCTCGAGGTCCTCTCCAAAT
GAAATGAACTTCCTTATATAGAGGAAGGGTCTTGCGAAGGATAGTGGGATTGTGCGTCATCCCTTACGTCAGTGGAGATATCACATCAATCCACTTGCTTTG
AAGACGTGGTTGGAACGTCTTCTTTTTCCACGATGCTCCTCGTGGGTGGGGGTCCATCTTTGGGACCACTGTCGGCAGAGGCATCTTCAACGATGGCCTTTCCT
TTATCGCAATGATGGCATTTGTAGGAGCCACCTTCCTTTTCCACTATCTTCACAATAAAGTGACAGATAGCTGGGCAATGGAATCCGAGGAGGTTTCCGGATATTA
CCCTTTGTTGAAAAGTCTCAATTGCCCTTTGGTCTTCTGAGACTGTATCTTTGATATTTTTGGAGTAGACAAGTGTGTCGTGCTCCACCATGTTATCACATCAATCC
ACTTGCTTTGAAGACGTGGTTGGAACGTCTTCTTTTTCCACGATGCTCCTCGTGGGTGGGGGTCCATCTTTGGGACCACTGTCGGCAGAGGCATCTTCAACGAT
GGCCTTTCCTTTATCGCAATGATGGCATTTGTAGGAGCCACCTTCCTTTTCCACTATCTTCACAATAAAGTGACAGATAGCTGGGCAATGGAATCCGAGGAGGTC
TCCGGATATTACCCTTTGTTGAAAAGTCTCAATTGCCCTTTGGTCTTCTGAGACTGTATCTTTGATATTTTTGGAGTAGACAAGTGTGTCGTGCTCCACCATGTTGA
CTCTAGAGAATTCGTAATCATGTCATAGCTGTTTCCTGTGTGAAATTGTTATCCGCTCACAATTCCACACAACATACGAGCCGGAAGCATAAAGTGTA
AAGCCTGGGGTGCCTAATGAGTGAGCTAACTCACATTAATTGCGTTGCGCTCACTGCCCGCTTTCCAGTCGGGAAACCTGTCGTGCCAGCTGCATTAA
TGAATCGGCCAACGCGCGGGGAGAGGCGGTTTGCGTATTGGAGCTTGAGCTTGGATCAGATTGTCGTTTCCCGCCTTCAGTTTAAACTATCAGTGTTTG
ACAGGATATATTGGCGGGTAAAC
3'

FIG. 6

5'
TGGCAGGATATATTGTGGTGTAAACAAATTGACGCTTAGACAACTTAATAACACATTGCGGACGTTTTTAATGTACTGAATTAACGCCGAATTGCTCTAGCATTCG
CCATTCAGGCTGCGCAACTGTTGGGAAGGGCGATCGGTGCGGGCCTCTTCGCTATTACGCCAGCTGGCGAAAGGGGGATGTGCTGCAAGGCGATTAAGTTGGGTA
ACGCCAGGGTTTTCCCAGTCACGACGTTGTAAAACGACGGCCAGTGCCAAGCTAATTCGCTTCAAGACGTGCTCAAATCACTATTTCCACACCCCTATATTTCTATTGCA
CTCCCTTTTAACTGTTTTTTATTACAAAAATGCCCTGGAAAATGCACTCCCTTTTTGTGTTTGTTTTTTTGTGAAACGATGTTGTCAGGTAATTTATTTGTCAGTCTACTATGGTGG
CCCATTATATTAATAGCAACTGTCGGTCCAATAGACGACGTCGATTTTCTGCATTTGTTTAACCACGTGGATTTTATGACATTTTATATTAGTTAATTTGTAAAACCTACCCAATTA
AAGACCTCATATGTTCTAAAGACTAATACTTAATGATAACAATTTTCTTTAGTGAAGAAAGGGATAATTAGTAAATATGGAACAAGGGCAGAAGATTTATTAAAGCCGCGTAAG
AGACAACAAGTAGGTACGTGGAGTGTCTTAGGTGACTTACCCACATAACATAAAGTGACATTAACAAACATAGCTAATGCTCCTATTTGAATAGTGCATATCAGCATACCTTATT
ACATATAGATAGGAGCAAACTCTAGCTAGATTGTTGAGCAGATCTCGGTGACGGGCAGGACCGGACGGGGCGGTACCGGCAGGCTGAAGTCCAGCTGCCAGAAACC
CACGTCATGCCAGTTCCCGTGCTTGAAGCCGGCCGCCCGCAGCATGCCGCGGGGGGCATATCCGAGCGCCTCGTGCATGCGCACGCTCGGGTCGTTGGGCAGCCC
GATGACAGCGACCACGCTCTTGAAGCCCTGTGCCTCCAGGGACTTCAGCAGGTGGGTGTAGAGCGTGGAGCCCAGTCCCGTCCGCTGGTGGCGGGGGGAGACGT
ACACGGTCGACTCGGCCGTCCAGTCGTAGGCGTTGCGTGCCTTCCAGGGGCCCGCGTAGGCGATGCCGGCGACCTCGCCGTCCACCTCGGCGACGAGCCAGGGAT
AGCGCTCCCGCAGACGGACGAGGTCGTCCGTCCACTCCTGCGGTTCCTGCGGCTCGGTACGGAAGTTGACCGTGCTTGTCTCGATGTAGTGGTTGACGATGGTGCA
GACCGCCGGCATGTCCGCCTCGGTGGCACGGCGGATGTCGGCCGGGCGTCGTTCTGGGCTCATGGTAGATCCCCCGTTCGTAAATGGTGAAAATTTTCAGAAAA
TTGCTTTTGCTTTAAAAGAAATGATTTAAATTGCTGCAATAGAAGTAGAATGCTTGATTGCTTGAGATTCGTTTGTTTTGTATATGTTGTGTTGAGAATTA
ATTCTCGAGGTCCTCTCCAAATGAAATGAACTTCCTTATATAGAGGAAGGGTCTTGCGAAGGATAGTGGGATTGTGCGTCATCCCTTACGTCAGTGGAGATATCACAT
CAATCCACTTGCTTTGAAGACGTGGTTGGAACGTCTTCTTTTTCCACGATGCTCCTCGTGGGTGGGGGTCCATCTTTGGGACCACTGTCGGCAGAGGCATCTTCAACGATGG
CCTTTCCTTTATCGCAATGATGGCATTTGTAGGAGCCACCTTCCTTTTCCACTATCTTCACAATAAAGTGACAGATAGCTGGGCAATGGAATCCGAGGAGGTTTCCGGATATTA
CCCTTTGTTGAAAAGTCTCAATTGCCCTTTGGTCTTCTGAGACTGTATCTTTGATATTTTTGGAGTAGACAAGTGTGTCGTGCTCCACCATGTTATCACATCAATCCACTTGCTTT
GAAGACGTGGTTGGAACGTCTTCTTTTTCCACGATGCTCCTCGTGGGTGGGGGTCCATCTTTGGGACCACTGTCGGCAGAGGCATCTTCAACGATGGCCTTTCCTTTATCGC
AATGATGGCATTTGTAGGAGCCACCTTCCTTTTCCACTATCTTCACAATAAAGTGACAGATAGCTGGGCAATGGAATCCGAGGAGGTTTCCGGATATTACCCTTTGTTGAAAAG
TCTCAATTGCCCTTTGGTCTTCTGAGACTGTATCTTTGATATTTTTGGAGTAGACAAGTGTGTCGTGCTCCACCATGTTGACCTGCAGACTAGTCACTATTTTCAGAAGAAG
TTCCCAATAGTAGTCCAAAATTTTTGTAACGAAGGGAGCATAATAGTTACATGCAAAGGAAAACTGCCATTCTTTAGAGGGGATGCTTGTTTAAGAACAAAAAAT
ATATCACTTTCTTTTGTTCCAAGTCATTGCGTATTTTTTTAAAAATATTTGTTCCTTCGTATATTTCGAGCTTCAATCACTTTATGGTTCTTTGTATTCTGGCTTTGCT
GTAAATCGTAGCTAACCTTCTTCCTAGCAGAAATTATTAATACTTGGGATATTTTTTTAGAATCAAGTAAATTACATATTACCACCACATCGAGCTGCTTTTAAATT
CATATTACAGCCATATAGGCTTGATTCATTTTGCAAAATTTCCAGGATATTGACAACGTTAACTTAATAATATCTTGAAATATTAAAGCTATTATGATTAGGGGTGC
AAATGGACCGAGTTGGTGGTGTAAATATATGAGCTCCCATTTTATTTATTGCTCCCATTTTATTTATTTTAGTTTGTGTGACAGATGAACATTATTAGGAGG
AAAGGTATAAGCAGGTTTAACTGTCACAGGGAAGGTGGTTTTGGGAGTCTAAAGCTTCAATGATACTTGTGAGCAAGAGCATTTGCTACGCCGGCAACAACCTT
CTGAAATGCAGCCTGCACATTAGGGTTGAAATCATGACCAAGTCTACGGGCTAGGACTACAACAATGACGTTGCCGAGTAGGCGAAAATTTTCAGGGTCGACGTGAAGTTGA
TCACAATGCAACTCAGATAACTTCGCAAAAGTACCTTTCAGGTTGTCCAAATGCTTCAGCCCATCAGAGAATGATTGCAATACTTTCTTTCCATGAGCTTTCACTTTTGGATTTC
CCATAACAGCATCTGCATTGGACAAATCACCAAAGCTCTCAAAGAATCTTTGTGTCCAGGGGTAAACCACAAGGAGCCTCCCAAGTGCCTCTCCACCAACTTCATCAACATTAA
CTTTTCCCCACAACCCTAACACTGCTTCCTTTTCCTCAGCACTGAGGTGCACacttcctccacctccagatcctccacctcctgatcctccacctcctgatcctccacctccactCCTATATTTGCTGGTGAGTA
CAGTTGAGACGTTGGCGAGGAACTTGTCCAAACTGGCATGCACAGAAGGATTAAAATCATCTGGATGGTGGGCGGCTAAAGTGACTAACAAACAATGGGACAGCAGCTTGAA
ATTTACCGGATCAACTCTCAATTTGTGTGCATGAAGATCAGATAATGCAGAAAGTGCGCCGGGAAGGTCATCCAAGTGCCCAACAGCTTTTGTCAAAGCATCAGCCACCTTCT
GCCCATGTGCCTTCACTTGATCACTTCCATGTGAGAGGTTGAAATGAGGAAAGTAAGTCTTTGTCGTTGGAAAGCCAAGAAACATACGCTCAAGAGCTTCAGCACCGTGCGCT
CCAGCTTGACCACCAACTTTTCCCCAAGCAGCCTTAACATTTGCTTTGTCTGCTGCCGATAGAACCATGGATCCGGCTATCGTTCGTAAATGGTGAAAATTTTCAGAAA
ATTGCTTTTGCTTTAAAAGAAATGATTTAAATTGCTGCAATAGAAGTAGAATGCTTGATTGCTTGAGATTCGTTTGTTTTGTATATGTTGTGTTGAGAATT
GTTGTGTTAGAGAGCTACAATATATAGAGAAAGATCACCGTTTGGCTAGCTTTAAGTGGCTAAGTGTGAACGGGATGAGATTCTCTTTTCTTTTGGCCGTGTTGGT
CACAAGATTGGACGTCGACGTGTTTGAGGCTTGTGAAATTTCCAGAAGCAAAGAAAGGATAAACTTGAGTTAACATGCAATGGGGAGAAAAACAAAGGGTTGGT
GAGTGTGAGGGGTACTTGGCAGCTGAGAACAATGCTTTAGTTGCATGCCATGCAGATTTCATCCGTTTGAAACTCTGTAAAGGACGTGTGGATCGAGTTCGCGTGA
GCAGCTAGCTTGGCTTGGATTTTTGTCTTGCTATCCCTCTACTACATTAATTTCCCTACATGCAACTGTTTCATGACATTTTCGTGTATCTCCCAACTGGCTAGCTCA
TATTAACTAAGGAAAATAGAATTCTAATGGAAAATTTAAATAATAGACTTTCATATTTTATTTGTCCCCCTCAAATTTTTTACATTTCATTTTTTCGATTTTATTCTA
TTTATTTTTTTATTCTTTTTTTAAAAATTGGCATTCTAAACCCTATATATTATATGAAATAATATATTTTTTAACAAACTCTTTATTATTCATCAAAATTATAAATGCA
TGAATGAAGTATTATATAAGAAGTGAAACTTATAAAATTATGTAATTTATAATAAGTTTCAAGTACGCGTGTTCACCAACAAAATCACGTGAAAAATTGAACAAA
AGACGCAAAAGCAAGACCAAGTAGCCTCCTGAGTGATGCGCTTCAACTGTTGCAAACACTAACCTAAACATAGACGGCTTCTAGGGTGCGCAAAGTTGAAATGTG
AGGCACGGTACACAAGTTTTTTTAGGACCGTTGGATATAACACTTAATTAGTTAACGGTGCAAATCTCCAAGATTTTAGAAGTGGAAAAAGTATTGAATAAAAAA
GTATCGCATTTACTGTAGAGCAAACTCTTATTTTAATATTGTTGGGTCACGTGGGTGTGGGCTTCTCGACTCCACCGGATGATGTTTTCAATTTTGATTTCTTTTTT
TCCTAAAGGTTTTCCATTTACATTTATTTTGGTTAGAAAAAAGAATAAGGCTAAATGTCTAAACCAACTTGCATTCGAACCTAGAACTAAAATAATCTACCACCAC
GCCATCATCAACTTTATACTTTTGAAAAGTATTTATAACAATATATATATTTTATCAAACATGCTTAATTGCCTTAAAATAAAATTTATAAATTAGTTGGTAATATT
TTAACAATATTAACGGATTTCTGGTAAAAAAAAATAAAATCATGAATTTCTAAAATTTTAAAATCAAATTTTTTAATGTATAGATTATTTTATCTAGAGAATTCGTA
ATCATGTCATAGCTGTTTCCTGTGTGAAATTGTTATCCGCTCACAATTCCACACAACATACGAGCCGGAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTT
GCGTATTGGAGCTTGAGCTTGGATCAGATTGTCGTTTCCCGCCTTCAGTTTAAACTATCAGTGTTTGACAGGATATATTGGCGGGTAAAC
3'

FIG. 7

5' aataatGCGGCCGC*ATGGTGGAGCACGACACTCTCGTCTACTCCAAGAATATCAAAGATACAGTCTCAGAAGACC*
*AAAGGGCTATTGAGACTTTTCAACAAAGGGTAATATCGGAAACCTCCTCGGATTCCATTGCCCAGCTATCTGT*
*CACTTCATCAAAAGGACAGTAGAAAAGGAAGGTGGCACCTACAAATGCCATCATTGCGATAAAGGAAAGGCTA*
*TCGTTCAAGATGCCTCTGCCGACAGTGGTCCCAAAGATGGACCCCCACCCACGAGGAGCATCGTGGAAAAAG*
*AAGACGTTCCAACCACGTCTTCAAAGCAAGTGGATTGATGTGATAACATGGTGGAGCACGACACTCTCGTCTA*
*CTCCAAGAATATCAAAGATACAGTCTCAGAAGACCAAAGGGCTATTGAGACTTTTCAACAAAGGGTAATATCGG*
*GAAACCTCCTCGGATTCCATTGCCCAGCTATCTGTCACTTCATCAAAAGGACAGTAGAAAAGGAAGGTGGCAC*
*CTACAAATGCCATCATTGCGATAAAGGAAAGGCTATCGTTCAAGATGCCTCTGCCGACAGTGGTCCCAAAGAT*
*GGACCCCCACCCACGAGGAGCATCGTGGAAAAAGAAGACGTTCCAACCACGTCTTCAAAGCAAGTGGATTGA*
*TGTGATATCTCCACTGACGTAAGGGATGACGCACAATCCCACTATCCTTCGCAAGACCTTCCTCTATATAAGGA*
*AGTTCATTTCATTTGGAGAGGACACGCTGAAATCACCAGTCTCTCTCTACAAATCTATCTCT*GAATTAATTCTC
AACACAACATATACAAAACAAACGAATCTCAAGCAATCAAGCATTCTACTTCTATTGCAGCAATTTAA
ATCATTTCTTTTAAAGCAAAAGCAATTTTCTGAAAATTTTCACCATTTACGAACGATAGATGGGGCTA
TCAGATGGTGAATGGCAACTTGTATTGAATGTTTGGGGAAAAGTTGAAGCTGATGTTGCTGGAC
ATGGTCAAGAAGTGTTAATAAGACTCTTCAAAGGCCACCCTGAAACATTAGAGAAGTTTGACAAA
TTCAAGCACCTAAAATCTGAAGATGAAATGAAGGCCTCCGAGGACTTGAAGAAGCATGGAAACA
CTGTCCTGACTGCACTCGGCGGGATCCTCAAAAAGAAAGGTCATCATGAAGCGGAGTTGACACC
ATTGGCTCAGTCTCATGCTACCAAACACAAGATTCCTGTGAAGTATCTTGAGTTTATTAGTGAGG
CCATAATTCAGGTTTTGCAATCAAAACATCCCGGTGATTTTGGTGCAGATGCTCAAGGAGCAATG
AGCAAAGCACTGGAGCTTTTCAGGAATGATATGGCAGCCAAGTACAAGGAACTTGGATTTCAGG
GGTGA*GATCGTTCAAACATTTGGCAATAAAGTTTCTTAAGATTGAATCCTGTTGCCGGTCTTGCGATGATTATC*
*ATATAATTTCTGTTGAATTACGTTAAGCATGTAATAATTAACATGTAATGCATGACGTTATTTATGAGATGGGTTT*
*TTATGATTAGAGTCCCGCAATTATACATTTAATACGCGATAGAAAACAAAATATAGCGCGCAAACTAGGATAAAT*
*TATCGCGCGCGGTGTCATCTATGTTACTAGATC*GGCGGCCGCttatta

5' aaatttGCGGCCGC*GGTACTTGGCAGCTGAGAACAATGCTTTAGTTGCATGCCATGCAGATTTCATCCGTTTGAAACTCTGTAA*
*AGGACGTGTGGATCGAGTTCGCGTGAGCAGCTAGCTTGGCTTGGATTTTTGTCTTGCTATCCCTCTACTACATTAATTTCCC*
*TACATGCAACTGTTTCATGACATTTTCGTGTATCTCCCAACTGGCTAGCTCATATTAACTAAGGAAAATAGAATTCTAATGGA*
*AAATTTAAATAATAGACTTTCATATTTTATTTGTCCCCCTCAAATTTTTTACATTTCATTTTTTCGATTTTATTCTATTTATTTTTTT*
*ATTCTTTTTTTAAAAATTGGCATTCTAAACCCTATATATTATATGAAATAATATATTTTTTAACAAACTCTTTATTATTCATCAAAA*
*TTATAAATGCATGAATGAAGTATTATATAAGAAGTGAAACTTATAAAATTATGTAATTTATAATAAGTTTCAAGTACGCGTGTTC*
*ACCAACAAAATCACGTGAAAAATTGAACAAAAGACGCAAAAGCAAGACCAAGTAGCCTCCTGAGTGATGCGCTTCAACTGTT*
*GCAAACACTAACCTAAACATAGACGGCTTCTAGGGTGCGCAAAGTTGAAATGTGAGGCACGGTACACAAGTTTTTTTAGGA*
*CCGTTGGATATAACACTTAATTAGTTAACGGTGCAAATCTCCAAGATTTTAGAAGTGGAAAAAGTATTGAATAAAAAAGTATC*
*GCATTTACTGTAGAGCAAACTCTTATTTTAATATTGTTGGGTCACGTGGGTGTGGGCTTCTCGACTCCACCGGATGATGTTT*
*TCAATTTTGATTTCTTTTTTTTGCTAAAGGTTTTCCATTTACATTTATTTTGGTTAGAAAAAAGAATAAGGCTAAATGCCTAAAC*
*CAACTTGCATTCGAACCTAGAACTAAAATAATCTACCACCACGCCATCATCAACTTTATACTTTTGAAAAGTATTTATAACAAT*
*ATATATATTTTATCAAACATGCTTAATTGCCTTAAAATAAAATTTATAAATTAGTTGGTAATATTTTAACAATATTAACAAATTTCT*
*GGTAAAAAAATTAAAATCATGAATTTCTAAAATTTTAAAATCAAATTTTTTAATGTATAGGTTATTTTAATTTAATTTATATTGTTA*
*AAAATGGGTTATTACAATTTAATTAATCTCTAATTAAAATATATATGAGGATATTAGTTTTATTCTAATACTATTGTAATTCCCAT*
*TCATATGAATATATATATATGAGATTGTTTGATAAAATAATCTCAATAAATGTTTCAACTATGCAAAGCATAATGAGCATCTAAC*
*TTATTTACAATTTACAATAATAAATCATGATCAAAACAAACATCAACACTAACTCGTTATTAGTATGTTATCAACAAATGTAAAG*
*GTGAAGCTACTCTAGCTTAAGTCAAAGTTAAATTATTCTGATCAGAAACTCTTTGAAAATATACCTAATAAAACTCAAGAAAAT*
*ACACACCTAATATAAACATATGTTGAACATCTTTATACATGTGCATCTTCAAACCCCTATTCATTCCATCTATTGTGTCTCCAA*
*GAAGGAGATCCAACCTATAAGTCATTTCCTCCCATGTACGTCATGTATAGGATCATTACAGTCACAGCCACATGTGTTATATG*
*CAAGGATTTAATTAGTAGTGTAAAAACTTGAGTGGAATCCTTCAAGGATTAGAAAGAGAAACTAAGGTAAATTAAGAGATTTA*
*CTGAATCAATATAAATCTTTTGTTTTTACTCGAGCTTCTATTATACTTGTTTTATCTTAGTTGCTTCTATCTTACTTTCGATGTTT*
*AAATTTTGAGAAAAAAATCCTTTTGTGAAAAACCTTTTTAAAAAGTTGTTTGACGCTACCGTACAGAGCATCCATTTTTAATTT*
*GTGGTCAAATTTGCTTTGTGAAAATCTTCATCTTACAAAAAAAAAACCTTAATTTAAATCTCATCTAACATATT*GAATTAATTC
TCAACACAACATATACAAAACAAACGAATCTCAAGCAATCAAGCATTCTACTTCTATTGCAGCAATTTAAATCATT
TCTTTTAAAGCAAAAGCAATTTTCTGAAAATTTTCACCATTTACGAACGATAGATGGGGCTATCAGATGGTGAAT
GGCAACTTGTATTGAATGTTTGGGGAAAAGTTGAAGCTGATGTTGCTGGACATGGTCAAGAAGTGTTAATAA
GACTCTTCAAAGGCCACCCTGAAACATTAGAGAAGTTTGACAAATTCAAGCACCTAAAATCTGAAGATGAAA
TGAAGGCCTCCGAGGACTTGAAGAAGCATGGAAACACTGTCCTGACTGCACTCGGCGGGATCCTCAAAAAG
AAAGGTCATCATGAAGCGGAGTTGACACCATTGGCTCAGTCTCATGCTACCAAACACAAGATTCCTGTGAAG
TATCTTGAGTTTATTAGTGAGGCCATAATTCAGGTTTTGCAATCAAAACATCCCGGTGATTTTGGTGCAGAT
GCTCAAGGAGCAATGAGCAAAGCACTGGAGCTTTTCAGGAATGATATGGCAGCCAAGTACAAGGAACTTGG
ATTTCAGGGGTGA*TAGACTCCCAAAACCACCTTCCCTGTGACAGTTAAACCCTGCTTATACCTTTCCTCCTAATAATGTTC*
*ATCTGTCACACAAACTAAAATAAATAAAATGGGAGCAATAAATAAAATGGGAGCTCATATATTTACACCACCAACTCGGTCCA*
*TTTGCACCCCTAATCATAATAGCTTTAATATTTCAAGATATTATTAAGTTAACGTTGTCAATATCCTGGAAATTTTGCAAAATGA*
*ATCAAGCCTATATGGCTGTAATATGAATTTAAAAGCAGCTCGATGTGGTGGTAATATGTAATTTACTTGATTCTAAAAAAATAT*
*CCCAAGTATTAATAATTTCTGCTAGGAAGAAGGTTAGCTACGATTTACAGCAAAGCCAGAATACAAAGAACCATAAAGTGATT*
*GAAGCTCGAAATATACGAAGGAACAAATATTTTTAAAAAAATACGCAATGACTTGGAACAAAAGAAAGTGATATATTTTTTTGTT*
*CTTAAACAAGCATCCCCTCTAAAGAATGGCAGTTTTCCTTTGCATGTAACTATTATGCTCCCTTCGTTACAAAAATTTTGGACT*
*ACTATTGGGAACTTCTTCTGAAAATAGTG*GCGGCCGCttaata

5` aaatttGCGGCCGC*CATTGTACTCCCAGTATCATTATAGTGAAAGTTTTGGCTCTCTCGCCGGTGGTTTTTACCTCTATTTAAA*
*GGGGTTTTCCACCTAAAAATTCTGGTATCATTCTCACTTTACTTGTTACTTTAATTTCTCATAATCTTTGGTTGAAATTATCACG*
*CTTCCGCACACGATATCCCTACAAATTTATTATTTGTTAAACATTTTCAAACCGCATAAAATTTTATGAAGTCCCGTCTATCTTT*
*AATGTAGTCTAACATTTTCATATTGAAATATATAATTTACTTAATTTTAGCGTTGGTAGAAAGCATAAAGATTTATTCTTATTCTT*
*CTTCATATAAATGTTTAATATACAATATAAACAAATTCTTTACCTTAAGAAGGATTTCCCATTTTATATTTTAAAAATATATTTAT*
*CAAATATTTTTCAACCACGTAAATCTCATAATAATAAGTTGTTTCAAAAGTAATAAAATTTAACTCCATAATTTTTTTATTCGACT*
*GATCTTAAAGCAACACCCAGTGACACAACTAGCCATTTTTTTCTTTGAATAAAAAAATCCAATTATCATTGTATTTTTTTTATAC*
*AATGAAAATTTCACCAAACAATCATTTGTGGTATTTCTGAAGCAAGTCATGTTATGCAAAATTCTATAATTCCCATTTGACACT*
*ACGGAAGTAACTGAAGATCTGCTTTTACATGCGAGACACATCTTCTAAAGTAATTTTAATAATAGTTACTATATTCAAGATTTC*
*ATATATCAAATACTCAATATTACTTCTAAAAAATTAATTAGATATAATTAAAATATTACTTTTTTAATTTTAAGTTTAATTGTTGAA*
*TTTGTGACTATTGATTTATTATTCTACTATGTTTAAATTGTTTTATAGATAGTTTAAAGTAAATATAAGTAATGTAGTAGAGTGTT*
*AGAGTGTTACCCTAAACCATAAACTATAACATTTATGGTGGACTAATTTTCATATATTTCTTATTGCTTTTACCTTTTCTTGGTA*
*TGTAAGTCCGTAACTAGAATTACAGTGGGTTGCCATGGCACTCTGTGGTCTTTTGGTTCATGCATGGGTCTTGCGCAAGAAA*
*AAGACAAAGAACAAAGAAAAAAGACAAAACAGAGAGACAAAACGCAATCACACAACCAACTCAAATTAGTCACTGGCTGATC*
*AAGATCGCCGCGTCCATGTATGTCTAAATGCCATGCAAAGCAACACGTGCTTAACATGCACTTTAAATGGCTCACCCATCTC*
*AACCCACACACAAACACATTGCCTTTTTCTTCATCATCACCACAACCACCTGTATATATTCATTCTCTTCCGCCACCTCAATTT*
*CTTCACTTCAACACACGTCAACCTGCATATGCGTGTCATCCCATGCCCAAATCTCCATGCATGTTCCAACCACCTTCTCTCTT*
*ATATAATACCTATAAATACCTCTAATATCACTCACTTCTTTCATCATCCATCCATCCAGAGTACTACTACTCTACTACTATAATA*
*CCCCAACCCAACTCATATTCAATACTACTCTACT*ATGGGGCTATCAGATGGTGAATGGCAACTTGTATTGAATGTTTGG
GGAAAAGTTGAAGCTGATGTTGCTGGACATGGTCAAGAAGTGTTAATAAGACTCTTCAAAGGCCACCCTGAAACA
TTAGAGAAGTTTGACAAATTCAAGCACCTAAAATCTGAAGATGAAATGAAGGCCTCCGAGGACTTGAAGAAGCAT
GGAAACACTGTCCTGACTGCACTCGGCGGGATCCTCAAAAAGAAAGGTCATCATGAAGCGGAGTTGACACCATTG
GCTCAGTCTCATGCTACCAAACACAAGATTCCTGTGAAGTATCTTGAGTTTATTAGTGAGGCCATAATTCAGGTTTT
GCAATCAAAACATCCCGGTGATTTTGGTGCAGATGCTCAAGGAGCAATGAGCAAAGCACTGGAGCTTTTCAGGAA
TGATATGGCAGCCAAGTACAAGGAACTTGGATTTCAGGGGTGATAGACTCCCAAAACCACCTTCCCTGTGACAG
TTAAACCCTGCTTATACCTTTCCTCCTAATAATGTTCATCTGTCACACAAACTAAAATAAATAAAATGGGAGC
AATAAATAAAATGGGAGCTCATATATTTACACCACCAACTCGGTCCATTTGCACCCCTAATCATAATAGCTTT
AATATTTCAAGATATTATTAAGTTAACGTTGTCAATATCCTGGAAATTTTGCAAAATGAATCAAGCCTATATG
GCTGTAATATGAATTTAAAAGCAGCTCGATGTGGTGGTAATATGTAATTTACTTGATTCTAAAAAAATATCCC
AAGTATTAATAATTTCTGCTAGGAAGAAGGTTAGCTACGATTTACAGCAAAGCCAGAATACAAAGAACCATA
AAGTGATTGAAGCTCGAAATATACGAAGGAACAAATATTTTTAAAAAAATACGCAATGACTTGGAACAAAAG
AAAGTGATATATTTTTTGTTCTTAAACAAGCATCCCCTCTAAAGAATGGCAGTTTTCCTTTGCATGTAACTAT
TATGCTCCCTTCGTTACAAAAATTTTGGACTACTATTGGGAACTTCTTCTGAAAATAGTGGCGGCCGCttaaat

HIGH EXPRESSION OF ANIMAL HEME PROTEIN IN PLANTS

CROSS REFERENCE TO RELATED APPLICATIONS

This application is a Continuation of PCT/IB2023/056287, filed Jun. 16, 2023, which also claims the priority benefit of U.S. Provisional Application No. 63/367,299, filed Jun. 29, 2022, which are hereby incorporated by reference in their entirety.

REFERENCE TO SEQUENCE LISTING SUBMITTED ELECTRONICALLY

The content of the electronically submitted sequence listing in XML format (Name: 5061_0020002_Seqlisting_ST26.xml; Size: 43,209 bytes; and Date of Creation: Apr. 15, 2024), filed with the application, is incorporated herein by reference in its entirety.

FIELD OF DISCLOSURE

The present disclosure relates to the production of animal heme proteins in transgenic plants. The present disclosure is also related to food compositions comprising recombinant heme proteins produced in genetically engineered plants. The present disclosure also relates to improved expression cassettes for the production of animal heme proteins in transgenic plants and transgenic seeds comprising selected regulatory elements and codon-optimized protein coding sequences which result in substantially high (e.g. >5%, >8%, and >10% total soluble protein [tsp]) expression levels of recombinant proteins in plant seeds.

BACKGROUND

Climate change as well as the expected global population growth to 9.7 billion by 2050 are demanding more sustainable lifestyle practices. Livestock production supplies most of the dietary protein; however, livestock causes about 18% of the global greenhouse gas emissions (Stehfest et al. (2009), Clim. Change 95:83). These greenhouse emissions caused by livestock production are predicted to increase by 80% by 2050 (Tilman & Clark, (2014), Nature 515:518).

Meat production suffers from other problems, such as high resource intake, presence of antibiotic residues in the meat, zoonotic diseases, and ethical concerns related to exploiting animals. Public health issues, such as type 2 diabetes, cardiovascular disease, and cancer, are also associated with meat consumption (Zhang et al. (2022), Curr. Opin. Food Sci. 43:43). Despite these problems, meat has a special status in human diet and continues an unprecedented rise in demand. During the last two decades, there has been a 58% increase in global demand for meat. By 2050, studies project an increase of 62-144% in total meat consumption (Alexandratos & Bruinsma, (2012), Agricultural Development Economics Division; Valin et al (2014), J. Agric. Econ. 45:51).

Proposed mitigation efforts to livestock production and consumption include a shift to a plant-based protein diet. The demand for plant-based protein is on the rise due to its health benefits, environmentally friendly production, animal welfare, as well a consumer taste-based curiosity (Johansson, (2019) Master's thesis Chalmers University of Technology; World Health Organization, (2015). www.who.int/en/news-room/fact-sheets/detail/obesity-and-overweight). A review of 91 articles found that consumer acceptance of plant protein-based meat alternatives is the highest, followed by cultured meat (Onwezen et al. (2021), Appetite, 159:105058). However, production of plant-based meat alternatives still faces some challenges such as the reconstruction of meat-like color, flavor, nutritional-value, and structure (Zhang et al. (2022), Curr. Opin. Food Sci. 43:43).

Genetic engineering represents an expedient strategy for upgrading plant-based recombinant protein products. These recombinant proteins in plants, when used as an ingredient, or used as a whole with the original plant part, can help substitute animal-based protein in the human diet and provide the desired organoleptic properties. Expression of recombinant proteins in plants can help upgrade its color, flavor, nutritional-value, and structure in its native form or when used as an ingredient. The present disclosure provides for a solution to produce critical animal heme proteins at a high expression level in transgenic plants and their seeds.

There have been some previous efforts that expressed plant-derived heme proteins in plants for further production of food products. For example, US patent application publication US2019292555 discloses rice and *Arabidopsis* transgenic plants expressing the soy leghemoglobin Lbc2 under the control of an alcohol inducible promoter. This published patent application does not show any data associated with the expression levels of the recombinant leghemoglobin.

The US patent application publication US2019292217 describes transgenic *Arabidopsis thaliana* plants overexpressing an enzyme involved in the heme biosynthetic pathway (glutamyl-tRNA reductase (GluTR) binding protein) as well as the expression of a soy leghemoglobin. The document does not provide any data about the expression levels of the leghemoglobin.

The international application publication WO2022072846 discloses information, but no experimentation, about transgenic plants expressing a heme protein with altered fatty acid profiles and upregulated heme biosynthesis.

The international application publication WO9902687 discloses a method to increase the content of iron in transgenic rice plants by expressing a rice- or an *Arabidopsis thaliana*-hemoglobin; however, the transgenic plants show a low hemoglobin expression level.

A study discloses the production of human myoglobin in leaves of *Nicotiana benthamiana* (Carlsson et al. (2020), Sci. Rep. 10:1). This document does not show data about heme loading to the recombinant myoglobin nor the functionality or correct structure fold of this recombinant protein nor its incorporation into food products.

However, these attempts to produce heme proteins in plants have not resulted in high levels (e.g., >5% tsp) of recombinant heme protein expression in plant seeds. Molecular farming studies, focused on expressing the gene via nuclear transformation, average expression levels of recombinant proteins of 0.5-2% tsp in stably transformed plants (Fischer & Emans, (2000), Transgenic Res. 9:279; Shanmugaraj et al. (2020), Plants, 9:842). These recombinant proteins produced in plants are mainly pharmaceutical proteins, proteins for diagnostic, research and cosmetic industries. In chloroplasts, researchers have achieved higher yields of recombinant protein expression, with ranges of 3-46% tsp from the plant (Dhingra & Daniell, (2006), *Arabidopsis* protocols, 245; Shanmugaraj et al, (2020), Plants, 9:842). The aforementioned recombinant proteins expressed in chloroplast are mainly pharmaceuticals but also include herbicide resistance genes. In seeds, recombinant proteins accumulate to a lower average concentration (0.05-

1% tsp) (Jaeger et al, (2002). Nat. Biotechnol, 20:1265; Shanmugaraj et al. (2020), Plants, 9:842). However, independent studies have identified regulatory elements that produce significantly higher levels of protein in plant seeds (Jaeger et al. (2002), Nat. Biotechnol. 20:1265; Ishimoto et al. (2012), Biosci. Biotechnol. Biochem. 76:2142; Wadahama et al. (2012), Plant Physiol. 158:1395; Goossens et al. (1999), Plant Physiol. 120:1095; Diamos & Mason, (2018). Plant Biotechnol. J. 16:1971). These studies have reported up to 15-36% tsp in seeds of model species such as *Arabidopsis* and tobacco (Jaeger et al. (2002), Nat. Biotechnol. 20:1265; Goossens et al. (1999), Plant Physiol. 120:1095). However, none of these independent studies are focused on complex proteins such as the heme proteins in the present disclosure and are only validated in model plant species. Combinations of regulatory elements described herein have the potential to result in a stable seed protein production of more than 5%, 8%, or 10% tsp in commercially important seed crops such as legumes.

Therefore, state of the art still has not provided a solution to produce heme proteins at high expression levels in seeds of transgenic plants.

BRIEF SUMMARY

In some aspects, provided herein is a transgenic plant, plant tissue, or plant cell comprising an exogenous nucleic acid encoding for a heme protein. In some aspects, said nucleic acid is operatively linked to a seed-specific promoter and a transcription terminator. In some aspects, said heme protein is expressed in a seed in an amount of at least about 5% total soluble protein (TSP).

In some aspects, said nucleic acid is operatively linked to a transcriptional or translational enhancer.

In some aspects, said heme protein is expressed in the seed in an amount of at least about 8% TSP.

In some aspects, said heme protein is expressed in the seed in an amount of at least about 10% TSP.

In some aspects, said heme protein comprises a plant derived heme protein, a microorganism derived heme protein, or an animal derived heme protein or a synthetic protein designed based on natural heme proteins.

In some aspects, said heme protein comprises heme proteins involved in oxygen transport, enzymes having a prosthetic heme group, or heme proteins involved in the electron transport chain.

In some aspects, said heme protein comprises hemoglobin, myoglobin, neuroglobin, cytoglobin, cytochrome P450s, cytochrome c oxidase, ligninases, catalase, peroxidases, cytochrome a, cytochrome b, or cytochrome c.

In some aspects, said heme protein is an animal derived heme protein selected from the group consisting of hemoglobin and myoglobin.

In some aspects, said seed specific promoter comprises the beta-conglycinin alpha subunit of the 7S storage (7s) promoter from soybean, the beta-phaseolin (Phas) promoter from common bean, USP promoter from *Vicia faba*, SBP promoter from *Vicia faba*, Legumin B4 promoter from *Vicia faba*, Napin promoter from *Brassica napus*, Vicilin promoter from *Pisum sativum*, α-globulin promoter from cotton, γ-zein promoter from maize, glutenin promoter from wheat. VvβVPE promoter from *Vitis* spp, Groundnut seed promoter (GSP) from peanut. 7αP promoter from soybean, AtLAC15 promoter from *Arabidopsis thaliana*, SSPs promoter from chickpea, Lectin promoter from soybean, Oleosin promoter from *Brassica napus*, AhLEC1A promoter from peanut. Glu-ID-1 promoter from wheat, Sesame 2S albumin (2Salb) promoter from sesame, or 8SGα promoter from mung bean.

In some aspects, the transgenic plant, plant tissue, or plant cell further comprises a terminator sequence. In some aspects, the terminator sequence comprises the Extensin terminator from tobacco, Ub10 terminator from *Arabidopsis thaliana*, Hsp70 terminator from *Arabidopsis thaliana*, Hsp18.2 terminator from *Arabidopsis thaliana*, Act2 terminator from *Arabidopsis thaliana*, G7 terminator from *Arabidopsis thaliana,* 3g24240 terminator from *Arabidopsis thaliana*, NOS terminator from *Agrobacterium tumefaciens*, Ocs terminator from *Agrobacterium tumefaciens*, Mas terminator from *Agrobacterium tumefaciens,* 35s terminator from Cauliflower Mosaic Virus, Rbc terminator from *Chrysanthemum*, Ags terminator from *Agrobacterium tumefaciens,* 3' utr-nos terminator from *Agrobacterium tumefaciens,* 7s terminator from soybean. E9 terminator from *Pisum sativum*, ORF25 terminator from *Agrobacterium tumefaciens*, pinII terminator from *Solanum tuberosum*, tml terminator from *Agrobacterium tumefaciens*. Tr7 terminator from *Agrobacterium tumefaciens*, or the Arc5 terminator from *Phaseolus vulgaris.*

In some aspects, the transgenic plant, plant tissue, or plant cell further comprises a transcription or translation enhancer selected from the group consisting of: 5' Untranslated Region (UTR) from Tobacco Etch Virus (TEV) and Rb7Mar 3' Matrix Attachment Region as part of the transcription terminator.

In some aspects, the exogenous nucleic acid is operatively linked to a beta-conglycinin alpha subunit of the 7S storage protein (7s) promoter from soybean, and a NOS terminator.

In some aspects, the exogenous nucleic acid is operatively linked to a beta-conglycinin alpha subunit of the 7S storage protein (7S) promoter from soybean, and an Arc5 terminator and Rb7MAR fused to the Arc5 terminator.

In some aspects, the exogenous nucleic acid is operatively linked to a beta-conglycinin alpha subunit of the 7S storage protein (7S) promoter from soybean, a 5' UTR TEV enhancer and an Arc5 terminator and Rb7MAR fused to arc5.

In some aspects, the exogenous nucleic acid is operatively linked to a beta-phaseolin (Phas) promoter from common bean, and a NOS terminator.

In some aspects, the exogenous nucleic acid is operatively linked to a beta-phaseolin (Phas) promoter from common bean, an Arc5 terminator fused with the Rb7MAR region.

In some aspects, the exogenous nucleic acid is operatively linked to a beta-phaseolin (Phas) promoter from common bean, a 5' UTR TEV enhancer, and an Arc5 terminator fused with the Rb7MAR region.

In some aspects, said nucleic acid encoding for a heme protein comprises a nucleic acid sequence having at least 80% sequence identity to SEQ ID NO: 1. In some aspects, said nucleic acid encoding for a heme protein comprises a nucleic acid sequence having at least 80% sequence identity to SEQ ID NO: 2. In some aspects, said transgenic plant, plant tissue, or plant cell is derived from *Glycine max. Oryza sativa, Hordeum vulgare. Zea mays, Secale cereale. Avena sativa, Beta vulgaris, Beta vulgaris* subsp, *vulgaris, Pastinaca sativa, Phaseolus vulgaris, Pisum sativum, Vigna angularis, Vigna radiata, Cicer arietinum, Arachis hypogaea, Lens culinaris, Medicago sativa. Eruca vesicaria, Brassica juncea. Lactuca sativa, Brassica, Solanum tuberosum, Ipomoea batatas, Manthot esculenta, Triticum aestivum* or *Triticum spelta.*

In some aspects, provided herein is a method to obtain a recombinant heme protein. In some aspects, said method comprises i) providing a transgenic plant capable of expressing at least about 5% TSP of a heme protein in seeds; ii) cultivating said transgenic plant; iii) harvesting said transgenic plant; and iv) isolating and purifying the animal heme protein from said harvested plant.

In some aspects, the harvesting comprising harvesting the seeds of said transgenic plant.

In some aspects, provided herein is a transgenic seed comprising at least about 5% TSP of a recombinant heme protein.

In some aspects, provided herein is a transgenic seed comprising at least about 8% TSP of a recombinant heme protein.

In some aspects, provided herein is a transgenic seed comprising at least about 10% TSP of a recombinant heme protein.

In some aspects, said transgenic seed is from a species selected from the group consisting of *Glycine max, Oryza sativa, Hordeum vulgare. Zea mays, Secale cereale, Avena sativa, Beta vulgaris. Beta vulgaris* subsp. *vulgaris, Pastinaca sativa, Phaseolus vulgaris, Pisum sativum, Vigna angularis. Vigna radiata, Cicer arietinum. Arachis hypogaea, Lens culinaris, Medicago sativa, Eruca vesicaria, Brassica juncea, Lactuca sativa, Brassica, Solanum tuberosum, Ipomoea batatas, Manihot esculenta, Triticum aestivum* and *Triticum spelta.*

In some aspects, said recombinant heme protein is an animal heme protein.

In some aspects, said recombinant heme protein is myoglobin.

In some aspects, said recombinant heme protein is hemoglobin.

In some aspects, provided herein is a food composition comprising any of the transgenic seeds disclosed herein.

In some aspects, provided herein is a food composition comprising the heme protein of any of the plants, plant tissues, or plant cells disclosed herein.

In some aspects, provided here is a meat analogue food composition comprising any of the transgenic seeds disclosed herein.

In some aspects, provided here is a meat analogue food composition comprising the heme protein of any of the plants, plant tissues, or plant cells disclosed herein.

In some aspects, the present disclosure also provides a polynucleotide comprising a nucleic acid encoding for a heme protein, wherein said nucleic acid is operatively linked to a seed-specific promoter selected from the group consisting of beta-conglycinin alpha subunit of the 7S storage (7s) promoter from soybean, the beta-phaseolin (Phas) promoter from common bean, USP promoter from *Vicia faba*. SBP promoter from *Vicia faba*. Legumin B4 promoter from *Vicia faba*, Napin promoter from *Brassica napus*, Vicilin promoter from *Pisum sativum*, α-globulin promoter from cotton, γ-zein promoter from maize, glutenin promoter from wheat, VvβVPE promoter from *Vitis* spp. Groundnut seed promoter (GSP) from peanut, 7αP promoter from soybean, AtLAC15 promoter from *Arabidopsis thaliana*, SSPs promoter from chickpea. Lectin promoter from soybean. Oleosin promoter from *Brassica napus*. AhLEC1A promoter from peanut, Glu-ID-1 promoter from wheat, Sesame 2S albumin (2Salb) promoter from sesame, and 8SGα promoter from mung bean.

In some aspects, said heme protein comprises a plant derived heme protein, a microorganism derived heme protein, or an animal derived heme protein.

In some aspects, said nucleic acid encoding for a heme protein comprises a nucleic acid sequence having at least 80% sequence identity to SEQ ID NO: 1 or SEQ NO: 2.

In some aspects, the polynucleotide comprises a nucleic acid sequence having at least 80% sequence identity to any one of SEQ ID NOs: 3 to 7.

In some aspects, said nucleic acid further comprises a transcription terminator selected from the group consisting of: Extensin terminator from tobacco, Ub10 terminator from *Arabidopsis thaliana*, Hsp70 terminator from *Arabidopsis thaliana*, Hsp18.2 terminator from *Arabidopsis thaliana*, Act2 terminator from *Arabidopsis thaliana*, G7 terminator from *Arabidopsis thaliana,* 3g24240 terminator from *Arabidopsis thaliana*. NOS terminator from *Agrobacterium tumefaciens*, Ocs terminator from *Agrobacterium tumefaciens*, Mas terminator from *Agrobacterium tumefaciens,* 35s terminator from Cauliflower Mosaic Virus, Rbc terminator from *Chrysanthemum*, Ags terminator from *Agrobacterium tumefaciens.* 3' utr-nos terminator from *Agrobacterium tumefaciens.* 7s terminator from soybean, E9 terminator from *Pisum sativum*, ORF25 terminator from *Agrobacterium tumefaciens*, pinII terminator from *Solanum tuberosum*, tml terminator from *Agrobacterium tumefaciens*, Tr7 terminator from *Agrobacterium tumefaciens*, and the Arc5 terminator from *Phaseolus vulgaris.*

In some aspects, said nucleic acid further comprises a transcriptional or translational enhancer selected from the group consisting of 5' UTR TEV and Rb7Mar 3' Matrix Attachment Region.

In some aspects, the present disclosure is directed to an expression vector comprising a nucleic acid encoding for a heme protein, wherein said nucleic acid is operatively linked to a seed-specific promoter selected from the group consisting of beta-conglycinin alpha subunit of the 7S storage (7s) promoter from soybean, the beta-phaseolin (Phas) promoter from common bean. USP promoter from *Vicia faba*, SBP promoter from *Vicia faba*. Legumin B4 promoter from *Vicia faba*, Napin promoter from *Brassica napus*, Vicilin promoter from *Pisum sativum*, α-globulin promoter from cotton, Y-zein promoter from maize, glutenin promoter from wheat, VvβVPE promoter from *Vitis* spp, Groundnut seed promoter (GSP) from peanut, 7αP promoter from soybean, AtLAC15 promoter from *Arabidopsis thaliana*, SSPs promoter from chickpea, Lectin promoter from soybean. Oleosin promoter from *Brassica napus*, AhLEC1A promoter from peanut, Glu-ID-1 promoter from wheat, Sesame 2S albumin (2Salb) promoter from sesame, or 8SGα promoter from mung bean.

In some aspects, the expression vector comprises a heme protein derived from a microorganism, a plant or an animal.

In some aspects, the expression vector comprises a nucleic acid coding for heme protein with a sequence having at least 80% sequence identity to SEQ ID NO: 1.

In some aspects, the expression vector comprises a nucleic acid coding for heme protein with a sequence having at least 80% sequence identity to SEQ ID NO: 2.

In some aspects, the expression vector comprises a nucleic acid coding for heme protein with a sequence having at least 80% sequence identity to SEQ ID NO: 1 operatively linked to a beta-phaseolin (Phas) promoter.

In some aspects, the expression vector comprises a nucleic acid coding for heme protein with a sequence having at least 80% sequence identity to SEQ ID NO: 2 operatively linked to a beta-phaseolin (Phas) promoter. In some aspects, the expression vector, further comprises a transcription terminator selected from the group consisting of: Extensin terminator from tobacco. Ub10 terminator from *Arabidopsis thaliana*, Hsp70 terminator from *Arabidopsis thaliana*, Hsp18.2 terminator from *Arabidopsis thaliana*, Act2 terminator from *Arabidopsis thaliana*, G7 terminator from *Arabidopsis thaliana,* 3g24240 terminator from *Arabidopsis thaliana*, NOS terminator from *Agrobacterium tumefaciens*, Ocs terminator from *Agrobacterium tumefaciens*, Mas terminator from *Agrobacterium tumefaciens.* 35s terminator from Cauliflower Mosaic Virus, Rbc terminator from *Chrysanthemum*, Ags terminator from *Agrobacterium tumefaciens,* 3' utr-nos terminator from *Agrobacterium tumefaciens,* 7s terminator from soybean, E9 terminator from *Pisum sativum*, ORF25 terminator from *Agrobacterium tumefaciens*, pinII terminator from *Solanum tuberosum*, tml terminator from *Agrobacterium tumefaciens*, Tr7 terminator from *Agrobacterium tumefaciens*, and the Arc5 terminator from *Phaseolus vulgaris.*

In some aspects, the expression vector, comprises a nucleic acid coding for heme protein with a sequence having at least 80% sequence identity to SEQ ID NO: 1 operatively linked to a beta-phaseolin (Phas) promoter and Arc5 terminator.

In some aspects, the expression vector, comprises a nucleic acid coding for heme protein with a sequence having at least 80% sequence identity to SEQ ID NO: 2 operatively linked to a beta-phaseolin (Phas) promoter and Arc5 terminator.

In some aspects, the expression vector, further comprises a transcriptional or translational enhancer selected from the group consisting of 5' UTR TEV and Rb7Mar 3' Matrix Attachment Region.

In some aspects, the expression vector, comprises a nucleic acid coding for heme protein with a sequence having at least 80% sequence identity to SEQ ID NO: 1 operatively linked to a beta-phaseolin (Phas) promoter, an Arc5 terminator and a Rb7Mar 3' Matrix Attachment Region.

In some aspects, the expression vector, comprises a nucleic acid coding for heme protein with a sequence having at least 80% sequence identity to SEQ ID NO: 2 operatively linked to a beta-phaseolin (Phas) promoter, an Arc5 terminator and a Rb7Mar 3' Matrix Attachment Region.

In some aspects, the expression vector comprises a nucleic acid sequence having at least 80% sequence identity to any one of SEQ ID NOs: 3 to 7.

BRIEF DESCRIPTION OF THE DRAWINGS

FIG. 6 (FIG. 6) depicts T-DNA nucleotide sequence of pIPTRA0: p35S+HbA-LL-HbB (5' to 3') (4728 bp). Tvsp transcription terminator (italics). Bar gene cDNA, conferring resistance to glufosinate-ammonium, complementary orientation (underlined). Tobacco Etch Virus (TEV) Translational Enhancer, complementary orientation (bolded). CaMV35S-derived double Promoter pr2×35S, complementary orientation (shaded italics). Tnos Transcriptional terminator (shaded underlined). HbA-LL-HbB CDS, complementary orientation (shaded and bolded). Hemoglobin gene consists of the alpha-globin and beta-globin linked via a long linker (LL) (black background with white text) of 63 bp.

FIG. 7 (FIG. 7) depicts T-DNA nucleotide sequence of pIPTRA0: p7S+HbA-LL-HbB-Arc5T (5' to 3') (5649 bp). Tvsp transcription terminator (Italics). Bar gene cDNA, conferring resistance to glufosinate-ammonium, complementary orientation (underlined). Tobacco Etch Virus (TEV) Translational Enhancer, complementary orientation (bolded). CaMV35S-derived double Promoter pr2×35S, complementary orientation (shaded italics). Tobacco Rb7 Matrix Attachment Region, complementary orientation (shaded underline). Arcelin-5 Transcriptional Terminator, complementary orientation (bolded and shaded). HbA-LL-HbB CDS, complementary orientation (black background, white text, italics). Hemoglobin gene consists of the alpha-globin and beta-globin linked via a long linker (LL) (lower case and black background with white text) of 63 bp. Tobacco Etch Virus (TEV) Translational Enhancer, complementary orientation. 7S Globulin Promoter, complementary orientation (black background with white text, underlined).

FIG. 8 (FIG. 8) shows the nucleotide sequence of EC1 linear construct (5' to 3') (1,655 bp). CaMV35S-derived double Promoter 2×35S (italics). Tobacco Etch Virus (TEV) Translational Enhancer (underlined). Myoglobin CDS (bolded). TNOS Transcriptional terminator (shaded italics).

FIG. 9 (FIG. 9) shows the nucleotide sequence of EC2 linear construct (5' to 3') (3.220 bp). 7S globulin (7s) promoter (italics). Tobacco Etch Virus (TEV) Translational Enhancer (underlined). Myoglobin CDS (bolded). ARC5 terminator and Rb7 matrix array region (shaded italics).

FIG. 10 (FIG. 10) shows the nucleotide sequence of EC3 linear construct (5' to 3') (2,623 bp). Phas promoter (italics). Myoglobin CDS (underlined). ARC5 terminator and Rb7 matrix array region (bolded).

FIG. 20A shows expression values for WT, and events transformed with empty vector (1542 event series). EC1 (1545 event series), and EC2 (1544 event series). FIG. 20B shows expression values for events transformed with EC3 (1543 event series) as well as WT and events transformed with empty vector. EC1 and EC2. Myoglobin quantitation from seed extracts was done using the Alpha Diagnostics ELISA kit (cat #600-640-PMY). All samples were normalized to 50 μg/mL total soluble protein (TSP) and tested for myoglobin content according to the manufacturer's protocols. The concentration of myoglobin was determined by reference to the standard curve. Each event consisted of one biological replicate (a pool of 3 seeds) with 3 technical replicates. Standard deviation is presented as error bars for each event.

DETAILED DESCRIPTION

Figure 1:
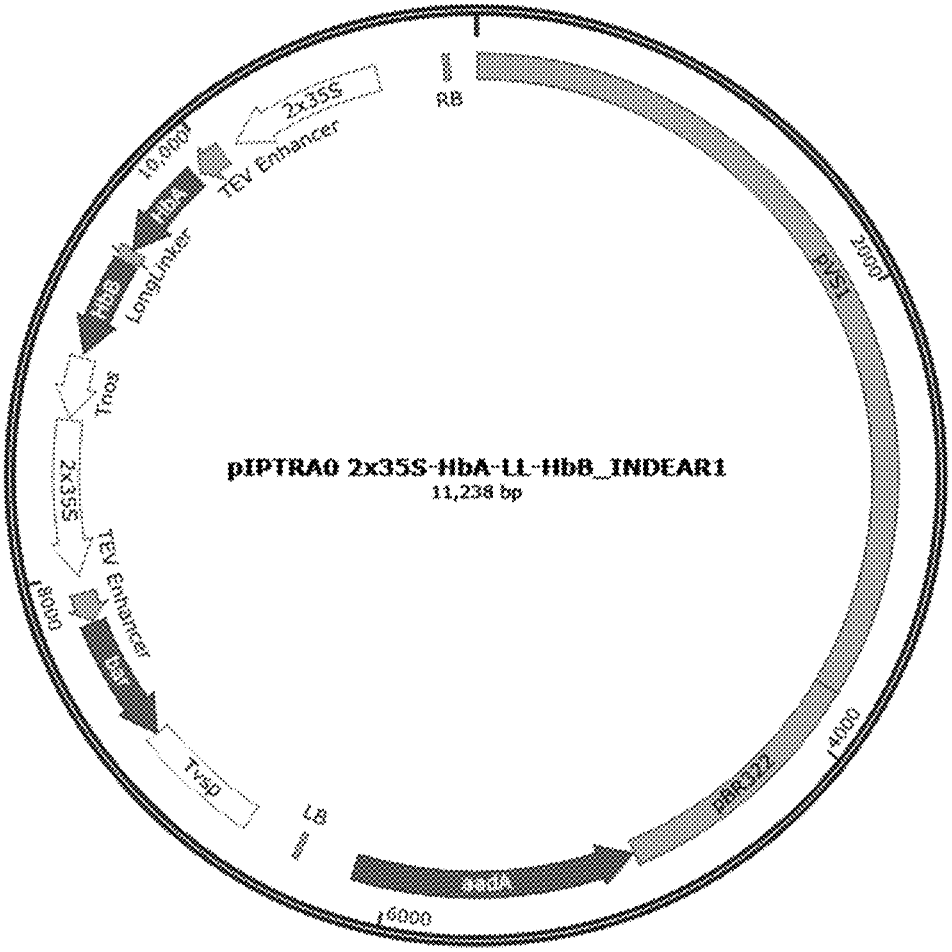
FIG. 1 (FIG. 1) illustrates pIPTRA0: p35S+HbA-LL-HbB binary vector. This plasmid allows the expression of the hemoglobin (HbA-LL-HbB) gene driven by constitutive promoter CaMV35S, and includes the Nopaline synthase terminator (TNOS). The hemoglobin gene consists of the alpha-globin and beta-globin linked via a long linker (LL) of 63 bp. The vector backbone region is 11,238 bp long. The HbA-LL-HbB consists of a soybean codon-optimized sequence.

The terminology used herein is for the purpose of describing particular aspects only and is not intended to be limiting.

It is to be noted that the term "a" or "an" entity refers to one or more of that entity; for example, "a nucleic acid sequence," is understood to represent one or more nucleic acid sequences, unless stated otherwise. As such, the terms "a" (or "an"), "one or more," and "at least one" can be used interchangeably herein.

Furthermore, "and/or", where used herein, is to be taken as specific disclosure of each of the two specified features or components with or without the other. Thus, the term "and/or" as used in a phrase such as "A and/or B" herein is intended to include "A and B." "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures).

Throughout this disclosure, various aspects of this disclosure are presented in a range format. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In some aspects, the production of heme proteins in transgenic plants as well as the use of these heme proteins for alternative meats are discussed herein. In the following description, for purposes of explanation, numerous specific details are set forth in order to provide a thorough understanding of the present invention. It will be evident, however, to one skilled in the art that the present invention may be practiced without these specific details.

The term "derived from," as used herein, refers to a component that is isolated from or made using a specified molecule or organism, or information (e.g., amino acid or nucleic acid sequence) from the specified molecule or organism. For example, a nucleic acid sequence (e.g., an expression vector) that is derived from a second nucleic acid sequence can include a nucleotide sequence that is identical or substantially similar to the nucleotide sequence of the second nucleic acid sequence.

"Nucleic acid," "polynucleotide," and "oligonucleotide," are used interchangeably in the present application. These terms refer only to the primary structure of the molecule. Thus, these terms include double- and single-stranded DNA, as well as double- and single-stranded RNA. The terms "nucleic acid." "polynucleotide." and "oligonucleotide." as used herein, are defined as it is generally understood by the skilled person as a molecule comprising two or more covalently linked nucleotides. Such covalently bound nucleotides can also be referred to as nucleic acid molecules or oligomers.

Polynucleotides can be made recombinantly, enzymatically, or synthetically. e.g., by solid-phase chemical synthesis followed by purification. When referring to a sequence of the polynucleotide or nucleic acid, reference is made to the sequence or order of nucleobase moieties, or modifications thereof, of the covalently linked nucleotides.

As used herein, the term "heme proteins" include proteins that have the ability of binding a heme prosthetic group to their structure. As used herein, the term heme protein also refers to critical components of flesh of an animal and/or animal proteins, and can provide color and taste to plant-based meat products. Myoglobin and hemoglobin, considered heme proteins, are oxygen-binding proteins in animals. Also, as used herein, the term heme protein refers to heme containing proteins, wherein the term containing means the protein is linked through covalent or non-covalent bonds to the protein. As used herein, the term heme protein refers to not only the full-length protein but also fragments or variants thereof.

As used herein the term "animal heme protein" or "animal derived heme protein" refers to heme proteins expressed in animals, but excludes the human derived heme proteins. According to some aspects of the present disclosure, the animal heme proteins comprise heme proteins involved in the oxygen transport, such as hemoglobin, myoglobin, neuroglobin, and cytoglobin; enzymes having a prosthetic heme group, such as cytochrome P450s, cytochrome c oxidase, ligninases, catalase, and peroxidases, as well as heme proteins involved in the electron transport chain, such as cytochrome a, cytochrome b, and cytochrome c.

As used herein, the term "plant derived heme protein", means heme proteins whose genetic source is native from monocot or dicot plants such as *Nicotiana tabacum* or *Nicotiana sylvestris* (tobacco); *Zea mays* (corn), *Arabidopsis thaliana*, a legume such as *Glycine max* (soybean), *Cicer arietinum* (garbanzo or chickpea), *Pisum sativum* (pea), *Phaseolus vulgaris* (common bean) *Vigna unguiculata* (cowpea). *Vigna radiata* (mung beans), *Lupinus albus* (lupin), or *Medicago sativa* (alfalfa), *Brassica napus* (canola); *Triticum* sps. (wheat, including wheat berries, and spelt); *Gossypium hirsutum* (cotton); *Oryza sativa* (rice); Zizania sps. (wild rice); *Helianthus annuus* (sunflower); *Beta vulgaris* (sugarbeet); *Pennisetum glaucum* (pearl millet); *Chenopodium* sp. (*quinoa*); *Sesamum* sp. (sesame); *Linum usitatissimum* (flax); or *Hordeum vulgare* (barley).

As used herein, the term "microorganism derived heme protein", means heme proteins whose genetic source is native from bacteria yeast, fungi such as *Escherichia coli, Bacillus subtilis, Bacillus licheniformis. Bacillus megaterium, Synechocystis* sp., *Aquifex aeolicus, Methylacidiphilum infernorum. Thermophilus* spp, *A. eutrophus, Saccharomyces cerevisiae, Vitreoscilla* sp. *Pichia pastoris. Magnaporthe oryzae. Fusarium graminearum, Aspergillus oryzae, Trichoderma reesei*, Myceliopthera thermophile, *Kluyveromyces lactis*, and *Fusarium oxysporum.*

As used herein, the term "recombinant protein" refers to a protein encoded by a gene (e.g., recombinant DNA) that has been cloned in a system that supports expression of the gene and translation of messenger RNA. Recombinant proteins are foreign proteins produced in expression hosts. Modification of the gene by recombinant DNA technology can lead to expression of a mutant protein.

As used herein, the term "recombinant heme protein" refers to a recombinant protein, where the recombinant protein is codified by foreign cDNA encoding for the heme protein. As used herein, the term "exogenous nucleic acid" means a cDNA coding for the recombinant heme protein; also, the term "exogenous nucleic acid" is used herein interchangeably with "recombinant nucleic acid". The sequences and structure of numerous heme-containing polypeptides are known (Reedy, et al. (2007), Nucleic Acids Res. 6: D307).

The term "plant" includes reference to whole plants, plant organs, plant tissues, and plant cells, and progeny of the same and includes all monocots and dicots. The word plant used herein, also includes seeds, plant progeny, propagules whether sexually or asexually, descendants of these, such as cuttings or seed, as well as pre-harvest and post-harvest tissues and organs.

The term "transgenic plant" or "genetically engineered" means a plant that has been transformed with one or more exogenous nucleic acids (recombinant sequences). The term "transformation" refers to a process by which a recombinant sequence is introduced and expressed in a plant cell. In plant stable transformation, the foreign DNA is fully integrated into the host genome and remains integrated and continues to be expressed in later generations of the plant. In plant transient transformation, the foreign DNA is not integrated into the host genome and it is not expressed in later generations of the plant. Transformation may occur through *Agrobacterium*-inoculation, viral infection, electroporation, heat shock, lipofection, polyethylene glycol treatment, microinjection, silica beads, carbon nanotubes and particle bombardment methods.

In some aspects, the transgenic plant is a soy (*Glycine max*) plant. In some aspects, the genetically engineered plant is selected from the group consisting of: rice (*Oryza sativa*), barley (*Hordeum vulgare*), wheat (*Triticum aestivum*), corn (*Zea mays*), rye (*Secale cereale*), oat (*Avena sativa*), beet (*Beta vulgaris*), sugar beet (*Beta vulgaris* subsp. *vulgaris*), parsnip (*Pastinaca sativa*), bean, leafy vegetable, tuber, and grass. In some aspect, the bean is bean or pinto bean (*Phaseolus vulgaris*), pea (*Pisum sativum*), adzuki (*Vigna angularis*), mung (*Vigna radiata*), chickpea (*Cicer arietinum*), peanut (*Arachis hypogaea*), or lentil (*Lens culinaris*). In some aspects, the leafy vegetable is alfalfa (*Medicago sativa*), arugula (*Eruca vesicaria*), mustard (*Brassica juncea*), lettuce (*Lactuca sativa*), or *Brassica*. In some aspects, the tuber is a potato (*Solanum tuberosum*), a sweet potato (*Ipomoea batatas*), or a cassava (*Manihot esculenta*). In some aspects, the grass is triticale (*Triticum aestivum*) or spelt (*Triticum spelta*).

Illustrative recombinant sequences of the disclosure are provided in FIGS. 1-10. These recombinant sequences are contained within a plant transformation vector. In some aspects, these vectors are introduced into the *Agrobacterium tumefaciens* as circular plasmids. The t-DNA insert from the circular plasmids is introduced into plant cells via *Agrobacterium*-mediated transformation (FIGS. 1-2, 6-7, and SEQ ID NOs. 3-4). In some aspects, these vectors are bombarded into the plant cells as linear constructs (FIGS. 3-5, 8-10, and SEQ ID NOs. 5-7). In some aspects, a recombinant sequence comprises a promoter, an enhancer sequence, a sequence encoding for a heme protein, and a terminator (FIGS. 1, 3, 6, and 8). In some aspects, a recombinant sequence comprises a promoter, an enhancer sequence, a sequence encoding for a heme protein, a terminator, and a matrix attachment region (FIGS. 2, 4, 5, 7, 9, and 10). In some aspects, the heme protein is hemoglobin (FIGS. 1-2, and 6-7). In other aspects, the heme protein is myoglobin (FIGS. 3-5, and 8-10).

In some aspects, the recombinant sequence comprises a sequence named promoter that refers to nucleic acid sequences that promotes initiation of transcription. The promoter may be a constitutive promoter. A constitutive promoter is capable of initiating transcription in plant cells under any circumstances and its activity is not affected by environmental conditions. Some promoters are tissue specific because these promoters preferentially initiate transcription in certain organs. Other promoters are inducible, modulated by external stimuli such as different chemical, biotic and abiotic environmental factors.

Figure 5:
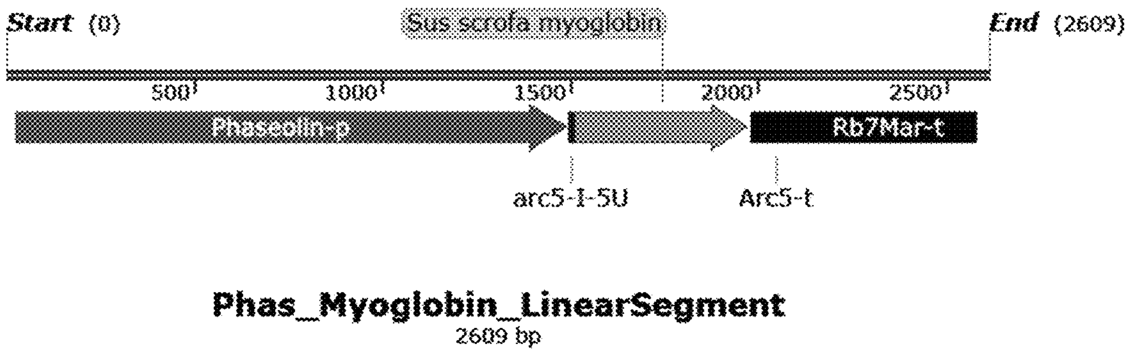
FIG. 5 (FIG. 5) depicts the PPhas+myoglobincDNA+arc5+Rb7MAR linear construct, referred to as EC3. This linear construct allows the expression of the myoglobin gene driven by the phas promoter, in conjunction with the ARC5 terminator and Rb7 matrix array region (MAR). Phas promoter includes the seed specific enhancer (SSE). The linear construct is 2.623 bp long. The myoglobin gene consists of a soybean codon-optimized sequence.

In some aspects, the promoter is a constitutive promoter such as the 35S promoter present as a double unit in tandem (2×35S promoter) (SEQ ID NO: 8) (FIGS. 1, 3, 6, and 8) derived from the cauliflower mosaic virus (CaMV). In some aspects, the promoter is a tissue specific promoter. The tissue specific promoter could be the beta-conglycinin alpha' subunit of the 7S storage protein (7s) promoter from soybean (Zakharov et al. (2004). J. Exp. Bot. 55:1463) (SEQ ID NO: 11), beta-phaseolin (phas) promoter from common bean (Zakharov et al. (2004), J. Exp. Bot. 55:1463), USP promoter from *Vicia faba* (Zakharov et al. (2004), J. Exp. Bot. 55:1463), SBP promoter from *Vicia faba* (Zakharov et al. (2004), J. Exp. Bot. 55:1463), Legumin B4 promoter from *Vicia faba* (Zakharov et al. (2004), J. Exp. Bot. 55:1463), Napin promoter from *Brassica napus* (Vigeolas et al. (2007). Plant Biotechnol. J. 5:431), Vicilin promoter from *Pisum sativum* (Arun et al. (2014). Appl. Biochem. Biotechnol. 172:1763), α-globulin promoter from cotton (Sunilkumar et al. (2002), Transgenic Res. 11:347), γ-zein promoter from maize (Marzábal et al. (1998). Plant J. 16:41). Glutenin promoter from wheat (Lamacchia et al (2001), J. Exp. Bot. 52:243). VvβVPE promoter from *Vitis* spp (Gong et al. (2019). Planta, 250:657), Groundnut seed promoter (GSP) from peanut (Sunkara et al. (2014). Appl Biochem Biotechnol. 172:325), 7αP promoter from soybean (Fu et al. (2009); Northwest Sci. 37:105). AtLAC15 promoter from *Arabidopsis thaliana* (El-Mezawy et al. (2009). Biotechnol. Lett. 31:1961), SSPs promoter from chickpea (Verma & Bhatia, (2019), Funct. Integr. Genomics, 19:373), Lectin promoter from soybean (Ma et al. (2008), J. Plant Growth Regul. 27:68). Oleosin promoter from *Brassica napus* (Keddie et al. (1994) Plant Mol. Biol. 24:327), AhLEC1A promoter from peanut (Tang et al. (2021) PloS one. 16: e0242949), Glu-ID-1 promoter from wheat (Lamacchia et al. (2001). J. Exp. Bot. 52:243), Sesame 2S albumin (2Salb) promoter from sesame (Bhunia et al. (2014), Plant Mol. Biol. 86:351). 8SGα promoter from mung bean (Chen et al. (2014), J. Biotechnol. 174:49). In some aspects, the seed specific promoters are 7S (FIGS. 2, 4, 7, and 9) (SEQ ID NO: 11) and phas (FIGS. 5, and 10). Constructs based on either the 7s or the phas promoters show higher expression of protein in seeds.

The 7s and beta-phaseolin proteins are highly expressed seed storage proteins and their expression patterns have been characterized (Chandrasekharan et al. (2003), Plant J. 33:853; Hayashi et al. (2009). J. Hered. 100:802). The 7S Globulin gene (β-conglycinin) is a major seed-storage protein in soybean (*Glycine max*). This gene consists of three subunits: alpha, alpha', and beta and comprises 30-35% of the total seed protein (Thanh and Shibasaki, (1976), Biochim. Biophys. Acta. 439:326; Hayashi et al. (2009), J. Hered. 100:802). The 7S promoter was inserted in soybean to express a human growth factor and the transgenic lines yielded 2.3% tsp (total soluble protein) for the recombinant protein. 38× higher than the 35S promoter (Ding et al. (2006), Biotechnol. Lett. 28:869). A human bone morphogenetic protein was expressed under the control of the 7s promoter resulting in yields of up to 9.28% tsp (Queiroz et al., 2019, Plant Mol. Biol. 96:429).

The phas gene encodes the major seed storage protein in *Phaseolus vulgaris*. Studies have found that the phas gene is highly expressed in the cotyledons during embryogenesis (Li et al. (1999), PNAS, 95:4772; Chandrasekharan et al. (2003), Plant J. 33:853). This gene is stringently turned off during all vegetative stages of plant development (Li et al. (1999), PNAS, 95:4772). In *Arabidopsis* seeds and under the control of the phas promoter, expression levels of the recombinant protein reached up to 36% of total soluble seed protein (Jaeger et al. (2002), Nat. Biotechnol. 20:1265).

In some aspects, the expression cassette comprises a 2×35S promoter. In some aspects, the 2×35S promoter comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 8.

In some aspects, the 2×35S promoter comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 8.

In some aspects, the expression cassette comprises a 7S promoter. In some aspects, the 7S promoter comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 11.

In some aspects, the 7S promoter comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 11.

In some aspects, the expression cassette comprises a Phas promoter. In some aspects, the Phas promoter comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 14.

In some aspects, the Phas promoter comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 14.

In some aspects, the recombinant sequences comprise a sequence named terminator that refers to nucleic acid sequences that define the end of a gene. Useful terminators include the following, but not limited to. Extensin terminator from tobacco (Rosenthal et al. (2018), Plant Mol. Biol. 96:429), Ub10 terminator from *Arabidopsis thaliana* (Tian et al. 2002, BIO-DES MANUF. 2022:1), Hsp70 terminator from *Arabidopsis thaliana*, (Tian et al. 2002, BIO-DES MANUF. 2022:1), Hsp18.2 terminator from *Arabidopsis thaliana* (Tian et al. 2002, BIO-DES MANUF. 2022:1), Act2 terminator from *Arabidopsis thaliana* (Tian et al. 2002, BIO-DES MANUF. 2022:1), G7 terminator from *Arabidopsis thaliana* (Tian et al. 2002, BIO-DES MANUF. 2022:1), 3g24240 terminator from *Arabidopsis thaliana* (Tian et al. 2002. BIO-DES MANUF. 2022:1), NOS terminator from *Agrobacterium tumefaciens* (Tian et al. 2002. BIO-DES MANUF. 2022:1) (SEQ ID NO: 10), Ocs terminator from *Agrobacterium tumefaciens* (Tian et al. 2002, BIO-DES MANUF. 2022:1), Mas terminator from *Agrobacterium tumefaciens* (Tian et al. 2002, BIO-DES MANUF. 2022:1), 35s terminator from Cauliflower Mosaic Virus (Tian et al. 2002, BIO-DES MANUF. 2022:1), Rbc terminator from *Chrysanthemum* (Tian et al. 2002, BIO-DES MANUF. 2022:1), Ags terminator from *Agrobacterium tumefaciens* (Tian et al. 2002, BIO-DES MANUF. 2022:1), 3' utr-nos terminator from *Agrobacterium tumefaciens* (Tian et al. 2002, BIO-DES MANUF. 2022:1), 7s terminator from soybean (Tsubokura et al. (2012), Plant Mol. Biol. 78:301), E9 terminator from *Pisum sativum* (Coruzzi et al. (1984), EMBO Rep. 3:1671), ORF25 terminator from *Agrobacterium tumefaciens* (Barker et al. (1983), Plant Mol. Biol. 2:335), pinII terminator from *Solanum tuberosum* (Keil et al.

(1986), Nucleic Acids Res. 14:5641), tml terminator from *Agrobacterium tumefaciens* (Barker et al. (1983), Plant Mol Biol. 2:335), Tr7 terminator from *Agrobacterium tumefaciens* (Dhaese et al. (1983). EMBO Rep. 2:419). In some aspects, the terminators are NOS (FIGS. 1, 3, 6, 8) (SEQ ID NO: 10) or arc5 (FIGS. 2, 4, 5, 7, 9, 10) (SEQ ID NO: 12). Arc5 terminator, from *Phaseolus vulgaris*, provides sequences to terminate transcription and to direct polyadenylation of the mRNA (Goossens et al. (1999), Plant Physiol. 120:1095) but is also reported to enhance gene expression and contribute to seed specific expression.

In some aspects, the expression cassette comprises an NOS terminator sequence. In some aspects, the NOS terminator comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 10.

In some aspects, the NOS terminator comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 10.

In some aspects, the expression cassette comprises an arc5 terminator sequence. In some aspects, the arc5 terminator comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 12.

In some aspects, the arc5 terminator comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 12.

In some aspects, the recombinant sequence comprises a translational or transcriptional enhancer sequence. An example of a translation enhancer is the 5' UTR TEV (Tobacco Etch Virus Translational Enhancer) (SEQ ID NO: 9). The 5' leader of the tobacco etch virus (TEV) is one of the better-studied potyvirus translational enhancers, it contains two cap-independent regulatory elements (CIREs) that fold into pseudoknots, which can independently enhance translation of the downstream transgene (Carrington & Freed. (1993) J. Virol., 64:1590). In some aspects, the recombinant sequences include a matrix attached region (MAR) as enhancers. The Rb7 MAR (SEQ ID NO: 13) is a DNA element shown to increase transgene expression in plants. The addition of the Rb7 MAR has been shown to strongly enhance protein production when added to most transcriptional terminators (Diamos & Mason, (2018), Plant Biotechnol. J. 16:1971). Furthermore, MARs can further improve the stability of transgene expression levels and may confer protection against transgene silencing (Vain et al. (1999), Plant J. 18:233). In some aspects, the arc5 terminator is fused to the Rb7 Matrix Attachment Region (MAR) that increases the likelihood and magnitude of transgene expression.

In some aspects, the expression cassette comprises a Rb7MAR enhancer. In some aspects, the Rb7MAR enhancer comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 13.

In some aspects, the Rb7MAR enhancer comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 13.

In some aspects, the expression cassette comprises a TEV enhancer. In some aspects, the TEV enhancer comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 9.

In some aspects, the TEV enhancer comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 9.

In some aspects, specific combinations of regulatory elements (i.e. promoters, terminators, and enhancers), lead to an enhanced expression of the heme protein in seeds above, e.g., 5%, 8%, and 10% tsp. In some aspects, the expression cassette comprises a seed-specific promoter such the 7S or phas, and a terminator such arc5 fused to the Rb7MAR enhancer. In some aspects, the combinations identified herein are:

i. p7S+cDNAHP+arc5+Rb7MAR
ii. p7S+TEV+cDNAHP+arc5+Rb7MAR
iii. PPhas+TEV+cDNAHP+arc5+Rb7MAR
iv. PPhas+cDNAHP+arc5+Rb7MAR The cDNAHP identifies the cDNA for the heme protein. In some aspects, the heme proteins are animal derived heme proteins. In some aspects, the heme proteins are derived from metazoan. In some aspects, the heme proteins are derived from red meat (e.g., beef, pork, goat, and lamb), poultry (e.g., chicken and turkey), and seafood (e.g., fish, crustaceans, and mollusks). In some aspects, the animal derived heme protein is a myoglobin. In some aspects, the animal derived heme protein is a hemoglobin. It is routine for a person skilled in the art to replace orthologous sequences from other organisms, so the mere replacement of the recombinant protein is also in the scope of this disclosure.

In some aspects, the present disclosure also provides a polynucleotide comprising a nucleic acid encoding for a heme protein, wherein said nucleic acid is operatively linked to a seed-specific promoter selected from the group consisting of beta-conglycinin alpha subunit of the 7S storage (7s) promoter from soybean, the beta-phaseolin (Phas) promoter from common bean, USP promoter from *Vicia faba*, SBP promoter from *Vicia faba*. Legumin B4 promoter from *Vicia faba*, Napin promoter from *Brassica napus*, Vicilin promoter from *Pisum sativum*, α-globulin promoter from cotton, γ-zein promoter from maize, glutenin promoter from wheat, VvβVPE promoter from *Vitis* spp. Groundnut seed promoter (GSP) from peanut, 7αP promoter from soybean, AtLAC15 promoter from *Arabidopsis thaliana*. SSPs promoter from chickpea. Lectin promoter from soybean. Oleosin promoter from *Brassica napus*. AhLEC1A promoter from peanut, Glu-ID-1 promoter from wheat, Sesame 2S albumin (2Salb) promoter from sesame, and 8SGα promoter from mung bean.

In some aspects, said heme protein comprises a plant derived heme protein, a microorganism derived heme protein, or an animal derived heme protein.

In some aspects, said nucleic acid encoding for a heme protein comprises a nucleic acid sequence having at least 80% sequence identity to SEQ ID NO: 1 or SEQ NO: 2.

In some aspects, the polynucleotide comprises a nucleic acid sequence having at least 80% sequence identity to any one of SEQ ID NOs: 3 to 7.

In some aspects, said nucleic acid further comprises a transcription terminator selected from the group consisting of: Extensin terminator from tobacco, Ub10 terminator from *Arabidopsis thaliana*, Hsp70 terminator from *Arabidopsis thaliana*, Hsp18.2 terminator from *Arabidopsis thaliana*, Act2 terminator from *Arabidopsis thaliana*, G7 terminator from *Arabidopsis thaliana,* 3g24240 terminator from *Arabidopsis thaliana*. NOS terminator from *Agrobacterium tumefaciens*, Ocs terminator from *Agrobacterium tumefaciens*, Mas terminator from *Agrobacterium tumefaciens,* 35s terminator from Cauliflower Mosaic Virus, Rbc terminator from *Chrysanthemum*, Ags terminator from *Agrobacterium tumefaciens,* 3' utr-nos terminator from *Agrobacterium tumefaciens,* 7s terminator from soybean, E9 terminator from *Pisum sativum*, ORF25 terminator from *Agrobacterium tumefaciens*, pinII terminator from *Solanum tuberosum*, tml terminator from *Agrobacterium tumefaciens*, Tr7 terminator from *Agrobacterium tumefaciens*, and the Arc5 terminator from *Phaseolus vulgaris.*

In some aspects, said nucleic acid further comprises a transcriptional or translational enhancer selected from the group consisting of 5' UTR TEV and Rb7Mar 3' Matrix Attachment Region.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 1.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 1.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 2.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 2.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 3.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 3.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 4.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 4.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 5.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 5.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 6.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 6.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 7.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 7.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 8.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 8.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 9.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 9.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 10.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 10.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 11.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 11.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 12.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 12.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 13.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 13.

In some aspects, the polynucleotide comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 14.

In some aspects, the polynucleotide comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 14.

In some aspects, a plant is transformed with each of the expression cassettes (FIGS. 1-10). In some aspects, a stably transformed plant comprises in its genome: a recombinant DNA construct, wherein the heme protein is stably expressed and produces a pink color in the seed cotyledons and seed protein extracts (FIGS. 15A-15C and 16A-16C). The presence of heme proteins in transgenic organisms has resulted in visual color changes in protein extracts (pink color) when compared to WT (Carlsson et al. (2020). Sci. Rep. 10:1).

Figure 19:
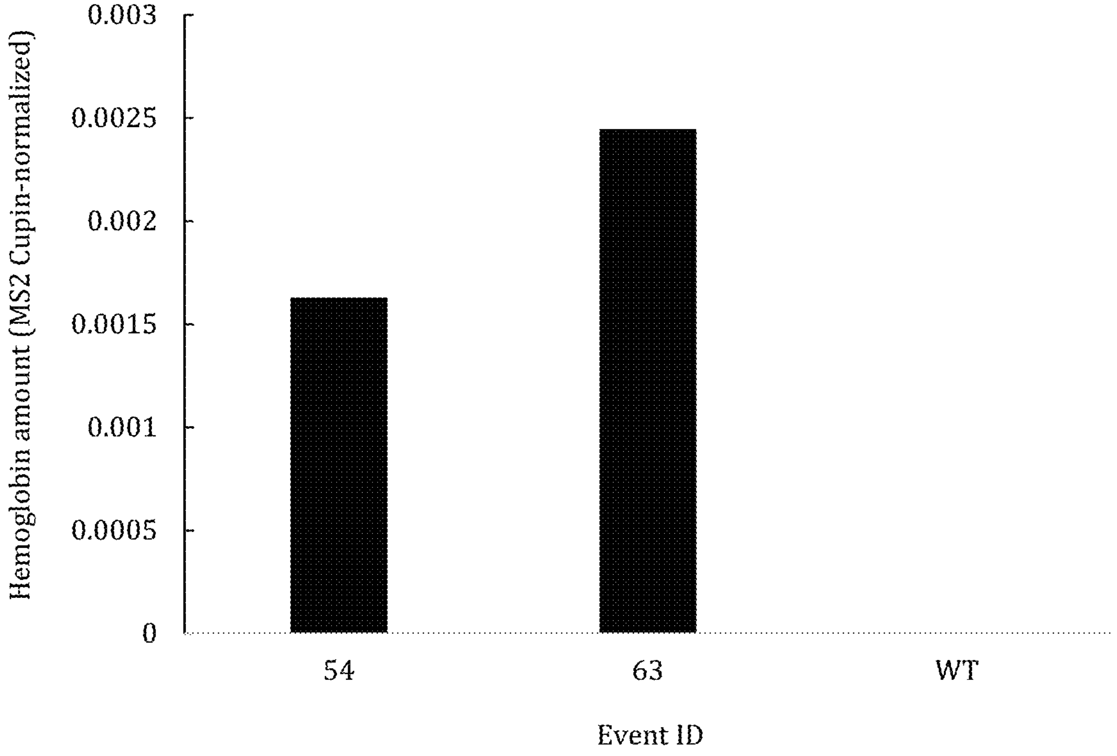
FIG. 19 (FIG. 19) shows the results from porcine hemoglobin identification and quantification from whole soybean seed protein extracts via Liquid chromatography-mass spectrometry (LC-MS). Normalized pig hemoglobin levels are shown in the graph for WT (Wild type) as well as events 54 and 63 (both transformed with pIPTRA0: p7S+HbA-LL-HbB-Arc5T). No hemoglobin was detected in the WT sample. No replicates were run.
Figure 20A:
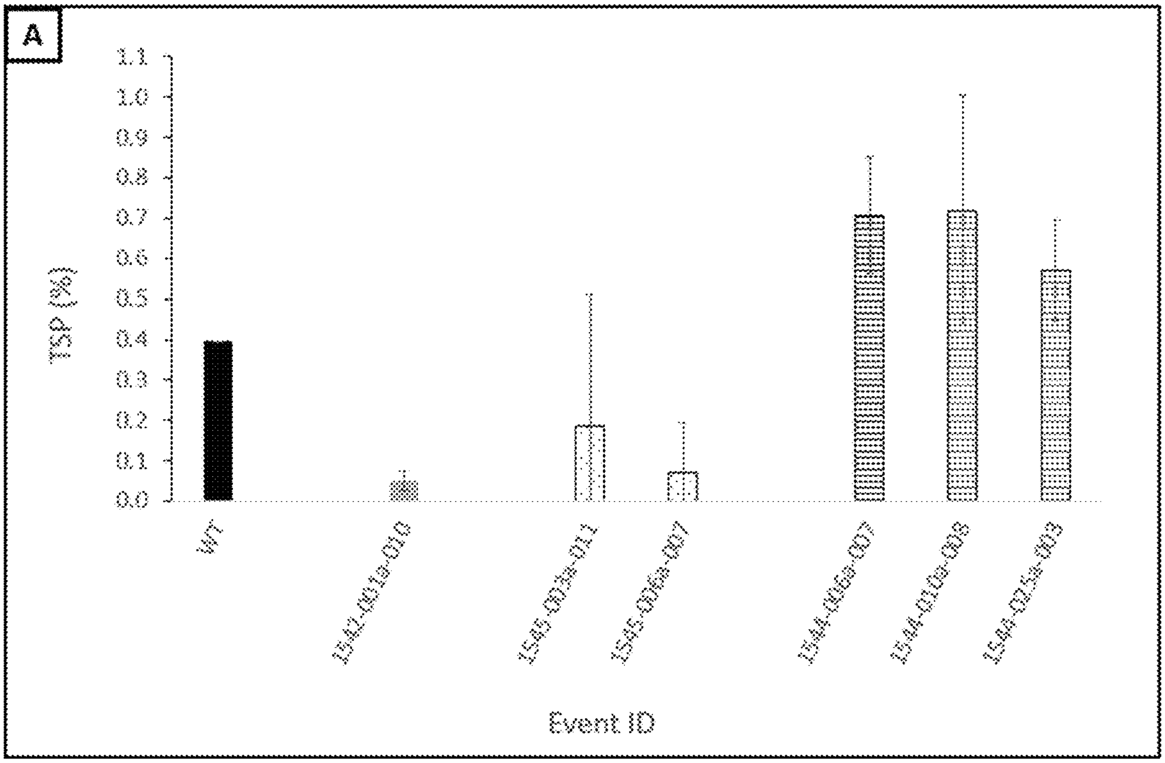
FIGS. 20A-20B (FIGS. 20A-20B) show myoglobin expression levels in soybean transgenic events. Total soluble protein (% TSP), represented in the Y axis, was obtained via ELISA quantitative analysis.

In some aspects, a stably transformed plant comprises in its genome: a recombinant DNA construct, wherein the heme protein is stably expressed, extracted via standard protein extractions protocols, and detected via Western Blot (FIGS. 17A-17C, 18). Liquid chromatography-mass spectrometry (LC-MS) (FIG. 19), and/or ELISA assays (FIGS. 20A-20B).

Figure 20B:
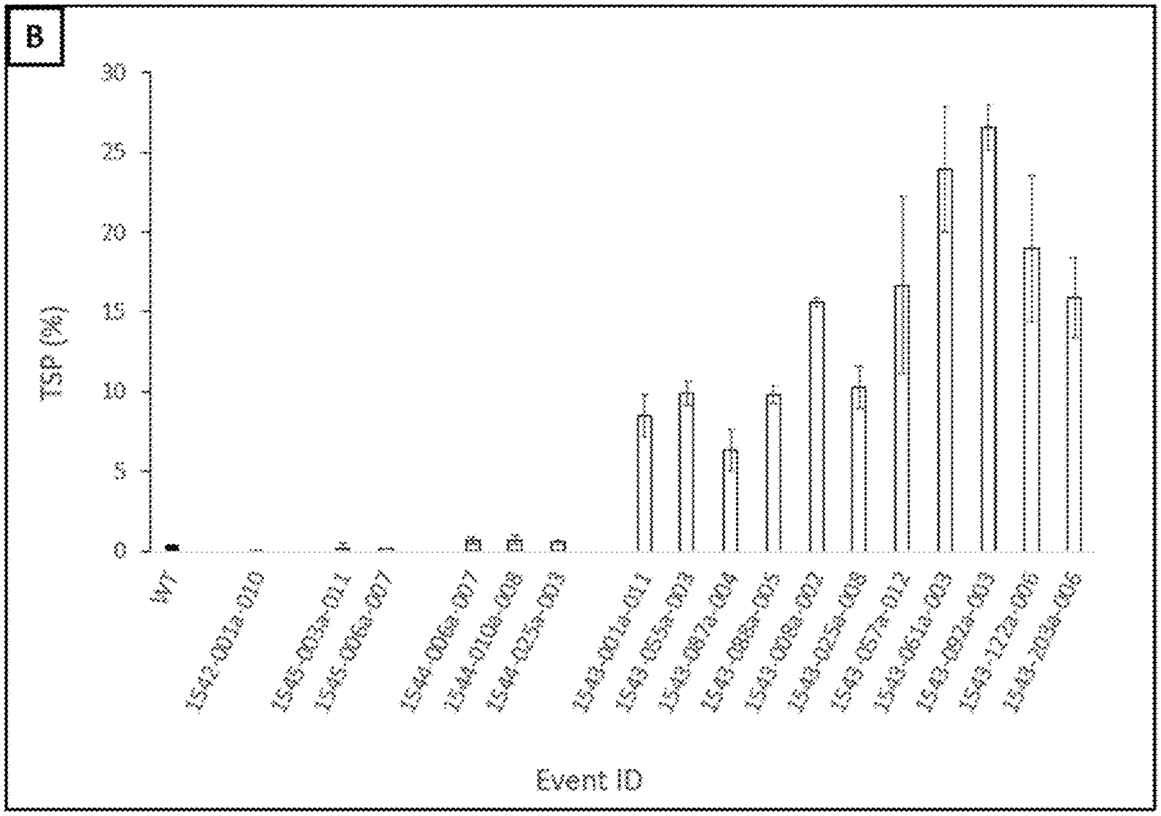

In some aspects, a stably transformed plant comprises in its genome: a recombinant DNA construct, wherein the heme protein is stably expressed in an amount of about 5% tsp or higher (FIG. 20B). In some aspects, the heme protein is stably expressed in an amount of about 8% tsp or higher (FIG. 20B). In some aspects, the heme protein is stably expressed in an amount of about 10% tsp or higher (FIG. 20B). In some aspects, the heme protein is stably expressed in an amount of about 25% or higher (FIG. 20B).

In some aspects, the recombinant heme proteins used for transformation are hemoglobin and myoglobin. In some aspects, the hemoglobin described herein is isolated from pig (*Sus scrofa*). In some aspects, the hemoglobin is a recombinant HbA-LL-HbB and it comprises the hemoglobin A subunit, a long linker, and the hemoglobin B subunit. In some aspects, the myoglobin described herein is isolated from pig (*Sus scrofa domesticus*). In some aspects, the expression cassette comprises any of the sequences disclosed in Table 1.

In some aspects, the expression cassette comprises SEQ ID NO: 11, SEQ ID NO: 12, and/or SEQ ID NO: 13. In some aspects, the expression cassette comprises SEQ ID NO: 11, SEQ ID NO: 9, SEQ ID NO: 12, and/or SEQ ID NO: 13. In some aspects, the expression cassette comprises SEQ ID NO: 14, SEQ ID NO: 9, SEQ ID NO: 12, and SEQ ID NO: 13. In some aspects, the expression cassette comprises SEQ ID NO: 14, SEQ ID NO: 12, and SEQ ID NO: 13.

In some aspects, the expression cassette comprises SEQ ID NO: 11, SEQ ID NO: 1, SEQ ID NO: 12, and/or SEQ ID NO: 13. In some aspects, the expression cassette comprises SEQ ID NO: 11, SEQ ID NO: 9, SEQ ID NO: 1, SEQ ID NO: 12, and/or SEQ ID NO. 13. In some aspects, the expression cassette comprises SEQ ID NO: 14, SEQ ID NO: 9. SEQ ID NO: 1, SEQ ID NO: 12, and SEQ ID NO: 13. In some aspects, the expression cassette comprises SEQ ID NO: 14, SEQ ID NO: 1, SEQ ID NO: 12, and SEQ ID NO: 13.

In some aspects, the expression cassette comprises SEQ ID NO: 11, SEQ ID NO: 2. SEQ ID NO: 12, and/or SEQ ID NO: 13. In some aspects, the expression cassette comprises SEQ ID NO: 11, SEQ ID NO: 9, SEQ ID NO: 2, SEQ ID NO: 12, and/or SEQ ID NO: 13. In some aspects, the expression cassette comprises SEQ ID NO: 14, SEQ ID NO: 9. SEQ ID NO: 2, SEQ ID NO: 12, and SEQ ID NO: 13. In some aspects, the expression cassette comprises SEQ ID NO: 14, SEQ ID NO: 2, SEQ ID NO: 12, and SEQ ID NO: 13.

In some aspects, provided herein is a transgenic plant, plant tissue, or plant cell comprising an expression cassette comprising an exogenous nucleic acid encoding for a heme protein. In some aspects, said nucleic acid is operatively linked to a seed-specific promoter and a transcription terminator. In some aspects, said heme protein is expressed in a seed in an amount of about 5% TSP. In some aspects, said heme protein is expressed in a seed in an amount of about 6% TSP. In some aspects, said heme protein is expressed in a seed in an amount of about 7% TSP. In some aspects, said heme protein is expressed in a seed in an amount of about 8% TSP. In some aspects, said heme protein is expressed in a seed in an amount of about 9% TSP. In some aspects, said heme protein is expressed in a seed in an amount of about 10% TSP. In some aspects, said heme protein is expressed in a seed in an amount of about 11% TSP. In some aspects, said heme protein is expressed in a seed in an amount of about 12% TSP. In some aspects, said heme protein is expressed in a seed in an amount of about 13% TSP. In some aspects, said heme protein is expressed in a seed in an amount of about 14% TSP. In some aspects, said heme protein is expressed in a seed in an amount of about 15% TSP. In some aspects, said heme protein is expressed in a seed in an amount of about 18% TSP. In some aspects, said heme protein is expressed in a seed in an amount of about 20% TSP. In some aspects, said heme protein is expressed in a seed in an amount of about 25% TSP. In some aspects, said heme protein is expressed in a seed in an amount of about 30% TSP. In some aspects, said heme protein is expressed in a seed in an amount between about 5% TSP and about 35% TSP. In some aspects, said heme protein is expressed in a seed in an amount between about 8% TSP and about 35% TSP. In some aspects, said heme protein is expressed in a seed in an amount between about 10% TSP and about 35% TSP. In some aspects, said heme protein is expressed in a seed in an amount between about 12% TSP and about 35% TSP. In some aspects, said heme protein is expressed in a seed in an amount between about 5% TSP and about 30% TSP. In some aspects, said heme protein is expressed in a seed in an amount between about 5% TSP and about 29% TSP. In some aspects, said heme protein is expressed in a seed in an amount between about 5% TSP and about 28% TSP. In some aspects, said heme protein is expressed in a seed in an amount between about 10% TSP and about 30% TSP. In some aspects, said heme protein is expressed in a seed in an amount between about 8% TSP and about 30% TSP. In some aspects, said heme protein is expressed in a seed in an amount between about 6% TSP and about 28% TSP.

In some aspects, the expression cassette comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 3.

In some aspects, the expression cassette comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 4.

In some aspects, the expression cassette comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 5.

In some aspects, the expression cassette comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to SEQ ID NO: 6.

In some aspects, the expression cassette comprises a nucleic acid sequence having at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to SEQ ID NO: 7.

In some aspects, the expression cassette comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 3.

In some aspects, the expression cassette comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 4.

In some aspects, the expression cassette comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 5.

In some aspects, the expression cassette comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 6.

In some aspects, the expression cassette comprises a nucleic acid sequence having about 80%, about 85%, about 90%, about 91%, about 92%, about 93%, about 94%, about 95%, about 96%, about 97%, about 98%, about 99%, or 100% sequence identity to SEQ ID NO: 7.

In some aspects, a stably transformed plant is soybean. Codon optimization is a process used to improve gene expression and increase translational efficiency of a gene of interest by accommodating codon bias of the host organism. In some aspects, the hemoglobin gene has been codon optimized for expression in soybean (SEQ ID NO: 1). In some aspects, the myoglobin gene has been codon optimized for expression in soybean (SEQ ID NO: 2).

In some aspects, the hemoglobin cDNA comprises a nucleic acid sequence having at least 70%, at least 75%, at least 80%, at least 85%, at least 90%, at least 95%, or at least 98% sequence identity to SEQ ID NO: 1.

In some aspects, the myoglobin cDNA comprises a nucleic acid sequence having at least 70%, at least 75%, at least 80%, at least 85%, at least 90%, at least 95%, or at least 98% sequence identity to SEQ ID NO: 2.

In some aspects, the hemoglobin cDNA comprises a nucleic acid sequence having about 70%, about 75%, about 80%, about 85%, about 90%, about 95%, or about 98% sequence identity to SEQ ID NO: 1.

In some aspects, the myoglobin cDNA comprises a nucleic acid sequence having about 70%, about 75%, about 80%, about 85%, about 90%, about 95%, about 98% sequence identity to SEQ ID NO: 2.

In some aspects, the recombinant sequences comprise a gene encoding for a selectable marker. In some aspects, the selectable marker is the BAR gene which produces the phosphinothricin N-acetyltransferase protein and provides resistance to gluphosinate. In some aspects, the BAR gene is located in the same plant transformation vector (circular plasmid) as the sequence of the heme protein (FIGS. 1-2, and 6-7). In some aspects, the selectable marker is the aadA gene which produces the aminoglycoside-3"-adenylyltransferase protein and provides resistance to aminoglycosides spectinomycin and streptomycin (FIGS. 3-5, and 8-10). In some aspects, the aadA gene is located in a separate linear construct and is co-bombarded with the linear construct holding the sequence of the heme proteins (FIGS. 3-5, and 8-10).

In some aspects, disclosed herein is a method to stably express a heme protein in plants, the method comprising a) transforming a plant with a plant transformation vector, b) regenerating the transgenic plants in vitro under selection pressure, and c) growing the transformed plants under the conditions wherein the recombinant heme proteins are expressed.

In some aspects, the levels of expression of a heme protein are referred to as "total soluble protein" ("TSP"). The expression level in TSP refers to an amount of a protein of interest relative to the total amount of protein that may reasonably be extracted from a plant using standard methods. Methods for extracting total protein from plant tissues such as seeds are known in the art (Cunha et al. (2011a), Transgenic Res. 20:811. Cunha et al. (2011b), Transgenic Res. 20:841, Ding et al. (2006), Biotechnol. Lett. 28:869). The amount of protein of interest may be measured using methods known in the art, such as an ELISA or a Western Blot.

The heme proteins and transgenic plants described herein may be used to prepare food compositions. In some aspects, the recombinant heme proteins produced by the transgenic plants may be used in its entirety, fractions and modifications thereof including solubilized, precipitated, partially or fully hydrolyzed, crosslinked, emulsified, texturized, cooked, extruded, reacted, structured versions to prepare meat-like (meat analogs) food stuffs including comminuted meats such as minced meat, meat strips, cubes and steaks; reconstituted and formed meat-like products including burgers, fillets, balls, sticks, slabs; reconstituted and stuffed/filled meat-like (meat analog) products including sausages, ham-like products, spreadables, reconstituted and coated meat-like products including nuggets, patties, strips, poppers, rings and more. The recombinant heme proteins may also be extracted from the transgenic plant using standard methods known in the field.

In some aspects, the food composition is prepared using the seed of the transgenic plant expressing the recombinant heme protein. In some aspects, the food composition is prepared using the recombinant heme protein extracted and purified from the seed.

The following experiments demonstrate different recombinant sequences that contain heme proteins and methods for producing recombinant proteins in plants. While the examples below describe expression in soybean, it will be understood by those skilled in the art that the expression sequences and methods disclosed herein may be tailored for expression in any monocot or dicot plants.

The practice of the present disclosure will employ, unless otherwise indicated, conventional techniques of cell biology, cell culture, molecular biology, transgenic biology, microbiology, recombinant DNA, biotechnology, plant genetic engineering and immunology, which are within the skill of the art. Such techniques are explained fully in the literature.

All of the references cited above, as well as all references cited herein, are incorporated herein by reference in their entireties.

The present disclosure is to be considered as an exemplification of the invention and is not intended to limit the invention to the specific aspects illustrated by the figures or description below. The present invention will now be described by referencing the appended figures representing specific aspects.

EXAMPLES

Example 1. Construction of Plant Transformation Vectors

A codon-optimized gene comprising the alpha and beta subunits of porcine hemoglobin genes, referred to as HbA-LL-HbB, was synthesized by Genscript. The HbA-LL-HbB gene was cloned into the inhouse pIPTRA0-2×35S-MCS vector using the BamHI/HindIII restriction sites. The HbA-LL-HbB gene was cloned in between the 35S promoter and NOS terminator to create the pIPTRA0: p35S+HbA-LL-HbB vector (SEQ ID NO: 3). FIG. 1 shows a graphic representation of the pIPTRA0: p35S+HbA-LL-HbB vector, while FIG. 6 shows the nucleotide sequences for each of the regulatory elements involved.

Figure 2:
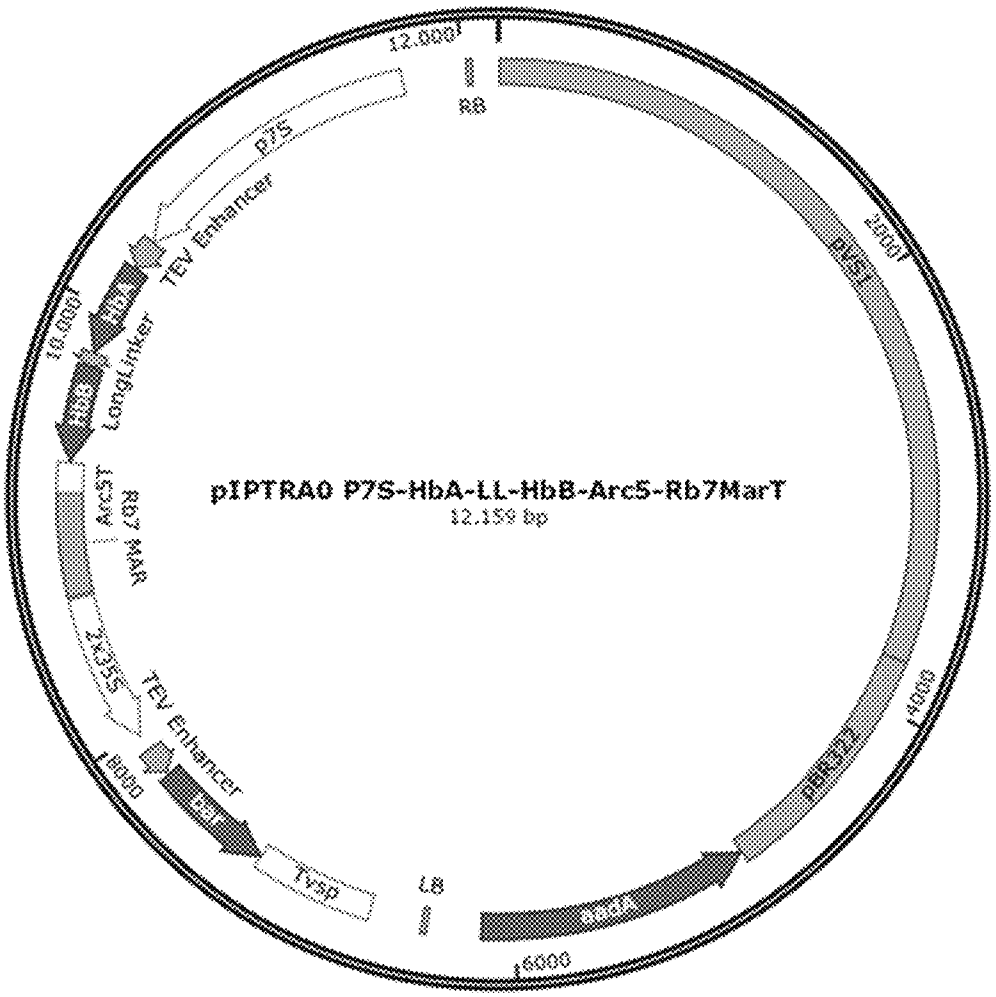
FIG. 2 (FIG. 2) depicts pIPTRA0: p7S+HbA-LL-HbB-Arc5T binary vector. This plasmid allows the expression of the hemoglobin (HbA-LL-HbB) gene driven by 7S globulin (7s) promoter, in conjunction with the ARC5 terminator and Rb7 matrix array region (MAR). The hemoglobin gene consists of the alpha-globin and beta-globin linked via a long linker (LL) of 63 bp. The vector backbone region is 12,159 bp long. The HbA-LL-HbB consists of a soybean codon-optimized sequence.
Figure 3:
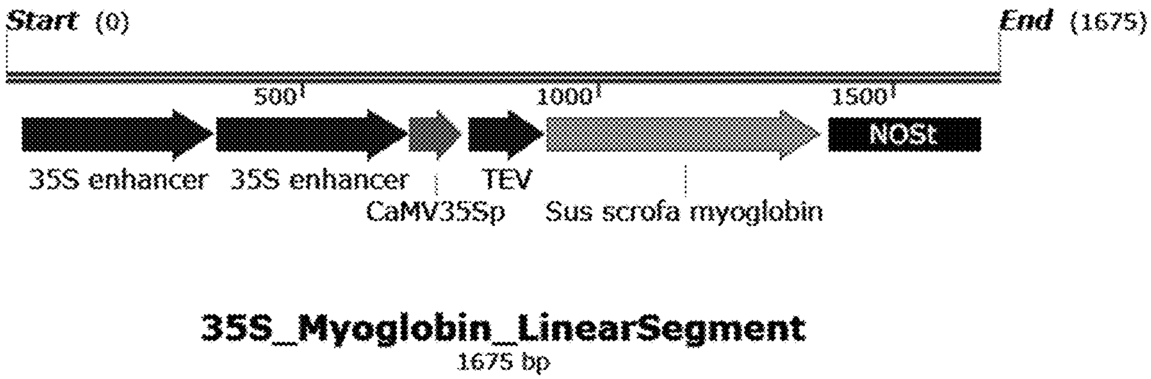
FIG. 3 (FIG. 3) shows the 35S+TEV+myoglobincDNA+NOS linear construct, referred to as EC1. This linear construct allows the expression of the myoglobin gene driven by constitutive promoter CaMV35S promoter, and includes the Nopaline synthase terminator (TNOS). The linear construct is 1.655 bp long. The myoglobin gene consists of a soybean codon-optimized sequence.
Figure 4:
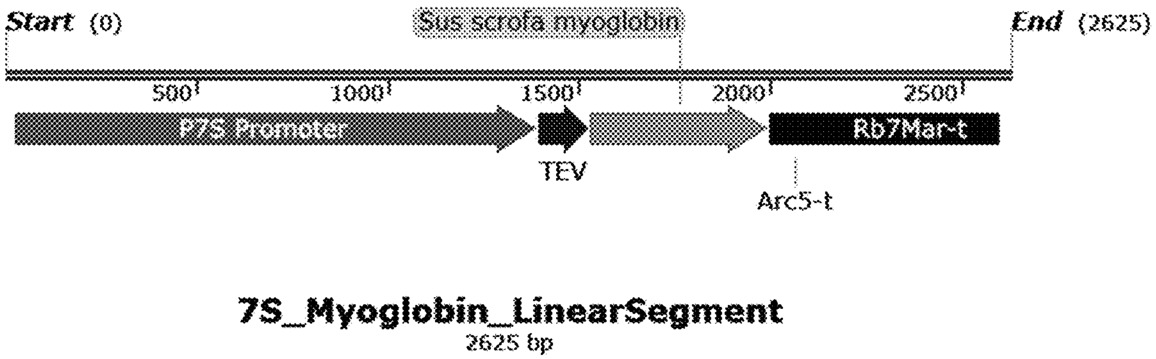
FIG. 4 (FIG. 4) illustrates the p7S+TEV+myoglobin-cDNA+arc5+Rb7MAR linear construct, referred to as EC2. This linear construct allows the expression of the myoglobin gene driven by the 7S globulin promoter, in conjunction with the ARC5 terminator and Rb7 matrix array region (MAR). The linear construct is 3,220 bp long. The myoglobin gene consists of a soybean codon-optimized sequence.

The 7S promoter fused to TEV Enhancer (p7S-TEV), and the arc5 Terminator fused to Rb7 Matrix Attachment Region (arc5T-Rb7MAR) were synthesized by Genscript. The pIPTRA0: p35S+HbA-LL-HbB vector was modified to create the pIPTRA0: p7S+HbA-LL-HbB-Arc5T vector (SEQ ID NO:4). The 35S promoter was replaced with the p7S-TEV using the XbaI/BamHI restriction sites. The NOS terminator was replaced by the arc5T-Rb7MAR fusion using the HindIII/SpeI restriction sites. The graphic representation and nucleotide sequences of pIPTRA0: p7S+HbA-LL-HbB-Arc5T vector are shown in FIGS. 2 and 7, respectively.

The 35S+TEV+myoglobincDNA+NOS (SEQ ID NO:5), p7S+TEV+myoglobincDNA+arc5+Rb7MAR (SEQ ID NO:6), and PPhas+myoglobincDNA+arc5+Rb7MAR (SEQ ID NO:7) expression vectors are referred to as EC1, EC2, and EC3, respectively. EC1, EC2, and EC3 were assembled via Golden Gate cloning in the in-house pEXPLODER plasmid. Promoters, myoglobin, and terminators were incorporated into the pEXPLODER plasmid. Following successful assembly of EC1, EC2, and EC3 linear fragments were released from the circular plasmid via BsaI digestion, followed by size separation in a 0.5% (w/v) agarose gel. After gel purification, EC1, EC2, and EC3 were separated from the section carrying the selectable marker via Asc1 digestion. The two resulting linear constructs (selectable marker+ EC1, EC2, or EC3) were co-bombarded into soybean explants. Graphic representation of the three linearized fragments are presented in FIGS. 3, 4, and 5. Nucleotide sequences for EC1, EC2, and EC3 are presented in FIGS. 8, 9, and 10, respectively.

Example 2. Confirmation of Transgenic Events

Figures 11A, 11B:
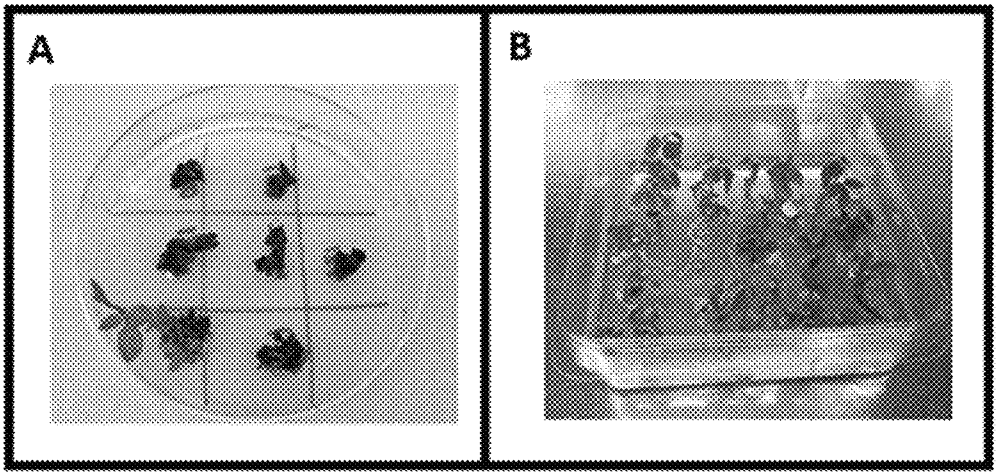
FIGS. 11A-11B (FIGS. 11A-11B) depict the regeneration (11A, 11B) of soybean transgenic lines. Image A and B show shoots regenerating on selection media transformed with pIPTRA0: p7S+HbA-LL-HbB-Arc5T and EC3, respectively. Shoots from Image A and B were transformed via *agrobacterium* and biolistic transformation methods, respectively.

In vitro regeneration of putative transgenic lines was obtained for all the constructions used in this aspect (FIGS. 11A-11B). DNA was extracted from leaf tissue of regenerated explants for further genetic screening.

Figure 12:
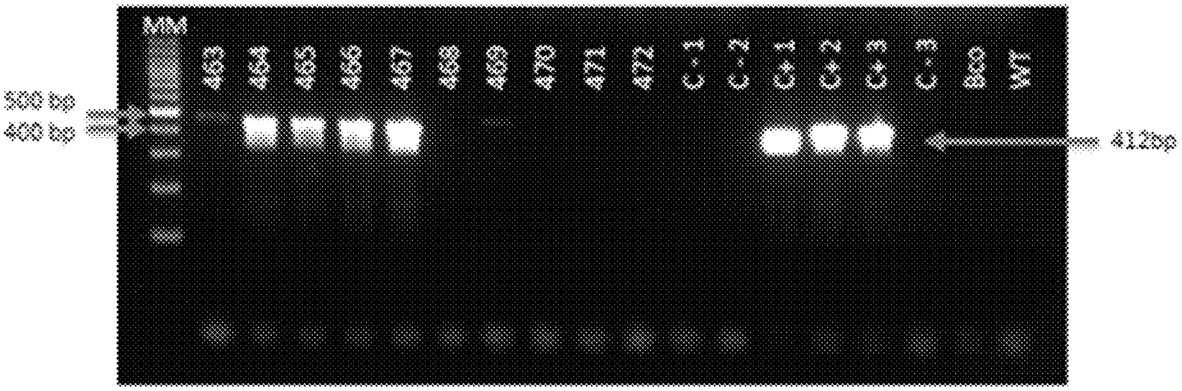
FIG. 12 (FIG. 12) shows PCR amplification results from events transformed with pIPTRA0: p35S+HbA-LL-HbB binary vector. Specific primers were designed for the detection of the 2×35S promoter and HbA CDS. The expected amplicon length is 412 bp. MM: molecular marker (100 bp). 463 to 472 samples are a batch of potential transgenic plants produced in study. C−1 and C−2 are negative controls prepared during DNA extraction. C+1 to C+2 are positive controls for pIPTRA0: p35S+HbA-LL-HbB binary vector from two plant samples characterized previously. C+3 was amplified from the pIPTRA0: p35S+HbA-LL-HbB binary vector. C−3 DNA represents another binary vector (negative control). Bco: blank of PCR. WT: wild type soybean DNA FIG. 13 (FIG. 13) shows PCR amplification results from events transformed with pIPTRA0: p7S+HbA-LL-HbB-Arc5T binary vector. Specific primers were designed for the detection of the 7S promoter and HbA CDS. The expected amplicon length is 390 bp. MM: molecular marker (100 bp). 563 to 562 samples are a batch of potential transgenic plants produced in study. C−1 is a negative control prepared during DNA extraction. Bco is a blank for PCR. WT: wild type soybean DNA. C+1 is a positive sample for pIPTRA0: p7S+HbA-LL-HbB-Arc5T that had been characterized previously. C−3 DNA represents another binary vector (negative control). C+2 was amplified from the pIPTRA0: p7S+HbA-LL-HbB-Arc5T binary vector.
Figure 13:
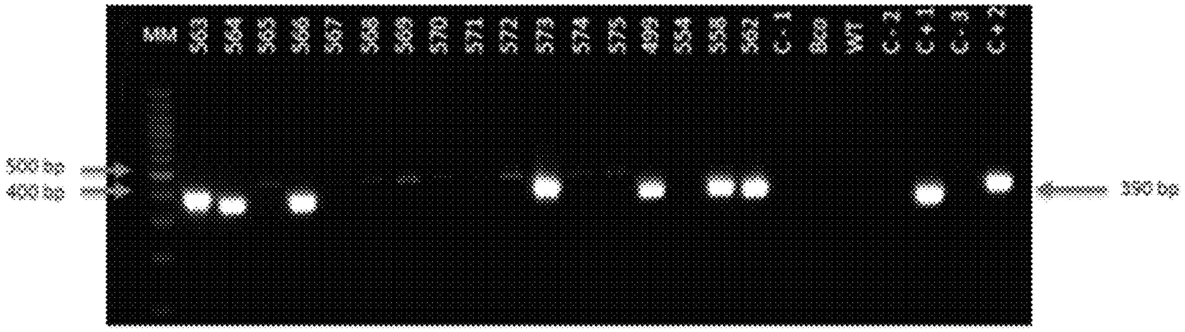
Figure 14:
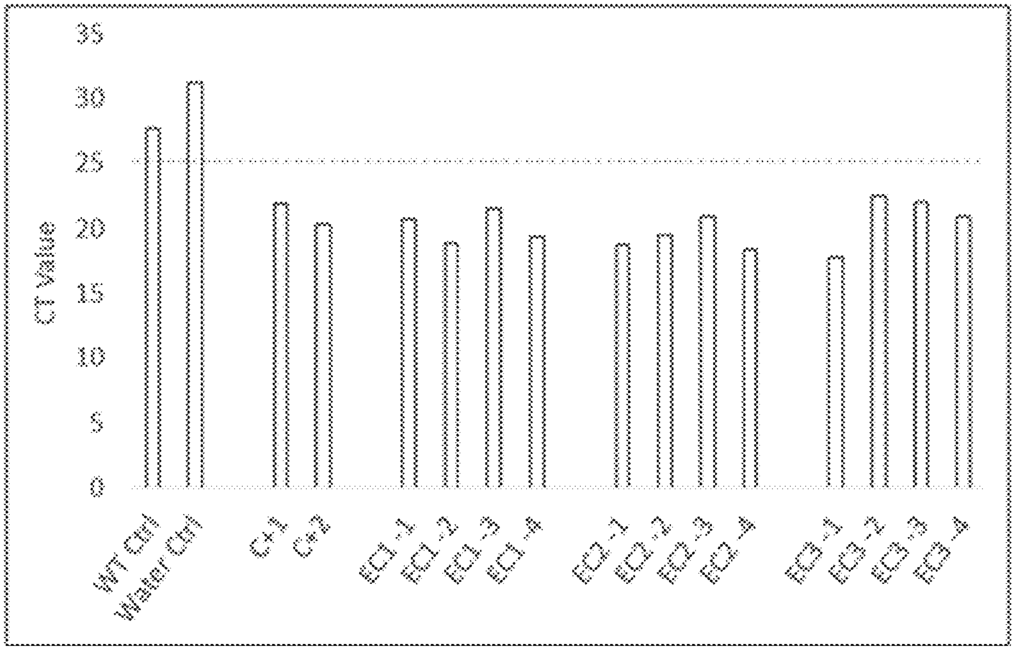
FIG. 14 (FIG. 14) shows qPCR amplification results from events transformed with EC1, EC2, and EC3 vectors. Specific primers were designed for the detection of the aadA1a CDS. Red line: Marker Ct cutoff, positives must be <25 Ct value. WT Ctrl: wild type soybean DNA. Water Ctrl: water control. C+1 and C+2 are positive controls for the aadA1 that had been characterized previously. Samples 1 to 4 for EC1, EC2, and EC3 are batches of potential transgenic plants produced in study.

DNA from putative transformed lines with pIPTRA0: p35S+HbA-LL-HbB and pIPTRA0: p7S+HbA-LL-HbB-Arc5T was PCR-screened for the presence of the transgenic insert in the host genome. Agarose gel pictures show PCR amplification results for putative transgenic lines for pIPTRA0: p35S+HbA-LL-HbB (FIG. 12) and IPTRA0: p7S+HbA-LL-HbB-Arc5T (FIG. 13). The presence of a 412 and 390 bp band confirms the presence of the transgenic insert for lines transformed with pIPTRA0: p35S+HbA-LL-HbB and IPTRA0: p7S+HbA-LL-HbB-Arc5T, respectively.

qPCR of a section of the aadA1a CDS was performed in order to confirm the presence of the transgenic insert for lines putatively transformed with EC1, EC2, and EC3 (FIG. 14). The marker Ct cutoff for positive lines must be <25.

Example 3. Total Soluble Protein Production in Soybean Transgenic Events Carrying the Porcine Hemoglobin Gene The transgenic TO plants transformed with pIPTRA0: p35S+HbA-LL-HbB and pIPTRA0: p7S+HbA-LL-HbB-Arc5T were cultivated and propagated to T1 seeds. T1 seeds were screened for the presence of the porcine hemoglobin gene via PCR, a small section of the seed was excised for PCR purposes.

Figures 15A, 15B, 15C:
FIGS. 15A-15C (FIGS. 15A-15C) depict protein extracts coloration from soybean seeds of WT (FIG. 15A), pIPTRA0: p35S+HbA-LL-HbB (FIG. 15B), and pIPTRA0: p7S+HbA-LL-HbB-Arc5T (FIG. 15C) transgenic events. Protein extractions from FIG. 15C show a pink coloration (darker shading in the black and white image of FIG. 15C) likely attributed to the expression and presence of the heterologous hemoglobin gene. An arrow and circles were added to point at the darker shading.
Figures 16A, 16B, 16C:
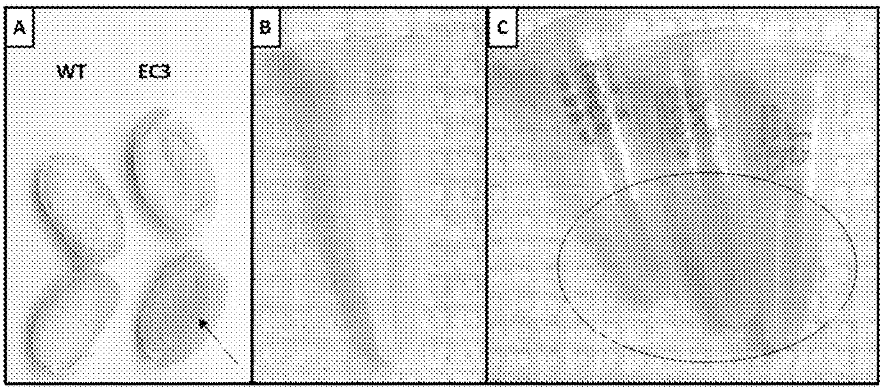
FIGS. 16A-16C (FIGS. 16A-16C) show coloration of soybean half-cut seeds (FIG. 16A) and of protein extracts from soybean seeds (FIG. 16B, 16C). Half-cut seeds are shown for WT seeds (left side of panel FIG. 16A) and for a transgenic EC3 event (right side of panel FIG. 16A). Protein seed extractions are shown for WT seeds (FIG. 16B) and for transgenic EC3 events (FIG. 16C). Pink coloration shown in FIGS. 16A and 16C, (darker shading in the black and white images of FIGS. 16A and 16C) corresponding to EC3 transgenic lines, is likely attributed to the expression and presence of the heterologous porcine myoglobin gene.
Figure 17A:
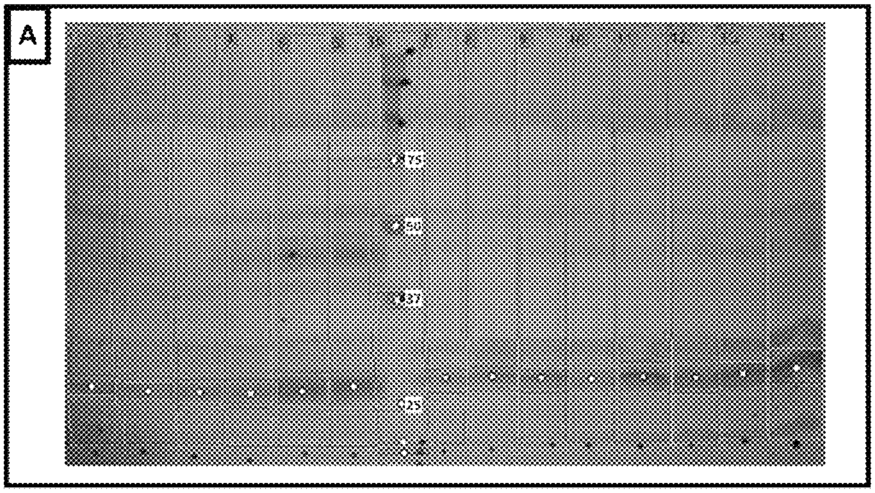
FIGS. 17A-17C (FIGS. 17A-17C) illustrate three replicates of Western blot (17A, 17B, 17C) analyses of soybean seeds. Soybean seed protein extracts were run on 12% SDS PAGE gels. Protein bands were then transferred to a nitrocellulose membrane and western blots were developed with the anti-porcine antibody. White dots indicate control hemoglobin bands as well as putative hemoglobin bands at 16 kDa (monomer), 32 kDa (dimer), and 64 kDa (tetramer). Lane 1:100 μg of WT extract. Lanes 2 to 6: WT extract+10, 25, 50, 150, and 250 ng of Hb standard, respectively. Lanes 7 to 14:100 μg protein extract of EC3 events 63, 64, 65, 66, 67, 68, 69, 70. Lane 15: Molecular weight standard.
Figure 17B:
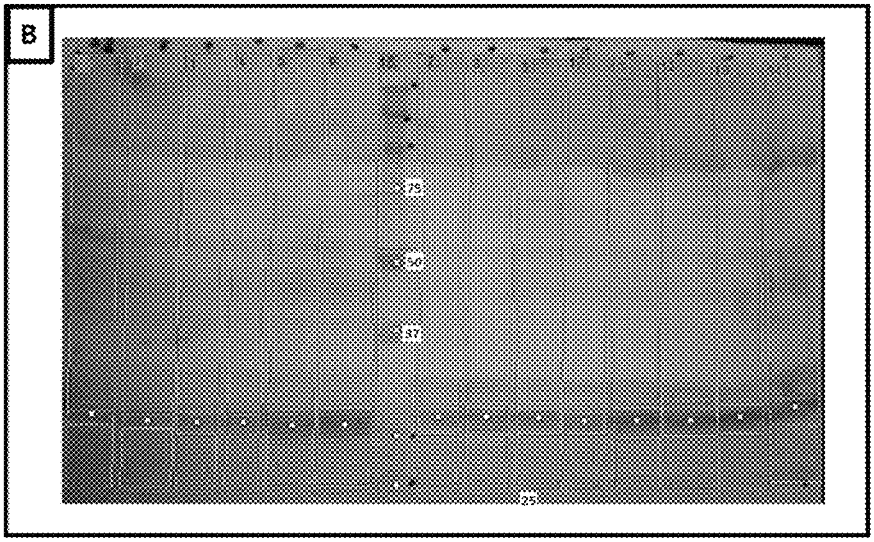
Figure 17C:
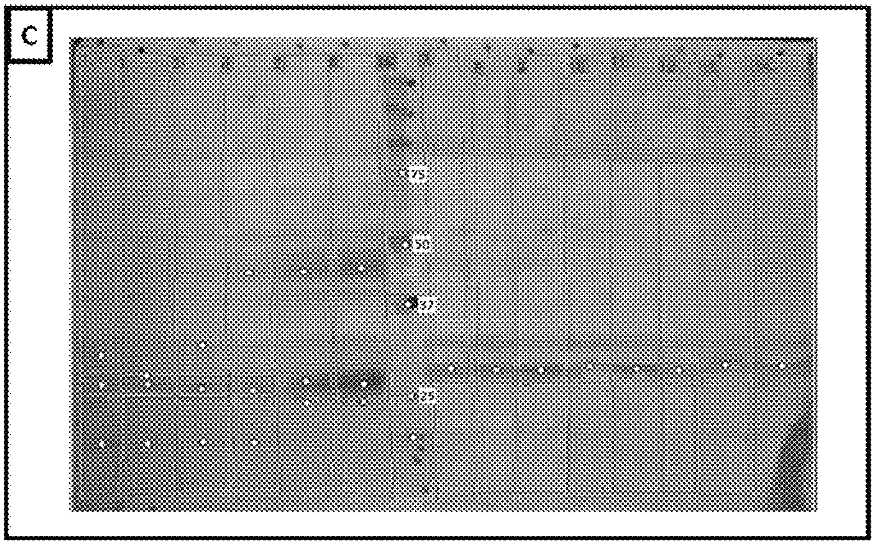

A total of 3 PCR positive seeds per transgenic event were pooled and protein extraction was performed. Pooled seeds were crushed in tissue-lyser, treated with extraction buffer (50 mM Tris-Cl pH 6.8, NaCl 50 mM, Na2SO3 36 mM, PHIC 1:200), and centrifuged at 13000 rpm at 4° C. for 10 minutes (FIGS. 15A-15C). After protein extraction, the extracts were then run on 10-well and 12% SDS PAGE gels, loading 100 μg proteins of each transgenic extract, a molecular weight standard, 100 μg protein extract of a WT used as a negative control, and WT extract+10, 25, 50, 150, and 250 ng of Hb standard (Sigma-Aldrich Hemoglobin porcine-lyophilized powder cat #H4131). Protein bands were then transferred to a nitrocellulose membrane and western blots were developed with the anti-porcine antibody (UsBiological Life sciences cat #140639) diluted 1/250 (FIGS. 17A-17C). Using the western blots, detected hemoglobin was quantified by comparing the intensity of the hemoglobin bands from the seed extracts with that from the hemoglobin standards, allowing calculation of the percentage hemoglobin of TSP (FIG. 18; Table 1).

TABLE 1

Accumulation of hemoglobin as a percentage of TSP content in independent transgenic soybean seed stocks. Table includes the coefficient of variation (%).

| Construct | Event ID | Average TSP (%) | Coefficient of Variation (%) |
|---|---|---|---|
| Empty Vector | 93 | <LOQ | n.d. |
| | 94 | <LOD | n.d. |
| pIPTRA0: p35S + HbA-LL-HbB | 14 | 0.036 | n.d. |
| | 15 | 0.047 | 0.238 |
| | 17 | <LOD | n.d. |
| | 18 | <LOD | n.d. |
| | 19 | 0.087 | 0.776 |
| pIPTRA0: p7S + HbA-LL-HbB-Arc5T | 46 | 0.114 | 0.495 |
| | 47 | <LOD | n.d |
| | 49 | 0.075 | n.d. |
| | 51 | 0.167 | 1.203 |
| | 52 | <LOD | n.d. |
| | 54 | 0.066 | 0.683 |
| | 57 | 0.172 | 0.952 |
| | 59 | 0.162 | 0.858 |
| | 61 | 0.039 | 0.930 |
| | 62 | 0.079 | 1.145 |
| | 63 | 0.078 | 0.406 |
| | 64 | 0.084 | 0.457 |
| | 65 | 0.110 | 0.320 |
| | 66 | 0.058 | 0.539 |
| | 67 | 0.148 | 0.576 |
| | 68 | 0.126 | 0.610 |
| | 69 | 0.138 | 0.829 |
| | 70 | 0.085 | 0.283 |
| | 71 | 0.124 | 0.690 |
| | 72 | 0.119 | 0.407 |
| | 73 | 0.122 | 0.466 |

TABLE 1-continued

Accumulation of hemoglobin as a percentage of TSP content in independent transgenic soybean seed stocks. Table includes the coefficient of variation (%).

| Construct | Event ID | Average TSP (%) | Coefficient of Variation (%) |
|---|---|---|---|
| | 75 | 0.110 | 0.113 |
| | 76 | 0.059 | 0.036 |
| | 77 | 0.077 | 0.058 |
| | 81 | <LOQ | n.d. |
| | 83 | 0.038 | n.d. |
| | 84 | 0.074 | 0.654 |
| | 85 | 0.030 | n.d. |
| | 86 | <LOQ | n.d. |
| | 87 | 0.060 | n.d. |
| | 88 | 0.069 | n.d. |
| | 89 | 0.189 | n.d. |
| | 90 | <LOQ | n.d. |

"n.d": Not determined, events with no coefficient of variation because two of three replicates were discarded.

Figure 18:
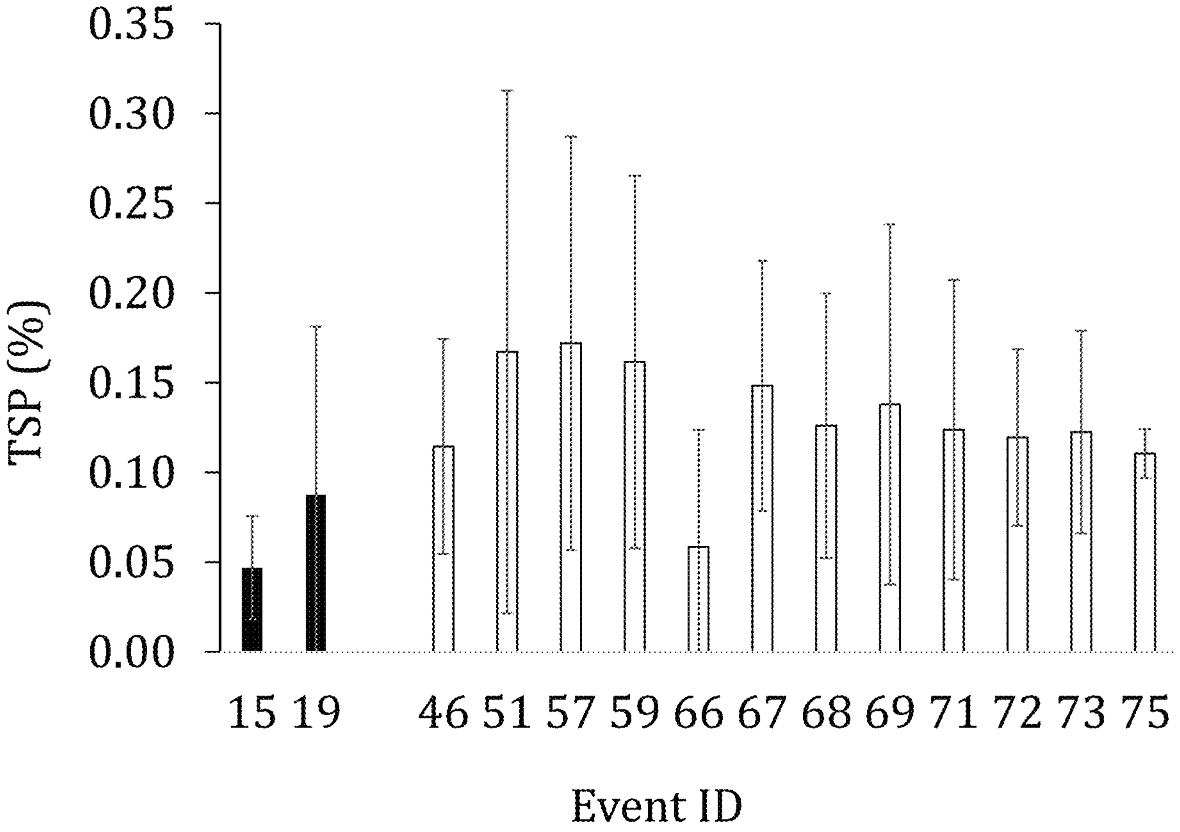
FIG. 18 (FIG. 18) depicts hemoglobin expression levels in seeds of soybean transgenic events. Total soluble protein (% TSP), represented in the Y axis, was obtained via Western blot quantitative analysis. Expression of events transformed with pIPTRA0: p35S+HbA-LL-HbB binary vector (events 15 and 19) are shown in black bars. Expression of events transformed with pIPTRA0: p7S+HbA-LL-HbB-Arc5T binary vector (events 46 to 75) are shown in white bars. WT and empty vector events are not shown in the graph because the expression values did not reach the limit of detection (LOD). The extracts were run on 12% SDS PAGE gels, then transferred to a nitrocellulose membrane and western blots were developed with the anti-porcine antibody. The percentage hemoglobin of TSP was quantified by comparing the intensity of the hemoglobin bands from the seed extracts with that from the hemoglobin standards. Each event consisted of one biological replicate (a pool of 3 seeds) with 3 technical replicates. Standard deviation is presented as error bars for each event.

Porcine hemoglobin identification and quantification from whole soybean seed protein extracts was also performed via Liquid chromatography-Mass spectrometry (LC-MS) (FIG. 18). An equal amount of soybean seed protein per transgenic event was digested with LysC/trypsin and then peptides desalted on C18 tips. LC-MS data were acquired on a Bruker timsTOF-Pro2 and searched against a soybean database supplemented with the pig hemoglobin sequence provided. The amounts of hemoglobin were determined by normalizing its MS2 intensity to soybean cupin. No hemoglobin was detected in the WT sample.

Transgenic events carrying the porcine myoglobin gene: The transgenic TO plants transformed with EC1, EC2, and EC3 linear constructs were cultivated and propagated up to T2 seeds. T2 seeds were screened for the presence of the porcine myoglobin gene via ddPCR; a small section of the seed was excised for PCR purposes.

A total of 3 PCR positive seeds per transgenic event were pooled and protein extraction was performed. Pooled seeds were ground in extraction buffer (5% w/v SDS, 175 mM Tris-HCl, pH 8.0, 0.4% v/v beta-mercaptoethanol) with Omni ceramic beads (1.4 mm); the extracts were heated to 65° C. for 25 min, centrifuged and the supernatants were transferred to fresh tubes. Myoglobin quantitation from seed extracts was done using the Alpha Diagnostics ELISA kit (cat #600-640-PMY). All samples were normalized to 50 μg/mL total soluble protein (TSP) and tested for myoglobin content according to the manufacturer's protocols. The concentration of myoglobin was determined by reference to the standard curve. Each event consisted of one biological replicate (a pool of 3 seeds) with 3 technical replicates. Twenty μL (1 μg) was tested for each sample. The percentage myoglobin of TSP is presented in FIGS. 20A-20B and Table 2.

TABLE 2

Accumulation of myoglobin as a percentage of TSP content (±s.d.) in independent transgenic soybean seed stocks. TSP content above 5% are shaded in gray.

| Linear Construct | Event ID | Average TSP (%) | SD |
|---|---|---|---|
| WT | WT | 0.40 | 0.00 |
| Empty vector | 1542-001a-010 | 0.05 | 0.02 |
| EC1 | 1545-003a-011 | 0.19 | 0.32 |
| | 1545-004a-006 | 0.00 | 0.00 |
| | 1545-006a-007 | 0.07 | 0.12 |

TABLE 2-continued

Accumulation of myoglobin as a percentage of TSP content (±s.d.) in independent transgenic soybean seed stocks. TSP content above 5% are shaded in gray.

| Linear Construct | Event ID | Average TSP (%) | SD |
|---|---|---|---|
| | 1545-013a-004 | 0.42 | 0.06 |
| | 1545-016a-008 | 0.00 | 0.01 |
| | 1545-024a-002 | 1.43 | 0.19 |
| | 1545-033a-009 | 0.00 | 0.01 |
| | 1545-034a-003 | 0.01 | 0.01 |
| | 1545-036a-008 | 0.42 | 0.10 |
| | 1545-037a-011 | 0.01 | 0.04 |
| EC2 | 1544-002a-006 | 0.09 | 0.13 |
| | 1544-006a-007 | 0.71 | 0.15 |
| | 1544-010a-008 | 0.72 | 0.29 |
| | 1544-011a-010 | 0.04 | 0.01 |
| | 1544-013a-008 | 0.01 | 0.01 |
| | 1544-014a-002 | 0.00 | 0.01 |
| | 1544-015a-010 | 0.04 | 0.03 |
| | 1544-016a-008 | 0.01 | 0.00 |
| | 1544-017a-010 | 4.19 | 2.32 |
| | 1544-005a-002 | 0.00 | 0.00 |
| | 1544-018a-003 | 0.19 | 0.18 |
| | 1544-022a-007 | 0.18 | 0.34 |
| | 1544-023a-007 | 0.00 | 0.01 |
| | 1544-025a-003 | 0.57 | 0.13 |
| | 1544-027a-001 | 0.43 | 0.39 |
| | 1544-030a-001 | 0.21 | 0.12 |
| EC3 | 1543-001a-011 | 8.47 | 1.29 |
| | 1543-033a-010 | 3.01 | 1.58 |
| | 1543-043a-006 | 0.79 | 0.10 |
| | 1543-051a-003 | 0.46 | 0.02 |
| | 1543-055a-003 | 9.93 | 0.76 |
| | 1543-059a-009 | 8.01 | 1.59 |
| | 1543-064a-007 | 1.31 | 0.13 |
| | 1543-068a-001 | 0.43 | 0.01 |
| | 1543-087a-004 | 6.34 | 1.29 |
| | 1543-088a-005 | 9.81 | 0.53 |
| | 1543-095a-009 | 1.54 | 0.22 |
| | 1543-004a-008 | 1.72 | 0.36 |
| | 1543-005a-010 | 0.03 | 0.01 |
| | 1543-006a-002 | 0.19 | 0.07 |

TABLE 2-continued

Accumulation of myoglobin as a percentage of TSP content (±s.d.) in independent transgenic soybean seed stocks. TSP content above 5% are shaded in gray.

| Linear Construct | Event ID | Average TSP (%) | SD |
|---|---|---|---|
| | 1543-007a-004 | 0.13 | 0.16 |
| | 1543-008a-002 | 15.59 | 0.26 |
| | 1543-009a-001 | 0.03 | 0.02 |
| | 1543-011a-002 | 10.59 | 3.28 |
| | 1543-012a-008 | 0.11 | 0.08 |
| | 1543-016a-001 | 0.17 | 0.11 |
| | 1543-017a-005 | 0.04 | 0.00 |
| | 1543-023a-005 | 0.02 | 0.01 |
| | 1543-025a-008 | 10.24 | 1.33 |
| | 1543-046a-001 | 0.11 | 0.02 |
| | 1543-053a-004 | 0.07 | 0.02 |
| | 1543-054a-007 | 0.24 | 0.02 |
| | 1543-057a-012 | 16.67 | 5.57 |
| | 1543-058a-012 | 0.30 | 0.36 |
| | 1543-061a-003 | 23.94 | 3.95 |
| | 1543-071a-005 | 1.01 | 0.42 |
| | 1543-073a-004 | 0.43 | 0.65 |
| | 1543-078a-001 | 0.06 | 0.01 |
| | 1543-085a-007 | 4.29 | 1.32 |
| | 1543-092a-003 | 26.58 | 1.43 |
| | 1543-122a-006 | 19.02 | 4.59 |
| | 1543-131a-004 | 2.55 | 0.65 |
| | 1543-134a-002 | 0.29 | 0.18 |
| | 1543-153a-008 | 3.16 | 2.58 |
| | 1543-183a-001 | 7.35 | 2.09 |
| | 1543-191a-006 | 15.82 | 2.52 |
| | 1543-203a-006 | 15.88 | 2.56 |
| | 1543-116a-004 | 0.00 | 0.00 |
| | 1543-119a-007 | 0.46 | 0.58 |
| | 1543-126a-008 | 0.03 | 0.02 |
| | 1543-132a-001 | 0.00 | 0.00 |
| | 1543-133a-009 | 1.05 | 1.46 |
| | 1543-137a-008 | 0.07 | 0.07 |
| | 1543-143a-002 | 7.73 | 6.88 |
| | 1543-165a-001 | 2.11 | 0.77 |

Sequences

| SEQ ID | Brief reference | nt |
|---|---|---|
| SEQ ID NO: 1 | porcine hemoglobin (HbALLHbB) | TCAATGATACTTGTGAGCAAGAGCATTTGCTAC GCCGGCAACAACCTTCTGAAATGCAGCCTGCAC ATTAGGGTTGAAATCATGACCAAGTCTACGGGC TAGGACTACAACAATGACGTTGCCGAGTAGGCG AAAATTTTCAGGGTCGACGTGAAGTTGATCACA ATGCAACTCAGATAACTTCGCAAAAGTACCTTTC AGGTTGTCCAAATGCTTCAGCCCATCAGAGAAT GATTGCAATACTTTCTTTCCATGAGCTTTCACTT TTGGATTTCCCATAACAGCATCTGCATTGGACAA ATCACCAAAGCTCTCAAAGAATCTTTGTGTCCAG GGGTAAACCACAAGGAGCCTCCCAAGTGCCTCT CCACCAACTTCATCAACATTAACTTTTCCCCACA ACCCTAACACTGCTTCCTTTTCCTCAGCACTGAG GTGCACACTTCCTCCACCTCCAGATCCTCCACCT CCTGATCCTCCACCTCCTGATCCTCCACCTCCAC TCCTATATTTGCTGGTGAGTACAGTTGAGACGTT GGCGAGGAACTTGTCCAAACTGGCATGCACAGA AGGATTAAAATCATCTGGATGGTGGGCGGCTAA AGTGACTAACAAACAATGGGACAGCAGCTTGAA ATTTACCGGATCAACTCTCAATTTGTGTGCATGA AGATCAGATAATGCAGAAAGTGCGCCGGGAAGG TCATCCAAGTGCCCAACAGCTTTTGTCAAAGCAT CAGCCACCTTCTGCCCATGTGCCTTCACTTGATC ACTTCCATGTGAGAGGTTGAAATGAGGAAAGTA AGTCTTTGTCGTTGGAAAGCCAAGAAACATACG CTCAAGAGCTTCAGCACCGTGCGCTCCAGCTTG ACCACCAACTTTTCCCCAAGCAGCCTTAACATTT GCTTTGTCTGCTGCCGATAGAACCAT |

-continued

| SEQ ID | Brief reference | nt |
|---|---|---|
| SEQ ID NO: 2 | porcine Myoglobin | ATGGGGCTATCAGATGGTGAATGGCAACTTGTA<br>TTGAATGTTTGGGGAAAAGTTGAAGCTGATGTT<br>GCTGGACATGGTCAAGAAGTGTTAATAAGACTC<br>TTCAAAGGCCACCCTGAAACATTAGAGAAGTTT<br>GACAAATTCAAGCACCTAAAATCTGAAGATGAA<br>ATGAAGGCCTCCGAGGACTTGAAGAAGCATGGA<br>AACACTGTCCTGACTGCACTCGGCGGGATCCTC<br>AAAAAGAAAGGTCATCATGAAGCGGAGTTGACA<br>CCATTGGCTCAGTCTCATGCTACCAAACACAAG<br>ATTCCTGTGAAGTATCTTGAGTTTATTAGTGAGG<br>CCATAATTCAGGTTTTGCAATCAAAACATCCCGG<br>TGATTTTGGTGCAGATGCTCAAGGAGCAATGAG<br>CAAAGCACTGGAGCTTTTCAGGAATGATATGGC<br>AGCCAAGTACAAGGAACTTGGATTTCAGGGGTG<br>A |
| SEQ ID NO: 3 | pIPTRA0:p35S + HbA-LL-HbB | 5'<br>TGGCAGGATATATTGTGGTGTAAACAAATTGAC<br>GCTTAGACAACTTAATAACACATTGCGGACGTTT<br>TTAATGTACTGAATTAACGCCGAATTGCTCTAGC<br>ATTCGCCATTCAGGCTGCGCAACTGTTGGGAAG<br>GGCGATCGGTGCGGGCCTCTTCGCTATTACGCC<br>AGCTGGCGAAAGGGGGATGTGCTGCAAGGCGA<br>TTAAGTTGGGTAACGCCAGGGTTTTCCCAGTCA<br>CGACGTTGTAAAACGACGGCCAGTGCCAAGCTA<br>ATTCGCTTCAAGACGTGCTCAAATCACTATTTCC<br>ACACCCCTATATTTCTATTGCACTCCCTTTTAAC<br>TGTTTTTTATTACAAAAATGCCCTGGAAAATGCA<br>CTCCCTTTTTGTGTTTGTTTTTTTGTGAAACGAT<br>GTTGTCAGGTAATTTATTTGTCAGTCTACTATGG<br>TGGCCCATTATATTAATAGCAACTGTCGGTCCAA<br>TAGACGACGTCGATTTTCTGCATTTGTTTAACCA<br>CGTGGATTTTATGACATTTTATATTAGTTAATTT<br>GTAAAACCTACCCAATTAAAGACCTCATATGTTC<br>TAAAGACTAATACTTAATGATAACAATTTTCTTT<br>TAGTGAAGAAAGGGATAATTAGTAAATATGGAA<br>CAAGGGCAGAAGATTTATTAAAGCCGCGTAAGA<br>GACAACAAGTAGGTACGTGGAGTGTCTTAGGTG<br>ACTTACCCACATAACATAAAGTGACATTAACAAA<br>CATAGCTAATGCTCCTATTTGAATAGTGCATATC<br>AGCATACCTTATTACATATAGATAGGAGCAAACT<br>CTAGCTAGATTGTTGAGCAGATCTCGGTGACGG<br>GCAGGACCGGACGGGGCGGTACCGGCAGGCTG<br>AAGTCCAGCTGCCAGAAACCCACGTCATGCCAG<br>TTCCCGTGCTTGAAGCCGGCCGCCCGCAGCATG<br>CCGCGGGGGGCATATCCGAGCGCCTCGTGCATG<br>CGCACGCTCGGGTCGTTGGGCAGCCCGATGACA<br>GCGACCACGCTCTTGAAGCCCTGTGCCTCCAGG<br>GACTTCAGCAGGTGGGTGTAGAGCGTGGAGCCC<br>AGTCCCGTCCGCTGGTGGCGGGGGGAGACGTA<br>CACGGTCGACTCGGCCGTCCAGTCGTAGGCGTT<br>GCGTGCCTTCCAGGGGCCCGCGTAGGCGATGCC<br>GGCGACCTCGCCGTCCACCTCGGCGACGAGCCA<br>GGGATAGCGCTCCCGCAGACGGACGAGGTCGTC<br>CGTCCACTCCTGCGGTTCCTGCGGCTCGGTACG<br>GAAGTTGACCGTGCTTGTCTCGATGTAGTGGTT<br>GACGATGGTGCAGACCGCCGGCATGTCCGCCTC<br>GGTGGCACGGCGGATGTCGGCCGGGCGTCGTT<br>CTGGGCTCATGGTAGATCCCCCGTTCGTAAATG<br>GTGAAAATTTTCAGAAAATTGCTTTTGCTTTAAA<br>AGAAATGATTTAAATTGCTGCAATAGAAGTAGA<br>ATGCTTGATTGCTTGAGATTCGTTTGTTTTGTAT<br>ATGTTGTGTTGAGAATTAATTCTCGAGGTCCTCT<br>CCAAATGAAATGAACTTCCTTATATAGAGGAAG<br>GGTCTTGCGAAGGATAGTGGGATTGTGCGTCAT<br>CCCTTACGTCAGTGGAGATATCACATCAATCCA<br>CTTGCTTTGAAGACGTGGTTGGAACGTCTTCTTT<br>TTCCACGATGCTCCTCGTGGGTGGGGGTCCATC<br>TTTGGGACCACTGTCGGCAGAGGCATCTTCAAC<br>GATGGCCTTTCCTTTATCGCAATGATGGCATTTG<br>TAGGAGCCACCTTCCTTTTCCACTATCTTCACAA<br>TAAAGTGACAGATAGCTGGGCAATGGAATCCGA<br>GGAGGTTTCCGGATATTACCCTTTGTTGAAAAG<br>TCTCAATTGCCCTTTGGTCTTCTGAGACTGTATC<br>TTTGATATTTTTGGAGTAGACAAGTGTGTCGTGC<br>TCCACCATGTTATCACATCAATCCACTTGCTTTG<br>AAGACGTGGTTGGAACGTCTTCTTTTTCCACGAT |

-continued

| SEQ ID | Brief reference | nt |
|---|---|---|
| | | GCTCCTCGTGGGTGGGGGTCCATCTTTGGGACC<br>ACTGTCGGCAGAGGCATCTTCAACGATGGCCTT<br>TCCTTTATCGCAATGATGGCATTTGTAGGAGCC<br>ACCTTCCTTTTCCACTATCTTCACAATAAAGTGA<br>CAGATAGCTGGGCAATGGAATCCGAGGAGGTTT<br>CCGGATATTACCCTTTGTTGAAAAGTCTCAATTG<br>CCCTTTGGTCTTCTGAGACTGTATCTTTGATATT<br>TTTGGAGTAGACAAGTGTGTCGTGCTCCACCAT<br>GTTGACCTGCAGACTAGTCCGATCTAGTAACAT<br>AGATGACACCGCGCGCGATAATTTATCCTAGTT<br>TGCGCGCTATATTTTGTTTTCTATCGCGTATTAA<br>ATGTATAATTGCGGGACTCTAATCATAAAAACCC<br>ATCTCATAAATAACGTCATGCATTACATGTTAAT<br>TATTACATGCTTAACGTAATTCAACAGAAATTAT<br>ATGATAATCATCGCAAGACCGGCAACAGGATTC<br>AATCTTAAGAAACTTTATTGCCAAATGTTTGAAC<br>GATCGGGGAAATTGAGCTCGCCCGGGAAAGCTT<br>CAATGATACTTGTGAGCAAGAGCATTTGCTACG<br>CCGGCAACAACCTTCTGAAATGCAGCCTGCACA<br>TTAGGGTTGAAATCATGACCAAGTCTACGGGCT<br>AGGACTACAACAATGACGTTGCCGAGTAGGCGA<br>AAATTTTCAGGGTCGACGTGAAGTTGATCACAA<br>TGCAACTCAGATAACTTCGCAAAAGTACCTTTCA<br>GGTTGTCCAAATGCTTCAGCCCATCAGAGAATG<br>ATTGCAATACTTTCTTTCCATGAGCTTTCACTTT<br>TGGATTTCCCATAACAGCATCTGCATTGGACAA<br>ATCACCAAAGCTCTCAAAGAATCTTTGTGTCCAG<br>GGGTAAACCACAAGGAGCCTCCCAAGTGCCTCT<br>CCACCAACTTCATCAACATTAACTTTTCCCCACA<br>ACCCTAACACTGCTTCCTTTTCCTCAGCACTGAG<br>GTGCACACTTCCTCCACCTCCAGATCCTCCACCT<br>CCTGATCCTCCACCTCCTGATCCTCCACCTCCAC<br>TCCTATATTTGCTGGTGAGTACAGTTGAGACGTT<br>GGCGAGGAACTTGTCCAAACTGGCATGCACAGA<br>AGGATTAAAATCATCTGGATGGTGGGCGGCTAA<br>AGTGACTAACAAACAATGGGACAGCAGCTTGAA<br>ATTTACCGGATCAACTCTCAATTTGTGTGCATGA<br>AGATCAGATAATGCAGAAAGTGCGCCGGGAAGG<br>TCATCCAAGTGCCCAACAGCTTTTGTCAAAGCAT<br>CAGCCACCTTCTGCCCATGTGCCTTCACTTGATC<br>ACTTCCATGTGAGAGGTTGAAATGAGGAAAGTA<br>AGTCTTTGTCGTTGGAAAGCCAAGAAACATACG<br>CTCAAGAGCTTCAGCACCGTGCGCTCCAGCTTG<br>ACCACCAACTTTTCCCCAAGCAGCCTTAACATTT<br>GCTTTGTCTGCTGCCGATAGAACCATGGATCCT<br>CTAGTGGTAGATCCCCCGTTCGTAAATGGTGAA<br>AATTTTCAGAAAATTGCTTTTGCTTTAAAAGAAA<br>TGATTTAAATTGCTGCAATAGAAGTAGAATGCTT<br>GATTGCTTGAGATTCGTTTGTTTTGTATATGTTG<br>TGTTGAGAATTAATTCTCGAGGTCCTCTCCAAAT<br>GAAATGAACTTCCTTATATAGAGGAAGGGTCTT<br>GCGAAGGATAGTGGGATTGTGCGTCATCCCTTA<br>CGTCAGTGGAGATATCACATCAATCCACTTGCTT<br>TGAAGACGTGGTTGGAACGTCTTCTTTTTCCAC<br>GATGCTCCTCGTGGGTGGGGGTCCATCTTTGGG<br>ACCACTGTCGGCAGAGGCATCTTCAACGATGGC<br>CTTTCCTTTATCGCAATGATGGCATTTGTAGGAG<br>CCACCTTCCTTTTCCACTATCTTCACAATAAAGT<br>GACAGATAGCTGGGCAATGGAATCCGAGGAGGT<br>TTCCGGATATTACCCTTTGTTGAAAAGTCTCAAT<br>TGCCCTTTGGTCTTCTGAGACTGTATCTTTGATA<br>TTTTTGGAGTAGACAAGTGTGTCGTGCTCCACC<br>ATGTTATCACATCAATCCACTTGCTTTGAAGACG<br>TGGTTGGAACGTCTTCTTTTTCCACGATGCTCCT<br>CGTGGGTGGGGGTCCATCTTTGGGACCACTGTC<br>GGCAGAGGCATCTTCAACGATGGCCTTTCCTTT<br>ATCGCAATGATGGCATTTGTAGGAGCCACCTTC<br>CTTTTCCACTATCTTCACAATAAAGTGACAGATA<br>GCTGGGCAATGGAATCCGAGGAGGTCTCCGGAT<br>ATTACCCTTTGTTGAAAAGTCTCAATTGCCCTTT<br>GGTCTTCTGAGACTGTATCTTTGATATTTTTGGA<br>GTAGACAAGTGTGTCGTGCTCCACCATGTTGAC<br>TCTAGAGAATTCGTAATCATGTCATAGCTGTTTC<br>CTGTGTGAAATTGTTATCCGCTCACAATTCCACA<br>CAACATACGAGCCGGAAGCATAAAGTGTAAAGC<br>CTGGGGTGCCTAATGAGTGAGCTAACTCACATT<br>AATTGCGTTGCGCTCACTGCCCGCTTTCCAGTC |

-continued

| SEQ ID | Brief reference | nt |
|---|---|---|
| | | GGGAAACCTGTCGTGCCAGCTGCATTAATGAAT |
| | | CGGCCAACGCGCGGGGAGAGGCGGTTTGCGTA |
| | | TTGGAGCTTGAGCTTGGATCAGATTGTCGTTTC |
| | | CCGCCTTCAGTTTAAACTATCAGTGTTTGACAGG |
| | | ATATATTGGCGGGTAAAC |
| | | 3' |
| SEQ ID | pIPTRA0:p7S + | 5' |
| NO: 4 | HbA-LL-HbB-Arc5T | TGGCAGGATATATTGTGGTGTAAACAAATTGAC |
| | | GCTTAGACAACTTAATAACACATTGCGGACGTTT |
| | | TTAATGTACTGAATTAACGCCGAATTGCTCTAGC |
| | | ATTCGCCATTCAGGCTGCGCAACTGTTGGGAAG |
| | | GGCGATCGGTGCGGGCCTCTTCGCTATTACGCC |
| | | AGCTGGCGAAAGGGGGATGTGCTGCAAGGCGA |
| | | TTAAGTTGGGTAACGCCAGGGTTTTCCCAGTCA |
| | | CGACGTTGTAAAACGACGGCCAGTGCCAAGCTA |
| | | ATTCGCTTCAAGACGTGCTCAAATCACTATTTCC |
| | | ACACCCCTATATTTCTATTGCACTCCCTTTTAAC |
| | | TGTTTTTTATTACAAAAATGCCCTGGAAAATGCA |
| | | CTCCCTTTTTGTGTTTGTTTTTTTGTGAAACGAT |
| | | GTTGTCAGGTAATTTATTTGTCAGTCTACTATGG |
| | | TGGCCCATTATATTAATAGCAACTGTCGGTCCAA |
| | | TAGACGACGTCGATTTTCTGCATTTGTTTAACCA |
| | | CGTGGATTTTATGACATTTTATATTAGTTAATTT |
| | | GTAAAACCTACCCAATTAAAGACCTCATATGTTC |
| | | TAAAGACTAATACTTAATGATAACAATTTTCTTT |
| | | TAGTGAAGAAAGGGATAATTAGTAAATATGGAA |
| | | CAAGGGCAGAAGATTTATTAAAGCCGCGTAAGA |
| | | GACAACAAGTAGGTACGTGGAGTGTCTTAGGTG |
| | | ACTTACCCACATAACATAAAGTGACATTAACAAA |
| | | CATAGCTAATGCTCCTATTTGAATAGTGCATATC |
| | | AGCATACCTTATTACATATAGATAGGAGCAAACT |
| | | CTAGCTAGATTGTTGAGCAGATCTCGGTGACGG |
| | | GCAGGACCGGACGGGGCGGTACCGGCAGGCTG |
| | | AAGTCCAGCTGCCAGAAACCCACGTCATGCCAG |
| | | TTCCCGTGCTTGAAGCCGGCCGCCCGCAGCATG |
| | | CCGCGGGGGGCATATCCGAGCGCCTCGTGCATG |
| | | CGCACGCTCGGGTCGTTGGGCAGCCCGATGACA |
| | | GCGACCACGCTCTTGAAGCCCTGTGCCTCCAGG |
| | | GACTTCAGCAGGTGGGTGTAGAGCGTGGAGCCC |
| | | AGTCCCGTCCGCTGGTGGCGGGGGGAGACGTA |
| | | CACGGTCGACTCGGCCGTCCAGTCGTAGGCGTT |
| | | GCGTGCCTTCCAGGGGCCCGCGTAGGCGATGCC |
| | | GGCGACCTCGCCGTCCACCTCGGCGACGAGCCA |
| | | GGGATAGCGCTCCCGCAGACGGACGAGGTCGTC |
| | | CGTCCACTCCTGCGGTTCCTGCGGCTCGGTACG |
| | | GAAGTTGACCGTGCTTGTCTCGATGTAGTGGTT |
| | | GACGATGGTGCAGACCGCCGGCATGTCCGCCTC |
| | | GGTGGCACGGCGGATGTCGGCCGGGCGTCGTT |
| | | CTGGGCTCATGGTAGATCCCCCGTTCGTAAATG |
| | | GTGAAAATTTTCAGAAAATTGCTTTTGCTTTAAA |
| | | AGAAATGATTTAAATTGCTGCAATAGAAGTAGA |
| | | ATGCTTGATTGCTTGAGATTCGTTTGTTTTGTAT |
| | | ATGTTGTGTTGAGAATTAATTCTCGAGGTCCTCT |
| | | CCAAATGAAATGAACTTCCTTATATAGAGGAAG |
| | | GGTCTTGCGAAGGATAGTGGGATTGTGCGTCAT |
| | | CCCTTACGTCAGTGGAGATATCACATCAATCCA |
| | | CTTGCTTTGAAGACGTGGTTGGAACGTCTTCTTT |
| | | TTCCACGATGCTCCTCGTGGGTGGGGGTCCATC |
| | | TTTGGGACCACTGTCGGCAGAGGCATCTTCAAC |
| | | GATGGCCTTTCCTTTATCGCAATGATGGCATTTG |
| | | TAGGAGCCACCTTCCTTTTCCACTATCTTCACAA |
| | | TAAAGTGACAGATAGCTGGGCAATGGAATCCGA |
| | | GGAGGTTTCCGGATATTACCCTTTGTTGAAAAG |
| | | TCTCAATTGCCCTTTGGTCTTCTGAGACTGTATC |
| | | TTTGATATTTTTGGAGTAGACAAGTGTGTCGTGC |
| | | TCCACCATGTTATCACATCAATCCACTTGCTTTG |
| | | AAGACGTGGTTGGAACGTCTTCTTTTTCCACGAT |
| | | GCTCCTCGTGGGGGGGGTCCATCTTTGGGACC |
| | | ACTGTCGGCAGAGGCATCTTCAACGATGGCCTT |
| | | TCCTTTATCGCAATGATGGCATTTGTAGGAGCC |
| | | ACCTTCCTTTTCCACTATCTTCACAATAAAGTGA |
| | | CAGATAGCTGGGCAATGGAATCCGAGGAGGTTT |
| | | CCGGATATTACCCTTTGTTGAAAAGTCTCAATTG |
| | | CCCTTTGGTCTTCTGAGACTGTATCTTTGATATT |
| | | TTTGGAGTAGACAAGTGTGTCGTGCTCCACCAT |
| | | GTTGACCTGCAGACTAGTCACTATTTTCAGAAG |

-continued

| SEQ ID | Brief reference | nt |
|---|---|---|
| | | AAGTTCCCAATAGTAGTCCAAAATTTTTGTAACG<br>AAGGGAGCATAATAGTTACATGCAAAGGAAAAC<br>TGCCATTCTTTAGAGGGGATGCTTGTTTAAGAA<br>CAAAAAATATATCACTTTCTTTTGTTCCAAGTCA<br>TTGCGTATTTTTTTAAAAATATTTGTTCCTTCGT<br>ATATTTCGAGCTTCAATCACTTTATGGTTCTTTG<br>TATTCTGGCTTTGCTGTAAATCGTAGCTAACCTT<br>CTTCCTAGCAGAAATTATTAATACTTGGGATATT<br>TTTTTAGAATCAAGTAAATTACATATTACCACCA<br>CATCGAGCTGCTTTTAAATTCATATTACAGCCAT<br>ATAGGCTTGATTCATTTTGCAAAATTTCCAGGAT<br>ATTGACAACGTTAACTTAATAATATCTTGAAATA<br>TTAAAGCTATTATGATTAGGGGTGCAAATGGAC<br>CGAGTTGGTGGTGTAAATATATGAGCTCCCATT<br>TTATTTATTGCTCCCATTTTATTTATTTTAGTTTG<br>TGTGACAGATGAACATTATTAGGAGGAAAGGTA<br>TAAGCAGGGTTTAACTGTCACAGGGAAGGTGGT<br>TTTGGGAGTCTAAAGCTTCAATGATACTTGTGA<br>GCAAGAGCATTTGCTACGCCGGCAACAACCTTC<br>TGAAATGCAGCCTGCACATTAGGGTTGAAATCA<br>TGACCAAGTCTACGGGCTAGGACTACAACAATG<br>ACGTTGCCGAGTAGGCGAAAATTTTCAGGGTCG<br>ACGTGAAGTTGATCACAATGCAACTCAGATAAC<br>TTCGCAAAAGTACCTTTCAGGTTGTCCAAATGCT<br>TCAGCCCATCAGAGAATGATTGCAATACTTTCTT<br>TCCATGAGCTTTCACTTTTGGATTTCCCATAACA<br>GCATCTGCATTGGACAAATCACCAAAGCTCTCA<br>AAGAATCTTTGTGTCCAGGGGTAAACCACAAGG<br>AGCCTCCCAAGTGCCTCTCCACCAACTTCATCAA<br>CATTAACTTTTCCCCACAACCCTAACACTGCTTC<br>CTTTTCCTCAGCACTGAGGTGCACACTTCCTCCA<br>CCTCCAGATCCTCCACCTCCTGATCCTCCACCTC<br>CTGATCCTCCACCTCCACTCCTATATTTGCTGGT<br>GAGTACAGTTGAGACGTTGGCGAGGAACTTGTC<br>CAAACTGGCATGCACAGAAGGATTAAAATCATC<br>TGGATGGTGGGCGGCTAAAGTGACTAACAAACA<br>ATGGGACAGCAGCTTGAAATTTACCGGATCAAC<br>TCTCAATTTGTGTGCATGAAGATCAGATAATGCA<br>GAAAGTGCGCCGGGAAGGTCATCCAAGTGCCCA<br>ACAGCTTTTGTCAAAGCATCAGCCACCTTCTGCC<br>CATGTGCCTTCACTTGATCACTTCCATGTGAGAG<br>GTTGAAATGAGGAAAGTAAGTCTTTGTCGTTGG<br>AAAGCCAAGAAACATACGCTCAAGAGCTTCAGC<br>ACCGTGCGCTCCAGCTTGACCACCAACTTTTCC<br>CCAAGCAGCCTTAACATTTGCTTTGTCTGCTGCC<br>GATAGAACCATGGATCCGGCTATCGTTCGTAAA<br>TGGTGAAAATTTTCAGAAAATTGCTTTTGCTTTA<br>AAAGAAATGATTTAAATTGCTGCAATAGAAGTA<br>GAATGCTTGATTGCTTGAGATTCGTTTGTTTTGT<br>ATATGTTGTGTTGAGAATTGTTGTGTTAGAGAG<br>CTACAATATATAGAGAAAGATCACCGTTTGGCT<br>AGCTTTAAGTGGCTAAGTGTGAACGGGATGAGA<br>TTCTCTTTTCTTTTGGCCGTGTTGGTCACAAGAT<br>TGGACGTCGACGTGTTTGAGGCTTGTGAAATTT<br>CCAGAAGCAAAGAAAGGATAAACTTGAGTTAAC<br>ATGCAATGGGGAGAAAAACAAAGGGTTGGTGAG<br>TGTGAGGGGTACTTGGCAGCTGAGAACAATGCT<br>TTAGTTGCATGCCATGCAGATTTCATCCGTTTGA<br>AACTCTGTAAAGGACGTGTGGATCGAGTTCGCG<br>TGAGCAGCTAGCTTGGCTTGGATTTTTGTCTTGC<br>TATCCCTCTACTACATTAATTTCCCTACATGCAA<br>CTGTTTCATGACATTTTCGTGTATCTCCCAACTG<br>GCTAGCTCATATTAACTAAGGAAAATAGAATTCT<br>AATGGAAAATTTAAATAATAGACTTTCATATTTT<br>ATTTGTCCCCCTCAAATTTTTTACATTTCATTTTT<br>TCGATTTTATTCTATTTATTTTTTTATTCTTTTTT<br>TAAAAATTGGCATTCTAAACCCTATATATTATAT<br>GAAATAATATATTTTTTAACAAACTCTTTATTAT<br>TCATCAAAATTATAAATGCATGAATGAAGTATTA<br>TATAAGAAGTGAAACTTATAAAATTATGTAATTT<br>ATAATAAGTTTCAAGTACGCGTGTTCACCAACAA<br>AATCACGTGAAAAATTGAACAAAAGACGCAAAA<br>GCAAGACCAAGTAGCCTCCTGAGTGATGCGCTT<br>CAACTGTTGCAAACACTAACCTAAACATAGACG<br>GCTTCTAGGGTGCGCAAAGTTGAAATGTGAGGC<br>ACGGTACACAAGTTTTTTTAGGACCGTTGGATAT<br>AACACTTAATTAGTTAACGGTGCAAATCTCCAAG |

-continued

| SEQ ID | Brief reference | nt |
|---|---|---|
| | | ATTTTAGAAGTGGAAAAAGTATTGAATAAAAAA GTATCGCATTTACTGTAGAGCAAACTCTTATTTT AATATTGTTGGGTCACGTGGGTGTGGGCTTCTC GACTCCACCGGATGATGTTTTCAATTTTGATTTC TTTTTTTTCCTAAAGGTTTTCCATTTACATTTATT TTGGTTAGAAAAAAGAATAAGGCTAAATGTCTA AACCAACTTGCATTCGAACCTAGAACTAAAATAA TCTACCACCACGCCATCATCAACTTTATACTTTT GAAAAGTATTTATAACAATATATATATTTTTATCA AACATGCTTAATTGCCTTAAAATAAAATTTATAA ATTAGTTGGTAATATTTTAACAATATTAACGGAT TTCTGGTAAAAAAAAATAAAATCATGAATTTCTA AAATTTTAAAATCAAATTTTTTAATGTATAGATT ATTTTATCTAGAGAATTCGTAATCATGTCATAGC TGTTTCCTGTGTGAAATTGTTATCCGCTCACAAT TCCACACAACATACGAGCCGGAAGCATAAAGTG TAAAGCCTGGGGTGCCTAATGAGTGAGCTAACT CACATTAATTGCGTTGCGCTCACTGCCCGCTTTC CAGTCGGGAAACCTGTCGTGCCAGCTGCATTAA TGAATCGGCCAACGCGCGGGGAGAGGCGGTTT GCGTATTGGAGCTTGAGCTTGGATCAGATTGTC GTTTCCCGCCTTCAGTTTAAACTATCAGTGTTTG ACAGGATATATTGGCGGGTAAAC 3' |
| SEQ ID NO: 5 | 35S + TEV + myoglobincDNA + NOS | 5' aataatGCGGCCGCATGGTGGAGCACGACACTCTC GTCTACTCCAAGAATATCAAAGATACAGTCTCA GAAGACCAAAGGGCTATTGAGACTTTTCAACAA AGGGTAATATCGGGAAACCTCCTCGGATTCCAT TGCCCAGCTATCTGTCACTTCATCAAAAGGACA GTAGAAAAGGAAGGTGGCACCTACAAATGCCAT CATTGCGATAAAGGAAAGGCTATCGTTCAAGAT GCCTCTGCCGACAGTGGTCCCAAAGATGGACCC CCACCCACGAGGAGCATCGTGGAAAAAGAAGAC GTTCCAACCACGTCTTCAAAGCAAGTGGATTGA TGTGATAACATGGTGGAGCACGACACTCTCGTC TACTCCAAGAATATCAAAGATACAGTCTCAGAA GACCAAAGGGCTATTGAGACTTTTCAACAAAGG GTAATATCGGGAAACCTCCTCGGATTCCATTGC CCAGCTATCTGTCACTTCATCAAAAGGACAGTA GAAAAGGAAGGTGGCACCTACAAATGCCATCAT TGCGATAAAGGAAAGGCTATCGTTCAAGATGCC TCTGCCGACAGTGGTCCCAAAGATGGACCCCCA CCCACGAGGAGCATCGTGGAAAAAGAAGACGTT CCAACCACGTCTTCAAAGCAAGTGGATTGATGT GATATCTCCACTGACGTAAGGGATGACGCACAA TCCCACTATCCTTCGCAAGACCTTCCTCTATATA AGGAAGTTCATTTCATTTGGAGAGGACACGCTG AAATCACCAGTCTCTCTCTACAAATCTATCTCTG AATTAATTCTCAACACAACATATACAAAACAAAC GAATCTCAAGCAATCAAGCATTCTACTTCTATTG CAGCAATTTAAATCATTTCTTTTAAAGCAAAAGC AATTTTCTGAAAATTTTCACCATTTACGAACGAT AGATGGGGCTATCAGATGGTGAATGGCAACTTG TATTGAATGTTTGGGGAAAAGTTGAAGCTGATG TTGCTGGACATGGTCAAGAAGTGTTAATAAGAC TCTTCAAAGGCCACCCTGAAACATTAGAGAAGT TTGACAAATTCAAGCACCTAAAATCTGAAGATG AAATGAAGGCCTCCGAGGACTTGAAGAAGCATG GAAACACTGTCCTGACTGCACTCGGCGGGATCC TCAAAAAGAAAGGTCATCATGAAGCGGAGTTGA CACCATTGGCTCAGTCTCATGCTACCAAACACA AGATTCCTGTGAAGTATCTTGAGTTTATTAGTGA GGCCATAATTCAGGTTTTGCAATCAAAACATCCC GGTGATTTTGGTGCAGATGCTCAAGGAGCAATG AGCAAAGCACTGGAGCTTTTCAGGAATGATATG GCAGCCAAGTACAAGGAACTTGGATTTCAGGGG TGAGATCGTTCAAACATTTGGCAATAAAGTTTCT TAAGATTGAATCCTGTTGCCGGTCTTGCGATGA TTATCATATAATTTCTGTTGAATTACGTTAAGCA TGTAATAATTAACATGTAATGCATGACGTTATTT ATGAGATGGGTTTTTATGATTAGAGTCCCGCAA TTATACATTTAATACGCGATAGAAAACAAAATAT AGCGCGCAAACTAGGATAAATTATCGCGCGCGG TGTCATCTATGTTACTAGATCGGCGGCCGCttatta 3' |

-continued

| SEQ ID | Brief reference | nt |
|---|---|---|
| SEQ ID NO: 6 | p7S + TEV + myoglobincDNA + arc5 + Rb7MAR | 5'<br>aaatttGCGGCCGCGGTACTTGGCAGCTGAGAACA<br>ATGCTTTAGTTGCATGCCATGCAGATTTCATCCG<br>TTTGAAACTCTGTAAAGGACGTGTGGATCGAGT<br>TCGCGTGAGCAGCTAGCTTGGCTTGGATTTTTG<br>TCTTGCTATCCCTCTACTACATTAATTTCCCTAC<br>ATGCAACTGTTTCATGACATTTTCGTGTATCTCC<br>CAACTGGCTAGCTCATATTAACTAAGGAAAATA<br>GAATTCTAATGGAAAATTTAAATAATAGACTTTC<br>ATATTTTATTTGTCCCCCTCAAATTTTTTACATTT<br>CATTTTTTCGATTTTATTCTATTTATTTTTTTATT<br>CTTTTTTTAAAAATTGGCATTCTAAACCCTATAT<br>ATTATATGAAATAATATATTTTTTAACAAACTCT<br>TTATTATTCATCAAAATTATAAATGCATGAATGA<br>AGTATTATATAAGAAGTGAAACTTATAAAATTAT<br>GTAATTTATAATAAGTTTCAAGTACGCGTGTTCA<br>CCAACAAAATCACGTGAAAAATTGAACAAAAGA<br>CGCAAAAGCAAGACCAAGTAGCCTCCTGAGTGA<br>TGCGCTTCAACTGTTGCAAACACTAACCTAAACA<br>TAGACGGCTTCTAGGGTGCGCAAAGTTGAAATG<br>TGAGGCACGGTACACAAGTTTTTTTAGGACCGT<br>TGGATATAACACTTAATTAGTTAACGGTGCAAAT<br>CTCCAAGATTTTAGAAGTGGAAAAAGTATTGAA<br>TAAAAAAGTATCGCATTTACTGTAGAGCAAACTC<br>TTATTTTAATATTGTTGGGTCACGTGGGTGTGG<br>GCTTCTCGACTCCACCGGATGATGTTTTCAATTT<br>TGATTTCTTTTTTTTGCTAAAGGTTTTCCATTTA<br>CATTTATTTTGGTTAGAAAAAAGAATAAGGCTAA<br>ATGCCTAAACCAACTTGCATTCGAACCTAGAACT<br>AAAATAATCTACCACCACGCCATCATCAACTTTA<br>TACTTTTGAAAAGTATTTATAACAATATATATAT<br>TTTATCAAACATGCTTAATTGCCTTAAAATAAAA<br>TTTATAAATTAGTTGGTAATATTTTAACAATATT<br>AACAAATTTCTGGTAAAAAAATTAAAATCATGAA<br>TTTCTAAAATTTTAAAATCAAATTTTTTAATGTAT<br>AGGTTATTTTAATTTAATTTATATTGTTAAAAAT<br>GGGTTATTACAATTTAATTAATCTCTAATTAAAA<br>TATATATGAGGATATTAGTTTTATTCTAATACTA<br>TTGTAATTCCCATTCATATGAATATATATATATG<br>AGATTGTTTGATAAAATAATCTCAATAAATGTTT<br>CAACTATGCAAAGCATAATGAGCATCTAACTTAT<br>TTACAATTTACAATAATAAATCATGATCAAAACA<br>AACATCAACACTAACTCGTTATTAGTATGTTATC<br>AACAAATGTAAAGGTGAAGCTACTCTAGCTTAA<br>GTCAAAGTTAAATTATTCTGATCAGAAACTCTTT<br>GAAAATATACCTAATAAAACTCAAGAAAATACAC<br>ACCTAATATAAACATATGTTGAACATCTTTATAC<br>ATGTGCATCTTCAAACCCCTATTCATTCCATCTA<br>TTGTGTCTCCAAGAAGGAGATCCAACCTATAAG<br>TCATTTCCTCCCATGTACGTCATGTATAGGATCA<br>TTACAGTCACAGCCACATGTGTTATATGCAAGG<br>ATTTAATTAGTAGTGTAAAAACTTGAGTGGAATC<br>CTTCAAGGATTAGAAAGAGAAACTAAGGTAAAT<br>TAAGAGATTTACTGAATCAATATAAATCTTTTGT<br>TTTTACTCGAGCTTCTATTATACTTGTTTTATCTT<br>AGTTGCTTCTATCTTACTTTCGATGTTTAAATTT<br>TGAGAAAAAAATCCTTTTGTGAAAAACCTTTTTA<br>AAAAGTTGTTTGACGCTACCGTACAGAGCATCC<br>ATTTTTAATTTGTGGTCAAATTTGCTTTGTGAAA<br>ATCTTCATCTTACAAAAAAAAAACCTTAATTTAA<br>ATCTCATCTAACATATTGAATTAATTCTCAACAC<br>AACATATACAAAACAAACGAATCTCAAGCAATC<br>AAGCATTCTACTTCTATTGCAGCAATTTAAATCA<br>TTTCTTTTAAAGCAAAAGCAATTTTCTGAAAATT<br>TTCACCATTTACGAACGATAGATGGGGCTATCA<br>GATGGTGAATGGCAACTTGTATTGAATGTTTGG<br>GGAAAAGTTGAAGCTGATGTTGCTGGACATGGT<br>CAAGAAGTGTTAATAAGACTCTTCAAAGGCCAC<br>CCTGAAACATTAGAGAAGTTTGACAAATTCAAG<br>CACCTAAAATCTGAAGATGAAATGAAGGCCTCC<br>GAGGACTTGAAGAAGCATGGAAACACTGTCCTG<br>ACTGCACTCGGCGGGATCCTCAAAAAGAAAGGT<br>CATCATGAAGCGGAGTTGACACCATTGGCTCAG<br>TCTCATGCTACCAAACACAAGATTCCTGTGAAGT<br>ATCTTGAGTTTATTAGTGAGGCCATAATTCAGGT<br>TTTGCAATCAAAACATCCCGGTGATTTTGGTGCA |

-continued

| SEQ ID | Brief reference | nt |
|---|---|---|
| | | GATGCTCAAGGAGCAATGAGCAAAGCACTGGAG<br>CTTTTCAGGAATGATATGGCAGCCAAGTACAAG<br>GAACTTGGATTTCAGGGGTGATAGACTCCCAAA<br>ACCACCTTCCCTGTGACAGTTAAACCCTGCTTAT<br>ACCTTTCCTCCTAATAATGTTCATCTGTCACACA<br>AACTAAAATAAATAAAATGGGAGCAATAAATAA<br>AATGGGAGCTCATATATTTACACCACCAACTCG<br>GTCCATTTGCACCCCTAATCATAATAGCTTTAAT<br>ATTTCAAGATATTATTAAGTTAACGTTGTCAATA<br>TCCTGGAAATTTTGCAAAATGAATCAAGCCTATA<br>TGGCTGTAATATGAATTTAAAAGCAGCTCGATG<br>TGGTGGTAATATGTAATTTACTTGATTCTAAAAA<br>AATATCCCAAGTATTAATAATTTCTGCTAGGAAG<br>AAGGTTAGCTACGATTTACAGCAAAGCCAGAAT<br>ACAAAGAACCATAAAGTGATTGAAGCTCGAAAT<br>ATACGAAGGAACAAATATTTTTAAAAAAATACGC<br>AATGACTTGGAACAAAAGAAAGTGATATATTTTT<br>TGTTCTTAAACAAGCATCCCCTCTAAAGAATGGC<br>AGTTTTCCTTTGCATGTAACTATTATGCTCCCTT<br>CGTTACAAAAATTTTGGACTACTATTGGGAACTT<br>CTTCTGAAAATAGTGGCGGCCGCttaata<br>3' |
| SEQ ID NO: 7 | PPhas + myoglobincDNA + arc5 + Rb7MAR | 5'<br>aaatttGCGGCCGCCATTGTACTCCCAGTATCATTA<br>TAGTGAAAGTTTTGGCTCTCTCGCCGGTGGTTTT<br>TTACCTCTATTTAAAGGGGTTTTCCACCTAAAAA<br>TTCTGGTATCATTCTCACTTTACTTGTTACTTTA<br>ATTTCTCATAATCTTTGGTTGAAATTATCACGCT<br>TCCGCACACGATATCCCTACAAATTTATTATTTG<br>TTAAACATTTTCAAACCGCATAAAATTTTATGAA<br>GTCCCGTCTATCTTTAATGTAGTCTAACATTTTC<br>ATATTGAAATATATAATTTACTTAATTTTAGCGT<br>TGGTAGAAAGCATAAAGATTTATTCTTATTCTTC<br>TTCATATAAATGTTTAATATACAATATAAACAAA<br>TTCTTTACCTTAAGAAGGATTTCCCATTTTATAT<br>TTTAAAAATATATTTATCAAATATTTTTCAACCA<br>CGTAAATCTCATAATAATAAGTTGTTTCAAAAGT<br>AATAAAATTTAACTCCATAATTTTTTTATTCGAC<br>TGATCTTAAAGCAACACCCAGTGACACAACTAG<br>CCATTTTTTTCTTTGAATAAAAAAATCCAATTAT<br>CATTGTATTTTTTTTATACAATGAAAATTTCACC<br>AAACAATCATTTGTGGTATTTCTGAAGCAAGTCA<br>TGTTATGCAAAATTCTATAATTCCCATTTGACAC<br>TACGGAAGTAACTGAAGATCTGCTTTTACATGC<br>GAGACACATCTTCTAAAGTAATTTTAATAATAGT<br>TACTATATTCAAGATTTCATATATCAAATACTCA<br>ATATTACTTCTAAAAAATTAATTAGATATAATTA<br>AAATATTACTTTTTTAATTTTAAGTTTAATTGTTG<br>AATTTGTGACTATTGATTTATTATTCTACTATGT<br>TTAAATTGTTTTATAGATAGTTTAAAGTAAATAT<br>AAGTAATGTAGTAGAGTGTTAGAGTGTTACCCT<br>AAACCATAAACTATAACATTTATGGTGGACTAAT<br>TTTCATATATTTCTTATTGCTTTTACCTTTTCTTG<br>GTATGTAAGTCCGTAACTAGAATTACAGTGGGT<br>TGCCATGGCACTCTGTGGTCTTTTGGTTCATGCA<br>TGGGTCTTGCGCAAGAAAAAGACAAAGAACAAA<br>GAAAAAAGACAAAACAGAGAGACAAAACGCAAT<br>CACACAACCAACTCAAATTAGTCACTGGCTGAT<br>CAAGATCGCCGCGTCCATGTATGTCTAAATGCC<br>ATGCAAAGCAACACGTGCTTAACATGCACTTTA<br>AATGGCTCACCCATCTCAACCCACACACAAACA<br>CATTGCCTTTTTCTTCATCATCACCACAACCACC<br>TGTATATATTCATTCTCTTCCGCCACCTCAATTT<br>CTTCACTTCAACACACGTCAACCTGCATATGCGT<br>GTCATCCCATGCCCAAATCTCCATGCATGTTCCA<br>ACCACCTTCTCTCTTATATAATACCTATAAATAC<br>CTCTAATATCACTCACTTCTTTCATCATCCATCC<br>ATCCAGAGTACTACTACTCTACTACTATAATACC<br>CCAACCCAACTCATATTCAATACTACTCTACTAT<br>GGGGCTATCAGATGGTGAATGGCAACTTGTATT<br>GAATGTTTGGGGAAAAGTTGAAGCTGATGTTGC<br>TGGACATGGTCAAGAAGTGTTAATAAGACTCTT<br>CAAAGGCCACCCTGAAACATTAGAGAAGTTTGA<br>CAAATTCAAGCACCTAAAATCTGAAGATGAAAT<br>GAAGGCCTCCGAGGACTTGAAGAAGCATGGAAA<br>CACTGTCCTGACTGCACTCGGCGGGATCCTCAA |

-continued

| SEQ ID | Brief reference | nt |
|---|---|---|
| | | AAAGAAAGGTCATCATGAAGCGGAGTTGACACC ATTGGCTCAGTCTCATGCTACCAAACACAAGATT CCTGTGAAGTATCTTGAGTTTATTAGTGAGGCC ATAATTCAGGTTTTGCAATCAAAACATCCCGGTG ATTTTGGTGCAGATGCTCAAGGAGCAATGAGCA AAGCACTGGAGCTTTTCAGGAATGATATGGCAG CCAAGTACAAGGAACTTGGATTTCAGGGGTGAT AGACTCCCAAAACCACCTTCCCTGTGACAGTTA AACCCTGCTTATACCTTTCCTCCTAATAATGTTC ATCTGTCACACAAACTAAAATAAATAAAATGGG AGCAATAAATAAAATGGGAGCTCATATATTTACA CCACCAACTCGGTCCATTTGCACCCCTAATCATA ATAGCTTTAATATTTCAAGATATTATTAAGTTAA CGTTGTCAATATCCTGGAAATTTTGCAAAATGAA TCAAGCCTATATGGCTGTAATATGAATTTAAAAG CAGCTCGATGTGGTGGTAATATGTAATTTACTTG ATTCTAAAAAAATATCCCAAGTATTAATAATTTC TGCTAGGAAGAAGGTTAGCTACGATTTACAGCA AAGCCAGAATACAAAGAACCATAAAGTGATTGA AGCTCGAAATATACGAAGGAACAAATATTTTTAA AAAAATACGCAATGACTTGGAACAAAAGAAAGT GATATATTTTTTGTTCTTAAACAAGCATCCCCTC TAAAGAATGGCAGTTTTCCTTTGCATGTAACTAT TATGCTCCCTTCGTTACAAAAATTTTGGACTACT ATTGGGAACTTCTTCTGAAAATAGTGGCGGCCG Cttaaat 3' |
| SEQ ID NO: 8 | 2x 35S promoter | 5' ATGGTGGAGCACGACACTCTCGTCTACTCCAAG AATATCAAAGATACAGTCTCAGAAGACCAAAGG GCTATTGAGACTTTTCAACAAAGGGTAATATCG GGAAACCTCCTCGGATTCCATTGCCCAGCTATC TGTCACTTCATCAAAAGGACAGTAGAAAAGGAA GGTGGCACCTACAAATGCCATCATTGCGATAAA GGAAAGGCTATCGTTCAAGATGCCTCTGCCGAC AGTGGTCCCAAAGATGGACCCCCACCCACGAGG AGCATCGTGGAAAAAGAAGACGTTCCAACCACG TCTTCAAAGCAAGTGGATTGATGTGATAACATG GTGGAGCACGACACTCTCGTCTACTCCAAGAAT ATCAAAGATACAGTCTCAGAAGACCAAAGGGCT ATTGAGACTTTTCAACAAAGGGTAATATCGGGA AACCTCCTCGGATTCCATTGCCCAGCTATCTGTC ACTTCATCAAAAGGACAGTAGAAAAGGAAGGTG GCACCTACAAATGCCATCATTGCGATAAAGGAA AGGCTATCGTTCAAGATGCCTCTGCCGACAGTG GTCCCAAAGATGGACCCCCACCCACGAGGAGCA TCGTGGAAAAAGAAGACGTTCCAACCACGTCTT CAAAGCAAGTGGATTGATGTGATATCTCCACTG ACGTAAGGGATGACGCACAATCCCACTATCCTT CGCAAGACCTTCCTCTATATAAGGAAGTTCATTT CATTTGGAGAGGACACGCTGAAATCACCAGTCT CTCTCTACAAATCTATCTCT 3' |
| SEQ ID NO: 9 | TEV | 5' GAATTAATTCTCAACACAACATATACAAAACAAA CGAATCTCAAGCAATCAAGCATTCTACTTCTATT GCAGCAATTTAAATCATTTCTTTTAAAGCAAAAG CAATTTTCTGAAAATTTTCACCATTTACGAACGA TAG 3' |
| SEQ ID NO: 10 | NOS terminator | 5' GATCGTTCAAACATTTGGCAATAAAGTTTCTTAA GATTGAATCCTGTTGCCGGTCTTGCGATGATTAT CATATAATTTCTGTTGAATTACGTTAAGCATGTA ATAATTAACATGTAATGCATGACGTTATTTATGA GATGGGTTTTTATGATTAGAGTCCCGCAATTATA CATTTAATACGCGATAGAAAACAAAATATAGCG CGCAAACTAGGATAAATTATCGCGCGCGGTGTC ATCTATGTTACTAGATC 3' |

-continued

| SEQ ID | Brief reference | nt |
|---|---|---|
| SEQ ID NO: 11 | 7S promoter | 5'<br>GGTACTTGGCAGCTGAGAACAATGCTTTAGTTG<br>CATGCCATGCAGATTTCATCCGTTTGAAACTCTG<br>TAAAGGACGTGTGGATCGAGTTCGCGTGAGCAG<br>CTAGCTTGGCTTGGATTTTTGTCTTGCTATCCCT<br>CTACTACATTAATTTCCCTACATGCAACTGTTTC<br>ATGACATTTTCGTGTATCTCCCAACTGGCTAGCT<br>CATATTAACTAAGGAAAATAGAATTCTAATGGAA<br>AATTTAAATAATAGACTTTCATATTTTATTTGTC<br>CCCCTCAAATTTTTTACATTTCATTTTTTCGATTT<br>TATTCTATTTATTTTTTTATTCTTTTTTTAAAAAT<br>TGGCATTCTAAACCCTATATATTATATGAAATAA<br>TATATTTTTTAACAAACTCTTTATTATTCATCAAA<br>ATTATAAATGCATGAATGAAGTATTATATAAGAA<br>GTGAAACTTATAAAATTATGTAATTTATAATAAG<br>TTTCAAGTACGCGTGTTCACCAACAAAATCACGT<br>GAAAAATTGAACAAAAGACGCAAAAGCAAGACC<br>AAGTAGCCTCCTGAGTGATGCGCTTCAACTGTT<br>GCAAACACTAACCTAAACATAGACGGCTTCTAG<br>GGTGCGCAAAGTTGAAATGTGAGGCACGGTACA<br>CAAGTTTTTTTAGGACCGTTGGATATAACACTTA<br>ATTAGTTAACGGTGCAAATCTCCAAGATTTTAGA<br>AGTGGAAAAAGTATTGAATAAAAAAGTATCGCA<br>TTTACTGTAGAGCAAACTCTTATTTTAATATTGT<br>TGGGTCACGTGGGTGTGGGCTTCTCGACTCCAC<br>CGGATGATGTTTTCAATTTTGATTTCTTTTTTTT<br>GCTAAAGGTTTTCCATTTACATTTATTTTGGTTA<br>GAAAAAAGAATAAGGCTAAATGCCTAAACCAAC<br>TTGCATTCGAACCTAGAACTAAAATAATCTACCA<br>CCACGCCATCATCAACTTTATACTTTTGAAAAGT<br>ATTTATAACAATATATATATTTTATCAAACATGC<br>TTAATTGCCTTAAAATAAAATTTATAAATTAGTT<br>GGTAATATTTTAACAATATTAACAAATTTCTGGT<br>AAAAAAATTAAAATCATGAATTTCTAAAATTTTA<br>AAATCAAATTTTTTAATGTATAGGTTATTTTAAT<br>TTAATTTATATTGTTAAAAAATGGGTTATTACAAT<br>TTAATTAATCTCTAATTAAAATATATATGAGGAT<br>ATTAGTTTTATTCTAATACTATTGTAATTCCCAT<br>TCATATGAATATATATATATGAGATTGTTTGATA<br>AAATAATCTCAATAAATGTTTCAACTATGCAAAG<br>CATAATGAGCATCTAACTTATTTACAATTTACAA<br>TAATAAATCATGATCAAAACAAACATCAACACTA<br>ACTCGTTATTAGTATGTTATCAACAAATGTAAAG<br>GTGAAGCTACTCTAGCTTAAGTCAAAGTTAAATT<br>ATTCTGATCAGAAACTCTTTGAAAATATACCTAA<br>TAAAACTCAAGAAAATACACACCTAATATAAACA<br>TATGTTGAACATCTTTATACATGTGCATCTTCAA<br>ACCCCTATTCATTCCATCTATTGTGTCTCCAAGA<br>AGGAGATCCAACCTATAAGTCATTTCCTCCCATG<br>TACGTCATGTATAGGATCATTACAGTCACAGCC<br>ACATGTGTTATATGCAAGGATTTAATTAGTAGTG<br>TAAAAACTTGAGTGGAATCCTTCAAGGATTAGA<br>AAGAGAAACTAAGGTAAATTAAGAGATTTACTG<br>AATCAATATAAATCTTTTGTTTTTACTCGAGCTT<br>CTATTATACTTGTTTTATCTTAGTTGCTTCTATCT<br>TACTTTCGATGTTTAAATTTTGAGAAAAAAATCC<br>TTTTGTGAAAAACCTTTTTAAAAAGTTGTTTGAC<br>GCTACCGTACAGAGCATCCATTTTTAATTTGTGG<br>TCAAATTTGCTTTGTGAAAATCTTCATCTTACAA<br>AAAAAAAACCTTAATTTAAATCTCATCTAACATA<br>TT<br>3' |
| SEQ ID NO: 12 | Arc5 Terminator | 5'<br>TAGACTCCCAAAACCACCTTCCCTGTGACAGTTA<br>AACCCTGCTTATACCTTTCCTCCTAATAATGTTC<br>ATCTGTCACACAAACTAAAATAAATAAAATGGG<br>AGCAATAAATAAAATGGGAGCTCATATATTTACA<br>CCA<br>3' |
| SEQ ID NO: 13 | Rb7 Mar | 5'<br>CCAACTCGGTCCATTTGCACCCCTAATCATAATA<br>GCTTTAATATTTCAAGATATTATTAAGTTAACGT<br>TGTCAATATCCTGGAAATTTTGCAAAATGAATCA<br>AGCCTATATGGCTGTAATATGAATTTAAAAGCA |

| SEQ ID | Brief reference | nt |
| --- | --- | --- |
| | | GCTCGATGTGGTGGTAATATGTAATTTACTTGAT<br>TCTAAAAAAATATCCCAAGTATTAATAATTTCTG<br>CTAGGAAGAAGGTTAGCTACGATTTACAGCAAA<br>GCCAGAATACAAAGAACCATAAAGTGATTGAAG<br>CTCGAAATATACGAAGGAACAAATATTTTTAAAA<br>AAATACGCAATGACTTGGAACAAAAGAAAGTGA<br>TATATTTTTTGTTCTTAAACAAGCATCCCCTCTA<br>AAGAATGGCAGTTTTCCTTTGCATGTAACTATTA<br>TGCTCCCTTCGTTACAAAAATTTTGGACTACTAT<br>TGGGAACTTCTTCTGAAAATAGTG<br>3' |
| SEQ ID<br>NO: 14 | Phas promoter | 5'<br>CATTGTACTCCCAGTATCATTATAGTGAAAGTTT<br>TGGCTCTCTCGCCGGTGGTTTTTTACCTCTATTT<br>AAAGGGGTTTTCCACCTAAAAATTCTGGTATCAT<br>TCTCACTTTACTTGTTACTTTAATTTCTCATAATC<br>TTTGGTTGAAATTATCACGCTTCCGCACACGATA<br>TCCCTACAAATTTATTATTTGTTAAACATTTTCA<br>AACCGCATAAAATTTTATGAAGTCCCGTCTATCT<br>TTAATGTAGTCTAACATTTTCATATTGAAATATA<br>TAATTTACTTAATTTTAGCGTTGGTAGAAAGCAT<br>AAAGATTTATTCTTATTCTTCTTCATATAAATGT<br>TTAATATACAATATAAACAAATTCTTTACCTTAA<br>GAAGGATTTCCCATTTTATATTTTAAAAATATAT<br>TTATCAAATATTTTTCAACCACGTAAATCTCATA<br>ATAATAAGTTGTTTCAAAAGTAATAAAATTTAAC<br>TCCATAATTTTTTTATTCGACTGATCTTAAAGCA<br>ACACCCAGTGACACAACTAGCCATTTTTTTCTTT<br>GAATAAAAAAATCCAATTATCATTGTATTTTTTT<br>TATACAATGAAAATTTCACCAAACAATCATTTGT<br>GGTATTTCTGAAGCAAGTCATGTTATGCAAAATT<br>CTATAATTCCCATTTGACACTACGGAAGTAACTG<br>AAGATCTGCTTTTACATGCGAGACACATCTTCTA<br>AAGTAATTTTAATAATAGTTACTATATTCAAGAT<br>TTCATATATCAAATACTCAATATTACTTCTAAAA<br>AATTAATTAGATATAATTAAAATATTACTTTTTT<br>AATTTTAAGTTTAATTGTTGAATTTGTGACTATT<br>GATTTATTATTCTACTATGTTTAAATTGTTTTATA<br>GATAGTTTAAAGTAAATATAAGTAATGTAGTAGA<br>GTGTTAGAGTGTTACCCTAAACCATAAACTATAA<br>CATTTATGGTGGACTAATTTTCATATATTTCTTA<br>TTGCTTTTACCTTTTCTTGGTATGTAAGTCCGTA<br>ACTAGAATTACAGTGGGTTGCCATGGCACTCTG<br>TGGTCTTTTGGTTCATGCATGGGTCTTGCGCAA<br>GAAAAAGACAAAGAACAAAGAAAAAAGACAAAA<br>CAGAGAGACAAAACGCAATCACACAACCAACTC<br>AAATTAGTCACTGGCTGATCAAGATCGCCGCGT<br>CCATGTATGTCTAAATGCCATGCAAAGCAACAC<br>GTGCTTAACATGCACTTTAAATGGCTCACCCATC<br>TCAACCCACACACAAACACATTGCCTTTTTCTTC<br>ATCATCACCACAACCACCTGTATATATTCATTCT<br>CTTCCGCCACCTCAATTTCTTCACTTCAACACAC<br>GTCAACCTGCATATGCGTGTCATCCCATGCCCA<br>AATCTCCATGCATGTTCCAACCACCTTCTCTCTT<br>ATATAATACCTATAAATACCTCTAATATCACTCA<br>CTTCTTTCATCATCCATCCATCCAGAGTACTACT<br>ACTCTACTACTATAATACCCCAACCCAACTCATA<br>TTCAATACTACTCTACT<br>3' |

What is claimed is:

1. A transgenic soybean plant comprising a nucleic acid encoding for a hemeprotein, wherein the nucleic acid is operatively linked to:

a beta-phaseolin (phas) seed-specific promoter at the 5' end of the nucleic acid encoding for the hemeprotein;

an arc5 terminator at the 3' end of the nucleic acid encoding for the hemeprotein; and a Rb7Mar 3' Matrix Attachment Region at the 3' end of the arc5 terminator; wherein the hemeprotein is expressed in a seed of the transgenic soybean plant and comprises about 5% to about 30% of the total soluble protein of the seed.

2. The transgenic soybean plant of claim 1, wherein the phas seed-specific promoter comprises a sequence with at least 70% identity to SEQ ID NO: 14, the arc5 terminator comprises a sequence with at least 70% identity to SEQ ID NO: 12, and the Rb7Mar 3' Matrix Attachment Region comprises a sequence with at least 70% identity to SEQ ID NO: 13.

3. The transgenic soybean plant of claim 1, wherein the hemeprotein is selected from a plant derived heme protein, a microorganism derived heme protein, or an animal derived heme protein.

4. The transgenic soybean plant of claim 1, wherein the heme protein comprises a heme protein involved in oxygen transport, an enzyme having a heme prosthetic group, or a heme protein involved in the electron transport chain.

5. The transgenic soybean plant of claim 1, wherein the heme protein is selected from: hemoglobin, myoglobin, neuroglobin, cytoglobin, cytochrome P450s, cytochrome c oxidase, ligninases, catalase, peroxidases, cytochrome a, cytochrome b, or cytochrome c.

6. The transgenic soybean plant of claim 1, wherein the heme protein is an animal derived heme protein selected from the group consisting of hemoglobin and myoglobin.

7. The transgenic soybean plant of claim 1, wherein the transgenic soybean plant is a transgenic *Glycine max* plant.

8. A transgenic soybean seed comprising a nucleic acid encoding for a hemeprotein, wherein said nucleic acid is operatively linked to:

a beta-phaseolin (phas) seed-specific promoter at the 5' end of the nucleic acid encoding for the hemeprotein;

an arc5 terminator at the 3' end of the nucleic acid encoding for the hemeprotein; and a Rb7Mar 3' Matrix Attachment Region at the 3' end of the arc5 terminator;

wherein said hemeprotein is expressed in the transgenic soybean seed between about 5% to about 30% of the total soluble protein of the transgenic soybean seed.

9. The transgenic soybean seed of claim 8, wherein the phas seed-specific promoter comprises a sequence with at least 70% identity to SEQ ID NO: 14, the arc5 terminator comprises a sequence with at least 70% identity to SEQ ID NO: 12, and the Rb7Mar 3' Matrix Attachment Region comprises a sequence with at least 70% identity to SEQ ID NO: 13.

10. The transgenic soybean seed of claim 8, wherein said hemeprotein is selected from a plant derived hemeprotein, a microorganism derived hemeprotein, or an animal derived hemeprotein.

11. The transgenic soybean seed of claim 8, wherein said heme protein comprises a hemeprotein involved in oxygen transport, an enzyme having a heme prosthetic group, or a heme protein involved in the electron transport chain.

12. The transgenic soybean seed of claim 8, wherein said heme protein is selected from: hemoglobin, myoglobin, neuroglobin, cytoglobin, cytochrome P450s, cytochrome c oxidase, ligninases, catalase, peroxidases, cytochrome a, cytochrome b, or cytochrome c.

13. The transgenic soybean seed of claim 8, wherein said heme protein is an animal derived heme protein selected from the group consisting of hemoglobin and myoglobin.

14. The transgenic soybean seed of claim 8, wherein the transgenic soybean seed is a transgenic *Glycine max* seed.

15. A food composition comprising the transgenic soybean plant of claim 1.

16. The food composition of claim 15, comprising a hemeprotein isolated from the transgenic soybean plant.

17. A method to produce hemeproteins in a soybean plant seed, the method comprises:

transforming a soybean plant with a nucleic acid encoding for a hemeprotein, wherein the nucleic acid is operatively linked to a beta-phaseolin (phas) seed-specific promoter located at the 5' end of the nucleic acid encoding for the hemeprotein, an arc5 terminator located at the 3' end of the nucleic acid encoding for the hemeprotein, and a Rb7Mar 3' Matrix Attachment Region located at the 3' end of the arc5 terminator;

selecting the transformed soybean plants, and cultivating the transformed soybean plants to produce the hemeproteins;

wherein the hemeprotein comprises about 5% to about 30% of the total soluble proteins in the soybean seed.

18. The method of claim 17, wherein the phas seed-specific promoter comprises a sequence with at least 70% identity to SEQ ID NO: 14, the arc5 terminator comprises a sequence with at least 70% identity to SEQ ID NO: 12, and the Rb7Mar 3' Matrix Attachment Region comprises a sequence with at least 70% identity to SEQ ID NO: 13.

19. The method of claim 17, wherein the soybean plant seed is a *Glycine max* plant seed.

20. The method of claim 17, wherein the hemeprotein is selected from a plant derived heme protein, a microorganism derived heme protein, or an animal derived heme protein.

21. The method of claim 17, wherein said hemeprotein comprises a hemeprotein involved in oxygen transport, an enzyme having a heme prosthetic group, or a hemeprotein involved in the electron transport chain.

22. The method of claim 17, wherein said heme protein is selected from: hemoglobin, myoglobin, neuroglobin, cytoglobin, cytochrome P450s, cytochrome c oxidase, ligninases, catalase, peroxidases, cytochrome a, cytochrome b, or cytochrome c.

23. The method of claim 17, wherein said heme protein is an animal derived heme protein selected from the group consisting of hemoglobin and myoglobin.

24. A food composition comprising the transgenic soybean seed of claim 8.

25. The food composition of claim 24, wherein the food is texturized.

26. The food composition of claim 24, wherein the food is a meat analog.

* * * * *

SEQUENCE LISTING

Sequence total quantity: 14
SEQ ID NO: 1          moltype = DNA   length = 930
FEATURE               Location/Qualifiers
misc_feature          1..930
                      note = porcine hemoglobin (HbALLHbB)
source                1..930
                      mol_type = other DNA
                      organism = synthetic construct
SEQUENCE: 1
tcaatgatac ttgtgagcaa gagcatttgc tacgccggca acaaccttct gaaatgcagc    60

-continued

```
ctgcacatta gggttgaaat catgaccaag tctacgggct aggactacaa caatgacgtt  120
gccgagtagg cgaaaatttt cagggtcgac gtgaagttga tcacaatgca actcagataa  180
cttcgcaaaa gtacctttca ggttgtccaa atgcttcagc ccatcagaga atgattgcaa  240
tactttcttt ccatgagctt tcacttttgg atttcccata acagcatctg cattggacaa  300
atcaccaaag ctctcaaaga atctttgtgt ccaggggtaa accacaagga gcctcccaag  360
tgcctctcca ccaacttcat caacattaac ttttccccac aaccctaaca ctgcttcctt  420
ttcctcagca ctgaggtgca cacttcctcc acctccagat cctccacctc ctgatcctcc  480
acctcctgat cctccacctc cactcctata tttgctggtg agtacagttg agacgttggc  540
gaggaacttg tccaaactgg catgcacaga aggattaaaa tcatctggat ggtgggcggc  600
taaagtgact aacaaacaat gggacagcag cttgaaattt accggatcaa ctctcaattt  660
gtgtgcatga agatcagata atgcagaaag tgcgccggga aggtcatcca agtgcccaac  720
agcttttgtc aaagcatcag ccaccttctg cccatgtgcc ttcacttgat cacttccatg  780
tgagaggttg aaatgaggaa agtaagtctt tgtcgttgga aagccaagaa acatacgctc  840
aagagcttca gcaccgtgcg ctccagcttg accaccaact tttccccaag cagccttaac  900
atttgctttg tctgctgccg atagaaccat                                   930

SEQ ID NO: 2            moltype = DNA  length = 465
FEATURE                 Location/Qualifiers
misc_feature            1..465
                        note = porcine Myoglobin
source                  1..465
                        mol_type = other DNA
                        organism = synthetic construct
SEQUENCE: 2
atggggctat cagatggtga atggcaactt gtattgaatg tttggggaaa agttgaagct  60
gatgttgctg gacatggtca agaagtgtta ataagactct tcaaaggcca ccctgaaaca  120
ttagagaagt ttgacaaatt caagcaccta aaatctgaag atgaaatgaa ggcctccgag  180
gacttgaaga agcatggaaa cactgtcctg actgcactcg gcgggatcct caaaaagaaa  240
ggtcatcatg aagcggagtt gacaccattg gctcagtctc atgctaccaa acacaagatt  300
cctgtgaagt atcttgagtt tattagtgag gccataattc aggttttgca atcaaaacat  360
cccggtgatt ttggtgcaga tgctcaagga gcaatgagca aagcactgga gcttttcagg  420
aatgatatgg cagccaagta caaggaactt ggatttcagg ggtga                  465

SEQ ID NO: 3            moltype = DNA  length = 4728
FEATURE                 Location/Qualifiers
misc_feature            1..4728
                        note = pIPTRA0:p35S+HbA-LL-HbB
source                  1..4728
                        mol_type = other DNA
                        organism = synthetic construct
SEQUENCE: 3
tggcaggata tattgtggtg taaacaaatt gacgcttaga caacttaata acacattgcg  60
gacgttttta atgtactgaa ttaacgccga attgctctag cattcgccat tcaggctgcg  120
caactgttgg gaagggcgat cggtgcgggc ctcttcgcta ttacgccagc tggcgaaagg  180
gggatgtgct gcaaggcgat taagttgggt aacgccaggg ttttcccagt cacgacgttg  240
taaaacgacg gccagtgcca agctaattcg cttcaagacg tgctcaaatc actatttcca  300
cacccctata tttctattgc actccctttt aactgttttt tattacaaaa atgccctgga  360
aaatgcactc cctttttgtg tttgtttttt tgtgaaacga tgttgtcagg taatttattt  420
gtcagtctac tatggtggcc cattatatta atagcaactg tcggtccaat agacgacgtc  480
gattttctgc atttgtttaa ccacgtggat tttatgacat tttatattag ttaatttgta  540
aaacctaccc aattaaagac ctcatatgtt ctaaagacta atacttaatg ataacaattt  600
tcttttagtg aagaaaggga taattagtaa atatggaaca agggcagaag atttattaaa  660
gccgcgtaag agacaacaag taggtacgtg gagtgtctta ggtgacttac ccacataaca  720
taaagtgaca ttaacaaaca tagctaatgc tcctatttga atagtgcata tcagcatacc  780
ttattacata tagataggag caaactctag ctagattgtt gagcagatct cggtgacggg  840
caggaccgga cggggcggta ccggcaggct gaagtccagc tgccagaaac ccacgtcatg  900
ccagttcccg tgcttgaagc cggccgcccg cagcatgccg cgggggggcat atccgagcgc  960
ctcgtgcatg cgcacgctcg ggtcgttggg cagcccgatg acagcgacca cgctcttgaa  1020
gccctgtgcc tccagggact tcagcaggtg ggtgtagagc gtggagccca gtcccgtccg  1080
ctggtggcgg ggggagacgt acacggtcga ctcggccgtc cagtcgtagg cgttgcgtgc  1140
cttccagggg cccgcgtagg cgatgccggc gacctcgccg tccacctcgg cgacgagcca  1200
gggatagcgc tcccgcagac ggacgaggtc gtccgtccac tcctgcggtt cctgcggctc  1260
ggtacggaag ttgaccgtgc ttgtctcgat gtagtggttg acgatggtgc agaccgccgg  1320
catgtccgcc tcggtggcac ggcggatgtc ggccgggcgt cgttctgggc tcatggtaga  1380
tcccccgttc gtaaatggtg aaaattttca gaaaattgct tttgctttaa aagaaatgat  1440
ttaaattgct gcaatagaag tagaatgctt gattgcttga gattcgtttg ttttgtatat  1500
gttgtgttga gaattaattc tcgaggtcct ctccaaatga aatgaacttc cttatataga  1560
ggaagggtct tgcgaaggat agtgggattg tgcgtcatcc cttacgtcag tggagatatc  1620
acatcaatcc acttgctttg aagacgtggt tggaacgtct tctttttcca cgatgctcct  1680
cgtgggtggg ggtccatctt tgggaccact gtcggcagag gcatcttcaa cgatggcctt  1740
tcctttatcg caatgatggc atttgtagga gccaccttcc ttttccacta tcttcacaat  1800
aaagtgacag atagctgggc aatggaatcc gaggaggttt ccggatatta ccctttgttg  1860
aaaagtctca attgcccttt ggtcttctga gactgtatct ttgatatttt tggagtagac  1920
aagtgtgtcg tgctccacca tgttatcaca tcaatccact tgctttgaag acgtggttgg  1980
aacgtcttct ttttccacga tgctcctcgt gggtgggggt ccatctttgg gaccactgtc  2040
ggcagaggca tcttcaacga tggcctttcc tttatcgcaa tgatggcatt tgtaggagcc  2100
accttccttt tccactatct tcacaataaa gtgacagata gctgggcaat ggaatccgag  2160
gaggtttccg gatattaccc tttgttgaaa agtctcaatt gccctttggt cttctgagac  2220
tgtatctttg atatttttgg agtagacaag tgtgtcgtgc tccaccatgt tgacctgcag  2280
```

-continued

```
actagtccga tctagtaaca tagatgacac cgcgcgcgat aatttatcct agtttgcgcg  2340
ctatattttg ttttctatcg cgtattaaat gtataattgc gggactctaa tcataaaaac  2400
ccatctcata aataacgtca tgcattacat gttaattatt acatgcttaa cgtaattcaa  2460
cagaaattat atgataatca tcgcaagacc ggcaacagga ttcaatctta agaaacttta  2520
ttgccaaatg tttgaacgat cggggaaatt gagctcgccc gggaaagctt caatgatact  2580
tgtgagcaag agcatttgct acgccggcaa caaccttctg aaatgcagcc tgcacattag  2640
ggttgaaatc atgaccaagt ctacgggcta ggactacaac aatgacgttg ccgagtaggc  2700
gaaaattttc agggtcgacg tgaagttgat cacaatgcaa ctcagataac ttcgcaaaag  2760
tacctttcag gttgtccaaa tgcttcagcc catcagagaa tgattgcaat actttctttc  2820
catgagcttt cacttttgga tttcccataa cagcatctgc attggacaaa tcaccaaagc  2880
tctcaaagaa tctttgtgtc caggggtaaa ccacaaggag cctcccaagt gcctctccac  2940
caacttcatc aacattaact tttccccaca accctaacac tgcttccttt tcctcagcac  3000
tgaggtgcac acttcctcca cctccagatc ctccacctcc tgatcctcca cctcctgatc  3060
ctccacctcc actcctatat ttgctggtga gtacagttga gacgttggcg aggaacttgt  3120
ccaaactggc atgcacagaa ggattaaaat catctggatg gtgggcggct aaagtgacta  3180
acaaacaatg ggacagcagc ttgaaattta ccggatcaac tctcaatttg tgtgcatgaa  3240
gatcagataa tgcagaaagt gcgccgggaa ggtcatccaa gtgcccaaca gcttttgtca  3300
aagcatcagc caccttctgc ccatgtgcct tcacttgatc acttccatgt gagaggttga  3360
aatgaggaaa gtaagtcttt gtcgttggaa agccaagaaa catacgctca agagcttcag  3420
caccgtgcgc tccagcttga ccaccaactt ttccccaagc agccttaaca tttgctttgt  3480
ctgctgccga tagaaccatg gatcctctag tggtagatcc cccgttcgta aatggtgaaa  3540
attttcagaa aattgctttt gctttaaaag aaatgattta aattgctgca atagaagtag  3600
aatgcttgat tgcttgagat tcgtttgttt tgtatatgtt gtgttgagaa ttaattctcg  3660
aggtcctctc caaatgaaat gaacttcctt atatagagga agggtcttgc gaaggatagt  3720
gggattgtgc gtcatccctt acgtcagtgg agatatcaca tcaatccact tgctttgaag  3780
acgtggttgg aacgtcttct ttttccacga tgctcctcgt gggtgggggt ccatctttgg  3840
gaccactgtc ggcagaggca tcttcaacga tggcctttcc tttatcgcaa tgatggcatt  3900
tgtaggagcc accttccttt tccactatct tcacaataaa gtgacagata gctgggcaat  3960
ggaatccgag gaggtttccg gatattaccc tttgttgaaa agtctcaatt gccctttggt  4020
cttctgagac tgtatctttg atatttttgg agtagacaag tgtgtcgtgc tccaccatgt  4080
tatcacatca atccacttgc tttgaagacg tggttggaac gtcttctttt tccacgatgc  4140
tcctcgtggg tgggggtcca tctttgggac cactgtcggc agaggcatct tcaacgatgg  4200
cctttccttt atcgcaatga tggcatttgt aggagccacc ttccttttcc actatcttca  4260
caataaagtg acagatagct gggcaatgga atccgaggag gtctccggat attacccttt  4320
gttgaaaagt ctcaattgcc ctttggtctt ctgagactgt atctttgata tttttggagt  4380
agacaagtgt gtcgtgctcc accatgttga ctctagagaa ttcgtaatca tgtcatagct  4440
gtttcctgtg tgaaattgtt atccgctcac aattccacac aacatacgag ccggaagcat  4500
aaagtgtaaa gcctggggtg cctaatgagt gagctaactc acattaattg cgttgcgctc  4560
actgcccgct ttccagtcgg gaaacctgtc gtgccagctg cattaatgaa tcggccaacg  4620
cgcggggaga ggcggtttgc gtattggagc ttgagcttgg atcagattgt cgtttcccgc  4680
cttcagttta aactatcagt gtttgacagg atatattggc gggtaaac               4728

SEQ ID NO: 4           moltype = DNA  length = 5649
FEATURE                Location/Qualifiers
source                 1..5649
                       mol_type = other DNA
                       organism = synthetic construct
misc_feature           1..5649
                       note = pIPTRA0:p7S+HbA-LL-HbB-Arc5T
SEQUENCE: 4
tggcaggata tattgtggtg taaacaaatt gacgcttaga caacttaata acacattgcg  60
gacgttttta atgtactgaa ttaacgccga attgctctag cattcgccat tcaggctgcg  120
caactgttgg gaagggcgat cggtgcgggc ctcttcgcta ttacgccagc tggcgaaagg  180
gggatgtgct gcaaggcgat taagttgggt aacgccaggg ttttcccagt cacgacgttg  240
taaaacgacg gccagtgcca agctaattcg cttcaagacg tgctcaaatc actatttcca  300
caccccctata tttctattgc actccctttt aactgttttt tattacaaaa atgccctgga  360
aaatgcactc cctttttgtg tttgtttttt tgtgaaacga tgttgtcagg taatttattt  420
gtcagtctac tatggtggcc cattatatta atagcaactg tcggtccaat agacgacgtc  480
gattttctgc atttgtttaa ccacgtggat tttatgacat tttatattag ttaatttgta  540
aaacctaccc aattaaagac ctcatatgtt ctaaagacta atacttaatg ataacaattt  600
tcttttagtg aagaaaggga taattagtaa atatggaaca agggcagaag atttattaaa  660
gccgcgtaag agacaacaag taggtacgtg gagtgtctta ggtgacttac ccacataaca  720
taaagtgaca ttaacaaaca tagctaatgc tcctatttga atagtgcata tcagcatacc  780
ttattacata tagataggag caaactctag ctagattgtt gagcagatct cggtgacggg  840
caggaccgga cggggcggta ccggcaggct gaagtccagc tgccagaaac ccacgtcatg  900
ccagttcccg tgcttgaagc cggccgcccg cagcatgccg cgggggggcat atccgagcgc  960
ctcgtgcatg cgcacgctcg ggtcgttggg cagcccgatg acagcgacca cgctcttgaa  1020
gccctgtgcc tccagggact tcagcaggtg ggtgtagagc gtggagccca gtcccgtccg  1080
ctggtggcgg ggggagacgt acacggtcga ctcggccgtc cagtcgtagg cgttgcgtgc  1140
cttccagggg cccgcgtagg cgatgccggc gacctcgccg tccacctcgg cgacgagcca  1200
gggatagcgc tcccgcagac ggacgaggtc gtccgtccac tcctgcggtt cctgcggctc  1260
ggtacggaag ttgaccgtgc ttgtctcgat gtagtggttg acgatggtgc agaccgccgg  1320
catgtccgcc tcggtggcac ggcggatgtc ggccgggcgt cgttctgggc tcatggtaga  1380
tcccccgttc gtaaatggtg aaaattttca gaaaattgct tttgctttaa aagaaatgat  1440
ttaaattgct gcaatagaag tagaatgctt gattgcttga gattcgtttg ttttgtatat  1500
gttgtgttga gaattaattc tcgaggtcct ctccaaatga aatgaacttc cttatataga  1560
ggaagggtct tgcgaaggat agtgggattg tgcgtcatcc cttacgtcag tggagatatc  1620
acatcaatcc acttgctttg aagacgtggt tggaacgtct tctttttcca cgatgctcct  1680
cgtgggtggg ggtccatctt tgggaccact gtcggcagag gcatcttcaa cgatggcctt  1740
```

-continued

```
tcctttatcg caatgatggc atttgtagga gccaccttcc ttttccacta tcttcacaat  1800
aaagtgacag atagctgggc aatggaatcc gaggaggttt ccggatatta ccctttgttg  1860
aaaagtctca attgcccttt ggtcttctga gactgtatct ttgatatttt tggagtagac  1920
aagtgtgtcg tgctccacca tgttatcaca tcaatccact tgctttgaag acgtggttgg  1980
aacgtcttct ttttccacga tgctcctcgt gggtgggggt ccatctttgg gaccactgtc  2040
ggcagaggca tcttcaacga tggcctttcc tttatcgcaa tgatggcatt tgtaggagcc  2100
accttccttt tccactatct tcacaataaa gtgacagata gctgggcaat ggaatccgag  2160
gaggtttccg gatattaccc tttgttgaaa agtctcaatt gccctttggt cttctgagac  2220
tgtatctttg atatttttgg agtagacaag tgtgtcgtgc tccaccatgt tgacctgcag  2280
actagtcact attttcagaa gaagttccca atagtagtcc aaaatttttg taacgaaggg  2340
agcataatag ttacatgcaa aggaaaactg ccattcttta gaggggatgc ttgtttaaga  2400
acaaaaaata tatcactttc ttttgttcca agtcattgcg tattttttta aaaatatttg  2460
ttccttcgta tatttcgagc ttcaatcact ttatggttct ttgtattctg gctttgctgt  2520
aaatcgtagc taaccttctt cctagcagaa attattaata cttgggatat ttttttagaa  2580
tcaagtaaat tacatattac caccacatcg agctgctttt aaattcatat tacagccata  2640
taggcttgat tcattttgca aaatttccag gatattgaca acgttaactt aataatatct  2700
tgaaatatta aagctattat gattaggggt gcaaatggac cgagttggtg gtgtaaatat  2760
atgagctccc attttattta ttgctcccat tttatttatt ttagtttgtg tgacagatga  2820
acattattag gaggaaaggt ataagcaggg tttaactgtc acagggaagg tggttttggg  2880
agtctaaagc ttcaatgata cttgtgagca agagcatttg ctacgccggc aacaaccttc  2940
tgaaatgcag cctgcacatt agggttgaaa tcatgaccaa gtctacgggc taggactaca  3000
acaatgacgt tgccgagtag gcgaaaattt tcagggtcga cgtgaagttg atcacaatgc  3060
aactcagata acttcgcaaa agtacctttc aggttgtcca aatgcttcag cccatcagag  3120
aatgattgca atactttctt tccatgagct ttcacttttg gatttcccat aacagcatct  3180
gcattggaca aatcaccaaa gctctcaaag aatctttgtg tccaggggta aaccacaagg  3240
agcctcccaa gtgcctctcc accaacttca tcaacattaa cttttcccca caaccctaac  3300
actgcttcct tttcctcagc actgaggtgc acacttcctc cacctccaga tcctccacct  3360
cctgatcctc cacctcctga tcctccacct ccactcctat atttgctggt gagtacagtt  3420
gagacgttgg cgaggaactt gtccaaactg gcatgcacag aaggattaaa atcatctgga  3480
tggtgggcgg ctaaagtgac taacaaacaa tgggacagca gcttgaaatt taccggatca  3540
actctcaatt tgtgtgcatg aagatcagat aatgcagaaa gtgcgccggg aaggtcatcc  3600
aagtgcccaa cagcttttgt caaagcatca gccaccttct gcccatgtgc cttcacttga  3660
tcacttccat gtgagaggtt gaaatgagga aagtaagtct ttgtcgttgg aaagccaaga  3720
aacatacgct caagagcttc agcaccgtgc gctccagctt gaccaccaac ttttccccaa  3780
gcagccttaa catttgcttt gtctgctgcc gatagaacca tggatccggc tatcgttcgt  3840
aaatggtgaa aattttcaga aaattgcttt tgctttaaaa gaaatgattt aaattgctgc  3900
aatagaagta gaatgcttga ttgcttgaga ttcgtttgtt ttgtatatgt tgtgttgaga  3960
attgttgtgt tagagagcta caatatatag agaaagatca ccgtttggct agctttaagt  4020
ggctaagtgt gaacgggatg agattctctt ttcttttggc cgtgttggtc acaagattgg  4080
acgtcgacgt gtttgaggct tgtgaaattt ccagaagcaa agaaaggata aacttgagtt  4140
aacatgcaat ggggagaaaa acaaagggtt ggtgagtgtg aggggtactt ggcagctgag  4200
aacaatgctt tagttgcatg ccatgcagat ttcatccgtt tgaaactctg taaaggacgt  4260
gtggatcgag ttcgcgtgag cagctagctt ggcttggatt tttgtcttgc tatccctcta  4320
ctacattaat ttccctacat gcaactgttt catgacattt tcgtgtatct cccaactggc  4380
tagctcatat taactaagga aaatagaatt ctaatggaaa atttaaataa tagactttca  4440
tattttattt gtccccctca aatttttttac atttcatttt ttcgatttta ttctatttat  4500
ttttttattc ttttttttaaa aattggcatt ctaaacccta tatattatat gaaataatat  4560
attttttaac aaactcttta ttattcatca aaattataaa tgcatgaatg aagtattata  4620
taagaagtga aacttataaa attatgtaat ttataataag tttcaagtac gcgtgttcac  4680
caacaaaatc acgtgaaaaa ttgaacaaaa gacgcaaaag caagaccaag tagcctcctg  4740
agtgatgcgc ttcaactgtt gcaaacacta acctaaacat agacggcttc tagggtgcgc  4800
aaagttgaaa tgtgaggcac ggtacacaag tttttttagg accgttggat ataacactta  4860
attagttaac ggtgcaaatc tccaagattt tagaagtgga aaaagtattg aataaaaaag  4920
tatcgcattt actgtagagc aaactcttat tttaatattg ttgggtcacg tgggtgtggg  4980
cttctcgact ccaccggatg atgttttcaa ttttgatttc tttttttttcc taaaggtttt  5040
ccatttacat ttattttggt tagaaaaaag aataaggcta aatgtctaaa ccaacttgca  5100
ttcgaaccta gaactaaaat aatctaccac cacgccatca tcaactttat actttgaaa  5160
agtatttata acaatatata tattttatca aacatgctta attgccttaa aataaaattt  5220
ataaattagt tggtaatatt ttaacaatat taacggattt ctggtaaaaa aaaataaaat  5280
catgaatttc taaaatttta aaatcaaatt ttttaatgta tagattattt tatctagaga  5340
attcgtaatc atgtcatagc tgtttcctgt gtgaaattgt tatccgctca caattccaca  5400
caacatacga gccggaagca taaagtgtaa agcctggggt gcctaatgag tgagctaact  5460
cacattaatt gcgttgcgct cactgcccgc tttccagtcg ggaaacctgt cgtgccagct  5520
gcattaatga atcggccaac gcgcggggag aggcggtttg cgtattggag cttgagcttg  5580
gatcagattg tcgtttcccg ccttcagttt aaactatcag tgtttgacag gatatattgg  5640
cgggtaaac                                                          5649
```

```
SEQ ID NO: 5            moltype = DNA  length = 1667
FEATURE                 Location/Qualifiers
misc_feature            1..1667
                        note = 35S+TEV+myoglobincDNA+NOS
source                  1..1667
                        mol_type = other DNA
                        organism = synthetic construct
SEQUENCE: 5
aataatgcgg ccgcatggtg gagcacgaca ctctcgtcta ctccaagaat atcaaagata  60
cagtctcaga agaccaaagg gctattgaga cttttcaaca aagggtaata tcgggaaacc  120
tcctcggatt ccattgccca gctatctgtc acttcatcaa aaggacagta gaaaaggaag  180
gtggcaccta caaatgccat cattgcgata aaggaaaggc tatcgttcaa gatgcctctg  240
```

```
ccgacagtgg tcccaaagat ggacccccac ccacgaggag catcgtggaa aaagaagacg  300
ttccaaccac gtcttcaaag caagtggatt gatgtgataa catggtggag cacgacactc  360
tcgtctactc caagaatatc aaagatacag tctcagaaga ccaaagggct attgagactt  420
ttcaacaaag ggtaatatcg ggaaacctcc tcggattcca ttgcccagct atctgtcact  480
tcatcaaaag gacagtagaa aaggaaggtg gcacctacaa atgccatcat tgcgataaag  540
gaaaggctat cgttcaagat gcctctgccg acagtggtcc caaagatgga cccccaccca  600
cgaggagcat cgtggaaaaa gaagacgttc caaccacgtc ttcaaagcaa gtggattgat  660
gtgatatctc cactgacgta agggatgacg cacaatccca ctatccttcg caagaccttc  720
ctctatataa ggaagttcat ttcatttgga gaggacacgc tgaaatcacc agtctctctc  780
tacaaatcta tctctgaatt aattctcaac acaacatata caaaacaaac gaatctcaag  840
caatcaagca ttctacttct attgcagcaa tttaaatcat ttcttttaaa gcaaaagcaa  900
ttttctgaaa attttcacca tttacgaacg atagatgggg ctatcagatg gtgaatggca  960
acttgtattg aatgtttggg gaaaagttga agctgatgtt gctggacatg gtcaagaagt  1020
gttaataaga ctcttcaaag gccaccctga aacattagag aagtttgaca aattcaagca  1080
cctaaaatct gaagatgaaa tgaaggcctc cgaggacttg aagaagcatg gaaacactgt  1140
cctgactgca ctcggcggga tcctcaaaaa gaaaggtcat catgaagcgg agttgacacc  1200
attggctcag tctcatgcta ccaaacacaa gattcctgtg aagtatcttg agtttattag  1260
tgaggccata attcaggttt tgcaatcaaa acatcccggt gattttggtg cagatgctca  1320
aggagcaatg agcaaagcac tggagctttt caggaatgat atggcagcca agtacaagga  1380
acttggattt caggggtgag atcgttcaaa catttggcaa taaagtttct taagattgaa  1440
tcctgttgcc ggtcttgcga tgattatcat ataatttctg ttgaattacg ttaagcatgt  1500
aataattaac atgtaatgca tgacgttatt tatgagatgg gtttttatga ttagagtccc  1560
gcaattatac atttaatacg cgatagaaaa caaaatatag cgcgcaaact aggataaatt  1620
atcgcgcgcg gtgtcatcta tgttactaga tcggcggccg cttatta              1667
```

```
SEQ ID NO: 6            moltype = DNA  length = 3232
FEATURE                 Location/Qualifiers
misc_feature            1..3232
                        note = p7S+TEV+myoglobincDNA+arc5+Rb7MAR
source                  1..3232
                        mol_type = other DNA
                        organism = synthetic construct
SEQUENCE: 6
aaatttgcgg ccgcggtact tggcagctga gaacaatgct ttagttgcat gccatgcaga  60
tttcatccgt ttgaaactct gtaaaggacg tgtggatcga gttcgcgtga gcagctagct  120
tggcttggat ttttgtcttg ctatccctct actacattaa tttccctaca tgcaactgtt  180
tcatgacatt ttcgtgtatc tcccaactgg ctagctcata ttaactaagg aaaatagaat  240
tctaatggaa aatttaaata atagactttc atattttatt tgtccccctc aaattttta  300
catttcattt tttcgatttt attctattta tttttttatt cttttttaa aaattggcat  360
tctaaaccct atatattata tgaaataata tattttttaa caaactcttt attattcatc  420
aaaattataa atgcatgaat gaagtattat ataagaagtg aaacttataa aattatgtaa  480
tttataataa gtttcaagta cgcgtgttca ccaacaaaat cacgtgaaaa attgaacaaa  540
agacgcaaaa gcaagaccaa gtagcctcct gagtgatgcg cttcaactgt tgcaaacact  600
aacctaaaca tagacggctt ctagggtgcg caaagttgaa atgtgaggca cggtacacaa  660
gttttttag gaccgttgga tataacactt aattagttaa cggtgcaaat ctccaagatt  720
ttagaagtgg aaaaagtatt gaataaaaaa gtatcgcatt tactgtagag caaactctta  780
ttttaatatt gttgggtcac gtgggtgtgg gcttctcgac tccaccggat gatgtttca  840
attttgattt cttttttttg ctaaaggttt tccatttaca tttattttgg ttagaaaaaa  900
gaataaggct aaatgcctaa accaacttgc attcgaacct agaactaaaa taatctacca  960
ccacgccatc atcaacttta tacttttgaa aagtatttat aacaatatat atattttatc  1020
aaacatgctt aattgcctta aaataaaatt tataaattag ttggtaatat tttaacaata  1080
ttaacaaatt tctggtaaaa aaattaaaat catgaatttc taaaatttta aaatcaaatt  1140
ttttaatgta taggttattt taatttaatt tatattgtta aaaatgggtt attacaattt  1200
aattaatctc taattaaaat atatatgagg atattagttt tattctaata ctattgtaat  1260
tcccattcat atgaatatat atatatgaga ttgtttgata aaataatctc aataaatgtt  1320
tcaactatgc aaagcataat gagcatctaa cttatttaca atttacaata ataaatcatg  1380
atcaaaacaa acatcaacac taactcgtta ttagtatgtt atcaacaaat gtaaaggtga  1440
agctactcta gcttaagtca aagttaaatt attctgatca gaaactcttt gaaaatatac  1500
ctaataaaac tcaagaaaat acacacctaa tataaacata tgttgaacat ctttatacat  1560
gtgcatcttc aaacccctat tcattccatc tattgtgtct ccaagaagga gatccaacct  1620
ataagtcatt tcctcccatg tacgtcatgt ataggatcat tacagtcaca gccacatgtg  1680
ttatatgcaa ggatttaatt agtagtgtaa aaacttgagt ggaatccttc aaggattaga  1740
aagagaaact aaggtaaatt aagagattta ctgaatcaat ataaatcttt tgtttttact  1800
cgagcttcta ttatacttgt tttatcttag ttgcttctat cttactttcg atgtttaaat  1860
tttgagaaaa aaatcctttt gtgaaaaacc tttttaaaaa gttgtttgac gctaccgtac  1920
agagcatcca tttttaattt gtggtcaaat ttgctttgtg aaaatcttca tcttacaaaa  1980
aaaaaacctt aatttaaatc tcatctaaca tattgaatta attctcaaca caacatatac  2040
aaaacaaacg aatctcaagc aatcaagcat tctacttcta ttgcagcaat ttaaatcatt  2100
tcttttaaag caaaagcaat tttctgaaaa ttttcaccat ttacgaacga tagatggggc  2160
tatcagatgg tgaatggcaa cttgtattga atgtttgggg aaaagttgaa gctgatgttg  2220
ctggacatgg tcaagaagtg ttaataagac tcttcaaagg ccaccctgaa acattagaga  2280
agtttgacaa attcaagcac ctaaaatctg aagatgaaat gaaggcctcc gaggacttga  2340
agaagcatgg aaacactgtc ctgactgcac tcggcgggat cctcaaaaag aaaggtcatc  2400
atgaagcgga gttgacacca ttggctcagt ctcatgctac caaacacaag attcctgtga  2460
agtatcttga gtttattagt gaggccataa ttcaggtttt gcaatcaaaa catcccggtg  2520
attttggtgc agatgctcaa ggagcaatga gcaaagcact ggagcttttc aggaatgata  2580
tggcagccaa gtacaaggaa cttggatttc aggggtgata gactcccaaa accaccttcc  2640
ctgtgacagt taaaccctgc ttatacttt cctcctaata atgttcatct gtcacacaaa  2700
ctaaaataaa taaaatggga gcaataaata aaatgggagc tcatatattt acaccaccaa  2760
```

-continued

```
ctcggtccat ttgcacccct aatcataata gctttaatat ttcaagatat tattaagtta  2820
acgttgtcaa tatcctggaa attttgcaaa atgaatcaag cctatatggc tgtaatatga  2880
atttaaaagc agctcgatgt ggtggtaata tgtaatttac ttgattctaa aaaaatatcc  2940
caagtattaa taatttctgc taggaagaag gttagctacg atttacagca aagccagaat  3000
acaaagaacc ataaagtgat tgaagctcga aatatacgaa ggaacaaata tttttaaaaa  3060
aatacgcaat gacttggaac aaaagaaagt gatatatttt ttgttcttaa acaagcatcc  3120
cctctaaaga atggcagttt tcctttgcat gtaactatta tgctcccttc gttacaaaaa  3180
ttttggacta ctattgggaa cttcttctga aaatagtggc ggccgcttaa ta          3232

SEQ ID NO: 7           moltype = DNA  length = 2635
FEATURE                Location/Qualifiers
misc_feature           1..2635
                       note = PPhas+myoglobincDNA+arc5+Rb7MAR
source                 1..2635
                       mol_type = other DNA
                       organism = synthetic construct
SEQUENCE: 7
aaatttgcgg ccgccattgt actcccagta tcattatagt gaaagttttg gctctctcgc  60
cggtggtttt ttacctctat ttaaaggggt tttccaccta aaaattctgg tatcattctc  120
actttacttg ttactttaat ttctcataat ctttggttga aattatcacg cttccgcaca  180
cgatatccct acaaatttat tatttgttaa acattttcaa accgcataaa attttatgaa  240
gtcccgtcta tctttaatgt agtctaacat tttcatattg aaatatataa tttacttaat  300
tttagcgttg gtagaaagca taaagattta ttcttattct tcttcatata aatgtttaat  360
atacaatata aacaaattct ttaccttaag aaggatttcc cattttatat tttaaaaata  420
tatttatcaa atatttttca accacgtaaa tctcataata ataagttgtt tcaaaagtaa  480
taaaatttaa ctccataatt tttttattcg actgatctta aagcaacacc cagtgacaca  540
actagccatt tttttctttg aataaaaaaa tccaattatc attgtatttt ttttatacaa  600
tgaaaatttc accaaacaat catttgtggt atttctgaag caagtcatgt tatgcaaaat  660
tctataattc ccatttgaca ctacggaagt aactgaagat ctgcttttac atgcgagaca  720
catcttctaa agtaatttta ataatagtta ctatattcaa gatttcatat atcaaatact  780
caatattact tctaaaaaat taattagata taattaaaat attacttttt taattttaag  840
tttaattgtt gaatttgtga ctattgattt attattctac tatgtttaaa ttgttttata  900
gatagtttaa agtaaatata agtaatgtag tagagtgtta gagtgttacc ctaaaccata  960
aactataaca tttatggtgg actaattttc atatatttct tattgctttt accttttctt  1020
ggtatgtaag tccgtaacta gaattacagt gggttgccat ggcactctgt ggtcttttgg  1080
ttcatgcatg ggtcttgcgc aagaaaaaga caaagaacaa agaaaaaaga caaaacagag  1140
agacaaaacg caatcacaca accaactcaa attagtcact ggctgatcaa gatcgccgcg  1200
tccatgtatg tctaaatgcc atgcaaagca acacgtgctt aacatgcact ttaaatggct  1260
cacccatctc aacccacaca caaacacatt gccttttct tcatcatcac cacaaccacc  1320
tgtatatatt cattctcttc cgccacctca atttcttcac ttcaacacac gtcaacctgc  1380
atatgcgtgt catcccatgc ccaaatctcc atgcatgttc caaccacctt ctctcttata  1440
taatacctat aaatacctct aatatcactc acttctttca tcatccatcc atccagagta  1500
ctactactct actactataa taccccaacc caactcatat tcaatactac tctactatgg  1560
ggctatcaga tggtgaatgg caacttgtat tgaatgtttg ggaaaaagtt gaagctgatg  1620
ttgctggaca tggtcaagaa gtgttaataa gactcttcaa aggccaccct gaaacattag  1680
agaagtttga caaattcaag cacctaaaat ctgaagatga aatgaaggcc tccgaggact  1740
tgaagaagca tggaaacact gtcctgactg cactcggcgg gatcctcaaa aagaaaggtc  1800
atcatgaagc ggagttgaca ccattggctc agtctcatgc taccaaacac aagattcctg  1860
tgaagtatct tgagtttatt agtgaggcca taattcaggt tttgcaatca aaacatcccg  1920
gtgattttgg tgcagatgct caaggagcaa tgagcaaagc actggagctt ttcaggaatg  1980
atatggcagc caagtacaag gaacttggat ttcaggggtg atagactccc aaaaccacct  2040
tccctgtgac agttaaaccc tgcttatacc tttcctccta ataatgttca tctgtcacac  2100
aaactaaaat aaataaaatg ggagcaataa ataaaatggg agctcatata tttacaccac  2160
caactcggtc catttgcacc cctaatcata atagctttaa tatttcaaga tattattaag  2220
ttaacgttgt caatatcctg gaaattttgc aaaatgaatc aagcctatat ggctgtaata  2280
tgaatttaaa agcagctcga tgtggtggta atatgtaatt tacttgattc taaaaaaata  2340
tcccaagtat taataatttc tgctaggaag aaggttagct acgatttaca gcaaagccag  2400
aatacaaaga accataaagt gattgaagct cgaaatatac gaaggaacaa atatttttaa  2460
aaaaatacgc aatgacttgg aacaaaagaa agtgatatat tttttgttct taaacaagca  2520
tcccctctaa agaatggcag ttttcctttg catgtaacta ttatgctccc ttcgttacaa  2580
aaattttgga ctactattgg gaacttcttc tgaaaatagt ggcggccgct taaat       2635

SEQ ID NO: 8           moltype = DNA  length = 781
FEATURE                Location/Qualifiers
misc_feature           1..781
                       note = 2x 35S promoter
source                 1..781
                       mol_type = other DNA
                       organism = synthetic construct
SEQUENCE: 8
atggtggagc acgacactct cgtctactcc aagaatatca aagatacagt ctcagaagac  60
caaagggcta ttgagacttt tcaacaaagg gtaatatcgg gaaacctcct cggattccat  120
tgcccagcta tctgtcactt catcaaaagg acagtagaaa aggaaggtgg cacctacaaa  180
tgccatcatt gcgataaagg aaaggctatc gttcaagatg cctctgccga cagtggtccc  240
aaagatggac ccccacccac gaggagcatc gtggaaaaag aagacgttcc aaccacgtct  300
tcaaagcaag tggattgatg tgataacatg gtggagcacg acactctcgt ctactccaag  360
aatatcaaag atacagtctc agaagaccaa agggctattg agacttttca acaaagggta  420
atatcgggaa acctcctcgg attccattgc ccagctatct gtcacttcat caaaaggaca  480
gtagaaaagg aaggtggcac ctacaaatgc catcattgcg ataaaggaaa ggctatcgtt  540
```

-continued

```
caagatgcct ctgccgacag tggtcccaaa gatggacccc cacccacgag gagcatcgtg  600
gaaaaagaag acgttccaac cacgtcttca aagcaagtgg attgatgtga tatctccact  660
gacgtaaggg atgacgcaca atcccactat ccttcgcaag accttcctct atataaggaa  720
gttcatttca tttggagagg acacgctgaa atcaccagtc tctctctaca aatctatctc  780
t                                                                  781

SEQ ID NO: 9            moltype = DNA  length = 139
FEATURE                 Location/Qualifiers
misc_feature            1..139
                        note = TEV
source                  1..139
                        mol_type = other DNA
                        organism = synthetic construct
SEQUENCE: 9
gaattaattc tcaacacaac atatacaaaa caaacgaatc tcaagcaatc aagcattcta  60
cttctattgc agcaatttaa atcatttctt ttaaagcaaa agcaattttc tgaaaatttt  120
caccatttac gaacgatag                                               139

SEQ ID NO: 10           moltype = DNA  length = 253
FEATURE                 Location/Qualifiers
misc_feature            1..253
                        note = NOS terminator
source                  1..253
                        mol_type = other DNA
                        organism = synthetic construct
SEQUENCE: 10
gatcgttcaa acatttggca ataaagtttc ttaagattga atcctgttgc cggtcttgcg  60
atgattatca tataatttct gttgaattac gttaagcatg taataattaa catgtaatgc  120
atgacgttat ttatgagatg ggtttttatg attagagtcc cgcaattata catttaatac  180
gcgatagaaa acaaaatata gcgcgcaaac taggataaat tatcgcgcgc ggtgtcatct  240
atgttactag atc                                                     253

SEQ ID NO: 11           moltype = DNA  length = 2000
FEATURE                 Location/Qualifiers
misc_feature            1..2000
                        note = 7S promoter
source                  1..2000
                        mol_type = other DNA
                        organism = synthetic construct
SEQUENCE: 11
ggtacttggc agctgagaac aatgctttag ttgcatgcca tgcagatttc atccgtttga  60
aactctgtaa aggacgtgtg gatcgagttc gcgtgagcag ctagcttggc ttggattttt  120
gtcttgctat ccctctacta cattaatttc cctacatgca actgtttcat gacattttcg  180
tgtatctccc aactggctag ctcatattaa ctaaggaaaa tagaattcta atggaaaatt  240
taaataatag actttcatat tttatttgtc cccctcaaat tttttacatt tcattttttc  300
gattttattc tatttatttt tttattcttt ttttaaaaat tggcattcta aaccctatat  360
attatatgaa ataatatatt ttttaacaaa ctctttatta ttcatcaaaa ttataaatgc  420
atgaatgaag tattatataa gaagtgaaac ttataaaatt atgtaattta taataagttt  480
caagtacgcg tgttcaccaa caaaatcacg tgaaaaattg aacaaaagac gcaaaagcaa  540
gaccaagtag cctcctgagt gatgcgcttc aactgttgca aacactaacc taaacataga  600
cggcttctag ggtgcgcaaa gttgaaatgt gaggcacggt acacaagttt ttttaggacc  660
gttggatata acacttaatt agttaacggt gcaaatctcc aagattttag aagtggaaaa  720
agtattgaat aaaaaagtat cgcatttact gtagagcaaa ctcttatttt aatattgttg  780
ggtcacgtgg gtgtgggctt ctcgactcca ccggatgatg ttttcaattt tgatttcttt  840
tttttgctaa aggttttcca tttacattta ttttggttag aaaaaagaat aaggctaaat  900
gcctaaacca acttgcattc gaacctagaa ctaaaataat ctaccaccac gccatcatca  960
actttatact tttgaaaagt atttataaca atatatatat tttatcaaac atgcttaatt  1020
gccttaaaat aaaatttata aattagttgg taatatttta acaatattaa caaatttctg  1080
gtaaaaaaat taaaatcatg aatttctaaa attttaaaat caaatttttt aatgtatagg  1140
ttattttaat ttaatttata ttgttaaaaa tgggttatta caatttaatt aatctctaat  1200
taaaatatat atgaggatat tagttttatt ctaatactat tgtaattccc attcatatga  1260
atatatatat atgagattgt ttgataaaat aatctcaata aatgtttcaa ctatgcaaag  1320
cataatgagc atctaactta tttacaattt acaataataa atcatgatca aaacaaacat  1380
caacactaac tcgttattag tatgttatca acaaatgtaa aggtgaagct actctagctt  1440
aagtcaaagt taaattattc tgatcagaaa ctctttgaaa atatacctaa taaaactcaa  1500
gaaaatacac acctaatata aacatatgtt gaacatcttt atacatgtgc atcttcaaac  1560
ccctattcat tccatctatt gtgtctccaa gaaggagatc caacctataa gtcatttcct  1620
cccatgtacg tcatgtatag gatcattaca gtcacagcca catgtgttat atgcaaggat  1680
ttaattagta gtgtaaaaac ttgagtggaa tccttcaagg attagaaaga gaaactaagg  1740
taaattaaga gatttactga atcaatataa atcttttgtt tttactcgag cttctattat  1800
acttgtttta tcttagttgc ttctatctta ctttcgatgt ttaaattttg agaaaaaaat  1860
ccttttgtga aaaacctttt taaaaagttg tttgacgcta ccgtacagag catccatttt  1920
taatttgtgg tcaaatttgc tttgtgaaaa tcttcatctt acaaaaaaaa aaccttaatt  1980
taaatctcat ctaacatatt                                              2000

SEQ ID NO: 12           moltype = DNA  length = 138
FEATURE                 Location/Qualifiers
misc_feature            1..138
                        note = Arc5 Terminator
```

-continued

```
source                  1..138
                        mol_type = other DNA
                        organism = synthetic construct
SEQUENCE: 12
tagactccca aaaccacctt ccctgtgaca gttaaaccct gcttatacct ttcctcctaa  60
taatgttcat ctgtcacaca aactaaaata aataaaatgg gagcaataaa taaaatggga  120
gctcatatat ttacacca                                                 138

SEQ ID NO: 13           moltype = DNA  length = 462
FEATURE                 Location/Qualifiers
misc_feature            1..462
                        note = Rb7 Mar
source                  1..462
                        mol_type = other DNA
                        organism = synthetic construct
SEQUENCE: 13
ccaactcggt ccatttgcac ccctaatcat aatagcttta atatttcaag atattattaa  60
gttaacgttg tcaatatcct ggaaattttg caaaatgaat caagcctata tggctgtaat  120
atgaatttaa aagcagctcg atgtggtggt aatatgtaat ttacttgatt ctaaaaaaat  180
atcccaagta ttaataattt ctgctaggaa gaaggttagc tacgatttac agcaaagcca  240
gaatacaaag aaccataaag tgattgaagc tcgaaatata cgaaggaaca aatattttta  300
aaaaaatacg caatgacttg gaacaaaaga aagtgatata tttttgttc ttaaacaagc  360
atcccctcta aagaatggca gttttccttt gcatgtaact attatgctcc cttcgttaca  420
aaaattttgg actactattg ggaacttctt ctgaaaatag tg                     462

SEQ ID NO: 14           moltype = DNA  length = 1542
FEATURE                 Location/Qualifiers
misc_feature            1..1542
                        note = Phas promoter
source                  1..1542
                        mol_type = other DNA
                        organism = synthetic construct
SEQUENCE: 14
cattgtactc ccagtatcat tatagtgaaa gttttggctc tctcgccggt ggttttttac  60
ctctatttaa aggggtttc cacctaaaaa ttctggtatc attctcactt tacttgttac  120
tttaatttct cataatcttt ggttgaaatt atcacgcttc cgcacacgat atccctacaa  180
atttattatt tgttaaacat tttcaaaccg cataaaattt tatgaagtcc cgtctatctt  240
taatgtagtc taacattttc atattgaaat atataattta cttaatttta gcgttggtag  300
aaagcataaa gatttattct tattcttctt catataaatg tttaatatac aatataaaca  360
aattctttac cttaagaagg atttcccatt ttatattta aaaatatatt tatcaaatat  420
ttttcaacca cgtaaatctc ataataataa gttgtttcaa aagtaataaa atttaactcc  480
ataattttt tattcgactg atcttaaagc aacacccagt gacacaacta gccatttttt  540
tctttgaata aaaaaatcca attatcattg tattttttt atacaatgaa aatttcacca  600
aacaatcatt tgtggtattt ctgaagcaag tcatgttatg caaaattcta taattcccat  660
ttgacactac ggaagtaact gaagatctgc ttttacatgc gagacacatc ttctaaagta  720
attttaataa tagttactat attcaagatt tcatatatca aatactcaat attacttcta  780
aaaaattaat tagatataat taaaatatta cttttttaat tttaagttta attgttgaat  840
ttgtgactat tgatttatta ttctactatg tttaaattgt tttatagata gtttaaagta  900
aatataagta atgtagtaga gtgttagagt gttaccctaa accataaact ataacattta  960
tggtggacta attttcatat atttcttatt gcttttacct tttcttggta tgtaagtccg  1020
taactagaat tacagtgggt tgccatggca ctctgtggtc ttttggttca tgcatgggtc  1080
ttgcgcaaga aaaagacaaa gaacaaagaa aaaagacaaa acagagagac aaaacgcaat  1140
cacacaacca actcaaatta gtcactggct gatcaagatc gccgcgtcca tgtatgtcta  1200
aatgccatgc aaagcaacac gtgcttaaca tgcactttaa atggctcacc catctcaacc  1260
cacacacaaa cacattgcct ttttcttcat catcaccaca accacctgta tatattcatt  1320
ctcttccgcc acctcaattt cttcacttca acacacgtca acctgcatat gcgtgtcatc  1380
ccatgcccaa atctccatgc atgttccaac caccttctct cttatataat acctataaat  1440
acctctaata tcactcactt ctttcatcat ccatccatcc agagtactac tactctacta  1500
ctataatacc ccaacccaac tcatattcaa tactactcta ct                     1542
```